(12) United States Patent
Chen et al.

(10) Patent No.: US 9,750,713 B2
(45) Date of Patent: *Sep. 5, 2017

(54) COMPOSITIONS AND METHODS OF USE OF PHORBOL ESTERS

(71) Applicant: Biosuccess Biotech Co. Ltd., Santa Clara, CA (US)

(72) Inventors: Hung-Fong Chen, Taipei (TW); Zheng Tao Han, Zhengzhou (CN)

(73) Assignee: Biosuccess Biotech Co. Ltd., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/154,100

(22) Filed: May 13, 2016

(65) Prior Publication Data

US 2016/0250173 A1 Sep. 1, 2016

Related U.S. Application Data

(63) Continuation of application No. 14/027,320, filed on Sep. 16, 2013, now Pat. No. 9,636,317, which is a continuation-in-part of application No. 13/745,740, filed on Jan. 18, 2013, which is a continuation-in-part of application No. 12/023,753, filed on Jan. 31, 2008, now abandoned, said application No. 14/027,320 is a continuation-in-part of application No. 13/745,745, filed on Jan. 18, 2013, now abandoned, and a continuation-in-part of application No. 13/745,742, filed on Jan. 18, 2013, and a continuation-in-part of application No. 13/794,467, filed on Mar. 11, 2013, now Pat. No. 9,132,113, which is a continuation of application No. 13/595,072, filed on Aug. 27, 2012, now abandoned, which is a continuation of application No. 12/023,753, filed on Jan. 31, 2008, now abandoned.

(60) Provisional application No. 61/588,162, filed on Jan. 18, 2012, provisional application No. 61/588,165, filed on Jan. 18, 2012, provisional application No. 61/588,167, filed on Jan. 18, 2012, provisional application No. 60/898,810, filed on Jan. 31, 2007, provisional application No. 61/588,165, filed on Jan. 18, 2013, provisional application No. 61/588,167, filed on Jan. 18, 2012, provisional application No. 60/898,810, filed on Jan. 31, 2007.

(51) Int. Cl.
| | | |
|---|---|---|
| A61K 31/23 | (2006.01) | |
| A61K 31/21 | (2006.01) | |
| A61K 31/235 | (2006.01) | |
| A61K 31/225 | (2006.01) | |
| A61K 45/06 | (2006.01) | |
| A61K 31/573 | (2006.01) | |
| A61K 31/603 | (2006.01) | |
| A61K 31/22 | (2006.01) | |
| A61K 31/216 | (2006.01) | |
| A61K 31/381 | (2006.01) | |
| A61K 31/55 | (2006.01) | |

(52) U.S. Cl.
CPC .......... *A61K 31/225* (2013.01); *A61K 31/216* (2013.01); *A61K 31/22* (2013.01); *A61K 31/381* (2013.01); *A61K 31/55* (2013.01); *A61K 31/573* (2013.01); *A61K 31/603* (2013.01); *A61K 45/06* (2013.01)

(58) Field of Classification Search
CPC .... A61K 31/216; A61K 31/22; A61K 31/381; A61K 31/55; A61K 31/225; A61K 31/573; A61K 31/603; A61K 45/06
See application file for complete search history.

(56) References Cited

U.S. PATENT DOCUMENTS

| | | | |
|---|---|---|---|
| 6,063,814 | A | 5/2000 | Chang et al. |
| 6,080,784 | A | 6/2000 | Driedger et al. |
| 6,184,248 | B1 | 2/2001 | Lee et al. |
| 6,268,395 | B1 | 7/2001 | Hattori |
| 2007/0009529 | A1 | 1/2007 | Karpatkin |
| 2007/0066684 | A1 | 3/2007 | Mori et al. |
| 2008/0226589 | A1 | 9/2008 | Han |
| 2011/0034425 | A1 | 2/2011 | Strair |
| 2011/0243917 | A1 | 10/2011 | Cheong et al. |
| 2011/0245307 | A1 | 10/2011 | Alkon |

FOREIGN PATENT DOCUMENTS

| | | |
|---|---|---|
| CN | 101667542 | 3/2010 |
| CN | 101677542 | 3/2010 |
| EP | 1230925 | 8/2002 |

(Continued)

OTHER PUBLICATIONS

Office Action for Chinese Application No. 2013-8001494.X dated Nov. 8, 2016.

(Continued)

*Primary Examiner* — Savitha Rao
(74) *Attorney, Agent, or Firm* — Sughrue Mion, PLLC

(57) ABSTRACT

Methods and compositions containing a phorbol ester or a derivative of a phorbol ester are provided for the treatment of chronic and acute conditions. Such conditions may be caused by disease, be symptoms or sequelae of disease. Chronic and acute conditions may be due to viral infections such as HIV and AIDS, neoplastic diseases stroke, kidney disease, urinary incontinence, autoimmune disorders, Parkinson's disease, prostate hypertrophy, aging, or the treatment of such diseases. Additional compositions and methods are provided which employ a phorbol ester or derivative compound in combination with at least one additional agent to yield more effective treatment tools against acute and chronic conditions in mammalian subjects.

9 Claims, No Drawings

(56) References Cited

FOREIGN PATENT DOCUMENTS

| | | |
|---|---|---|
| EP | 1589026 | 10/2005 |
| EP | 2030631 | 3/2009 |
| EP | 2170053 | 4/2010 |
| EP | 2368555 | 9/2011 |
| JP | 2001131075 | 5/2001 |
| JP | 2005179201 | 7/2005 |
| JP | 2008069182 | 3/2008 |
| SG | 11201404211 Y | 7/2014 |
| WO | 9118595 | 12/1991 |
| WO | 9202484 | 2/1992 |
| WO | 9814186 | 4/1998 |
| WO | 0182927 | 11/2001 |
| WO | 0209700 | 2/2002 |
| WO | 2004028516 | 4/2004 |
| WO | 2004103360 | 12/2004 |
| WO | 2005090349 | 9/2005 |
| WO | 2007009055 | 1/2007 |
| WO | 2008024490 | 2/2008 |
| WO | 2008094657 | 8/2008 |
| WO | 2009027087 | 3/2009 |
| WO | 2011127288 | 10/2011 |
| WO | 2011144901 | 11/2011 |
| WO | 2013110006 | 7/2013 |

OTHER PUBLICATIONS

Search Report for Chinese Application No. 2013-8001494.X dated Oct. 28, 2016.
Albrecht et al., "Chapter 44 Effects on Cells," In Baron S, editor. Medical Microbiology, 4th edition. Galveston (TX): University of Texas Medical Branch at Galveston; 1996 (Available from: http://www.ncbi.nlm.nih.gov/books/NBK7979/).
Allouche et al., "Effect of phorbol myristate acetate on T cell colony formation, interleukin-2 (IL-2) receptor expression and IL-2 production by cells from patients at all stages of HIV infection," Clinical and Experimental Immunology, 81(2):200-206 (1990).
Ardizzoni et al.., "Cisplatin- Versus Carboplatin-Based Chemotherapy in First-Line Treatment of Advanced Non-Small-Cell Lung Cancer: An Individual Patient Data Meta-analysis", J. Natl. Cancer Inst., 99:847-857 (2007).
Amarenco et al., "Classification of Stroke Subtypes", Cerebrovascular Disease, 27:493-501 (2009).
Blumberg, "Protein Kinase C as the Receptor for the Phorbol Ester Tumor Promoters: Sixth Rhoads Memorial Award Lecture," Cancer Res., 48:1-8 (1988).
Chowdhury et al., "The phorbol ester TPA strongly inhibits HIV-1-induced syncytia formation but enhances virus production: possible involvement of protein kinase C pathway", Virology, 176(1):126-132 (1990).
Clemens et al., "The role of protein kinase C isoenzymes in the regulation of cell proliferation and differentiation," J. Cell Sci., 103:881-887 (1992).
Costin, "Cytopathic Mechanisms of HIV-1," Virology J., 4:100 (2007).
Crawford et al., "Chemotherapy-Induced Neutropenia: Risks, Consequences, and New Directions for its Management", Cancer, 100(2):228-237 (2004).
El-Mekkawy et al., "12-0-Acetylphorbol-13-decanoate potently inhibits cytopathic effects of human immunodeficiency virus type I (HIV-1), without activation of protein kinase C," Chem. Pharm. Bull., 47(9):1346-1347 (1999).
Ettmayer et al., "Lessons learned from marketed and investigational prodrugs," J. Med. Chem., 47(10):2393-2404 (2004).
Garzotto, et al., "Reversal of Radiation Resistance in LNCaP Cells by Targeting Apoptosis through Ceramide Synthase," Cancer Research, 59:5194-5201 (1999).
Guo et al., "ALDH2, protects against stroke by clearing 4-HNE", Cell Res p. 1-16 (2013).

Han et al., "Effect of intravenous infusions of 12-O-tetradecanoylphorbol-13-acetate (TPA) in patients with myelocytic leukemia: Preliminary studies on therapeutic efficacy and toxicity," PNAS, 95(9):5357-5361 (1998).
Harada et al., "Tumor promoter, TPA, enhances replication of HTLV-III/LAV," Virology, 154(2):249-258 (1986).
Johnson et al., Relationships between drug activity in NCI preclinical in vitro and in vivo models and early clinical trials, British Journal of Cancer, 84(10):1434-1431 (2001).
Mayo Clinic; htt;://www.mayoclinic.org/diseases-conditions/stroke/basics/complications/con-20042884 (Mar. 27, 2014).
Mayo Clinic; http://www.mayoclinic.org/diseases-conditions/parkinsons-disease/basics/symptoms/con-20048488 (Jun. 10, 2015).
Merriam-Webster (http://www.merriam-webster.com/dictionary/remission, accessed Oct. 13, 2015).
Morissette et al., "High-throughput crystallization: polymorphs, salts, co-crystals and solvates of pharmaceutical solids," Adv. Drug Del. Rev., 56:275-300 (2004).
Muller et al., "Phorbol ester-induced synaptic facilitation is different than long-term potentiation," Proc. Natl. Acad. Sci. USA, 85:6997-7000 (1988).
Myint et al., "Post-stroke seizure and post-stroke epilepsy", Postgrad Med. J. 82:568-572 (2006).
National Cancer Institute, http://web.archive.org/web/20120828072825/http://cancer.gov/cancertropics/pdq/treatment/non-small-cell-lung/healthprofessional/page11, accessed Oct. 15, 2014, published Aug. 28, 2012.
Nelson et al, "Neuroprotective versus tumorigenic protein kinase C activators," Trends in Biochem. Sci., 34(3):136-145 (2009).
Newton, "Protein Kinase C: Structure, function, and regulation," J. Biol. Chem., 48 (270):28495-28498 (1995).
Pendelbury et al., "Stroke: management and prevention", Medicine, 32(10):62-69 (2004).
Niedle, Cancer Drug Design and Discovery, Elsevier/Academic Press, pp. 427-431 (2008); relevance p. 431.
Notification of the First Office Action for CN Application No. 201380014940.X dated Dec. 23, 2015 (with English Translation).
Pierelli et al., "Erythropoietin Additional to granulocyte colony-stimulating factor abrogates life-threating neutropenia and increases periopheral-blood progenitor-cell mobilization after epirubicin, paclitaxel, and cisplatin combination chemotherapy: results of a randomized comparison", Abstract, J. Clin. Oncol., 17(4):1288 (1999).
Sausville et al., "Contributions of Human Tumor Xenografts to Anticancer Drug Development", Cancer Res. 66:3351-3354 (2006).
Shimokawa, "Increased expression of endothelial lipase in rat models of hypertension", Cardiovascular Research, 66:594-600 (2005).
Smithgall, "Signal Transduction Pathways Regulating Hematopoietic Differentiation," Pharm. Rev., 50(1)1-19 (1998).
Stella, "Prodrugs as therapeutics," Expert Opin. Ther. Patents, 14(3):277-280 (2004).
Stevenson et al., "Inhibition of human immunodeficiency virus type 1-mediated cytopathic effects by poly(L-lysine)-conjugated synthetic antisense oligodeoxyribonucleotides," Journal of General Virology, 70(10):2673-2682 (1989).
Sun et al, "ALDH2, a novel target for endogenous neuroprotection against stroke?" Cell Res., pp. 1-2 (doi:10.1038/cr.2013.76) (online publication Jun. 2013).
Tahara et al., "Activation of protein kinase C by phorbol 12-myristate 13-acetate suppresses the growth of lung cancer cells through KLF6 induction", Cancer Biology & Therapy, 8(9):801-207 (2009).
Testa, "Prodrug research: futile or fertile?", Biochem. Pharm., 68:2097-2106 (2004).
Tian et al., Neural Regeneration Research, 5(20):1525 (2010).
Vippagunta et al., "Crystalline solids," Adv. Drug Del. Rev., 48:3-26 (2001).
Wang et al, "Prevention of Stroke and Myocardial Infraction by Amlodipine and Angiotensin Receptor Blockers: A Quantitative Overview", Hypertension, 50:181-188 (2007).

(56) References Cited

OTHER PUBLICATIONS

Webster, www.mariam-webster.com/dicitionary/remission, Definition of Remission, 2 pages, retrieved Feb. 25, 2016.
Wolff, Burger's Medicinal Chemistry and Drug Discovery, Fifth Edition vol. 1: Principles and Practice (John Wiley & Sons, Inc.), pp. 975-977 (1995).
Wolf, "Prevention of Stroke", The Lancet, 325(iii):15-18 (1998).
Yahr et al., Arch. Neurol., 21:343-354 (1969).
Youle et al., "Could chemoprophylaxis be used as an HIV prevention strategy while we wait for an effective vaccine?" AIDS, 17(16):937-938 (2003).
Zeidman et al., "Protein kinase C? actin-binding site is important for neurite outgrowth during neuronal differentiation," Molec. Biol. Cell, 13:2-24 (2002).
Zhong et al., "Novel phorbol esters exert dichotomous effects on inhibition of HIV-1 infection and activation of latent HIV-1 expression", Antiviral Chemistry and Chemotherapy, 16:303-313 (2005).
Han et al., "12-O-Tetradecanoylphorbol-13-acetate (TPA)-induced increase in depressed white blood cell counts in patients treated with cytotoxic cancer chemotherapeutic drugs," Proc. Natl. Acac. Sci. USA, 95:5362-5365 (1998).
Kim et al., "12-O-Tetradecanoyl phorbol-13-acetate (TPA)-induced growth arrest is increased by silibinin by the down-regulation of cyclin B1 and cdc2 and the up-regulation of p21 expression in MDA-MB231 human breast cancer cells", Phytomedicine, 17:1127-1132 (2010).
Xiao et al., "Phorbol Ester-Induced Apoptosis and Senescence In Cancer Cell Models", Method in Enzymology, 446:123-139 (2008).

COMPOSITIONS AND METHODS OF USE OF PHORBOL ESTERS

RELATED APPLICATIONS

This application is a (1) Continuation of U.S. application Ser. No. 14/027,320, filed Sep. 16, 2013 (now allowed); which is a Continuation-In-Part of U.S. application Ser. No. 13/745,740, filed Jan. 18, 2013; which claims benefit of U.S. Provisional Application Nos. 61/588,162, filed Jan. 18, 2012, 61/588,165, filed Jan. 18, 2012, and 61/588,167, filed Jan. 18, 2012, and is a Continuation-In-Part of Ser. No. 12/023,753, filed Jan. 31, 2008 (now abandoned); which claims benefit of U.S. Provisional Application No. 60/898,810, filed Jan. 31, 2007; (2) U.S. application Ser. No. 14/027,320, filed Sep. 16, 2013 (now allowed); is a Continuation-In-Part of U.S. application Ser. No. 13/745,745, filed Jan. 18, 2013 (now abandoned); which claims benefit of 61/558,165, filed Jan. 18, 2012; (3) U.S. application Ser. No. 14/027,320, filed Sep. 16, 2013 (now allowed); is a Continuation-In-Part of U.S. application Ser. No. 13/745,742, filed Jan. 18, 2013; which claims benefit of 61/588,167, filed Jan. 18, 2012; and (4) U.S. application Ser. No. 14/027,320, filed Sep. 16, 2013 (now allowed); is a Continuation-In-Part of U.S. application Ser. No. 13/794,467, filed Mar. 11, 2013 (now U.S. Pat. No. 9,132,113); which is a Continuation of U.S. application Ser. No. 13/595,072, filed Aug. 27, 2012 (now abandoned); which is a Continuation of Ser. No. 12/023,753, filed Jan. 31, 2008 (now abandoned); which claims benefit of 60/898,810, filed Jan. 31, 2007; the disclosure of each of which is incorporated herein in their entirety by reference.

TECHNICAL FIELD

The present invention relates generally to the medicinal use of phorbol esters.

BACKGROUND

Plants have historically served many medicinal purposes. The World Health Organization (WHO) estimates that 4 billion people, 80% of the world population, presently use herbal medicine for some aspect of primary health care. (WHO Fact sheet Fact sheet No 134 December 2008) However, it can be difficult to isolate the specific compound that has the medicinal effect and to reproduce it on a commercial scale. Additionally, while active compounds may be isolated from a plant, the other parts of a plant such as the minerals, vitamins, volatile oils, glycosides, alkaloids, bioflavanoids, and other substances may also be involved in the functioning of the active ingredient, or the medicinal effect for which the plant is known making the use, purification and commercialization of plant based pharmaceutical agents a challenge.

Phorbol is a natural, plant-derived organic compound of the tigliane family of diterpenes. It was first isolated in 1934 as a hydrolysis product of croton oil derived from the seeds of *Croton tiglium*, a leafy shrub of the Euphorbiaceae family that is native to Southeastern Asia. Various esters of phorbol have important biological properties including the reported ability to mimic diacylglycerols and activate protein kinase C (PKC), modulating downstream cell signaling pathways including the mitogen-activated protein kinase (MAPK) pathways. Phorbol esters are additionally thought to bind to chimaerins, the Ras activator RasGRP, and the vesicle-priming protein Munc-13 (Brose N, Rosenmund C., JCell Sci; 115:4399-411 (2002)). Some phorbol esters also induce nuclear factor-kappa B (NF-κB). The most notable physiological property of phorbol esters is their reported capacity to act as tumor promoters. (Blumberg, 1988; Goel, G et al., Int, Journal of Toxicology 26, 279-288 (2007)).

12-O-tetradecanoylphorbol-13-acetate (TPA), also called phorbol-12-myristate-13-acetate (PMA), is a phorbol ester used in models of carcinogenesis as an inducer for differentiation and/or apoptosis in multiple cell lines and primary cells. TPA has also been reported to cause an increase in circulating white blood cells and neutrophils in patients whose bone marrow function has been depressed by chemotherapy (Han Z. T. et al. Proc. Natl. Acad. Sci. 95, 5363-5365 (1998)) and inhibit the HIV-cytopathic effects on MT-4 cells. (Mekkawy S. et al., Phytochemistry 53, 47-464 (2000)). However, due to a variety of factors, including caustic reactions when contacted with the skin and concerns for its potential toxicity, TPA has not been shown to be an effective tool for treating, managing, or preventing HIV or AIDS or as an adjuvant to chemotherapy. Indeed, as phorbol esters play a key role in activation of protein kinase C (PKC), which triggers various cellular responses resulting in inflammatory responses and tumor development (Goel et al., Int, Journal of Toxicology 26, 279-288 (2007)), phorbol esters would generally be excluded from possible treatment candidates for cancer or inflammatory diseases such as rheumatoid arthritis or conditions that involve inflammatory reactions such as stroke, autoimmune disorders or prostate hypertrophy.

As modern medicine has developed, survival rates from both chronic and acute disease has increased, generating new challenges in managing both chronic conditions and the sequelae of acute disease and treatment side effects. There is a continuing need for the identification of pharmaceutical agents, including plant based pharmaceutical agents, which can be used to treat disease, prevent damage from acute episodes, manage the symptoms of disease conditions, and manage the side effects of disease treatments. While molecular targeting has produced a number of successful pharmaceutical agents, frequently multiple pathways of signaling are involved, and blocking one pathway can easily be compensated for elsewhere. There is clearly a need for new and more effective treatments and side effect management for individuals suffering from a variety of conditions, particularly chronic or potentially recurring conditions such as cancer, immune disorders, autoimmune disorders, stroke, rheumatoid arthritis, inflammation, uterine fibroids, prostate hypertrophy, urinary incontinence, Parkinson's disease and kidney disease.

SUMMARY

The present invention relates to compositions containing and methods of using phorbol esters. These compositions and methods are effective in treating chronic or potentially recurring conditions, or to repair the damage left by acute episodes of particular diseases.

In one embodiment, phorbol esters and derivatives of phorbol esters are used to treat diseases such as HIV and associated conditions such as AIDS. The compositions and methods of the present invention may accomplish the treatment of HIV and associated conditions such as AIDS by any means possible. In some embodiments, the compositions and methods may modify HIV receptor activity in mammalian subjects. In another embodiment, the compositions and methods as described herein may decrease the number of latent HIV reservoirs in an HIV-infected subject. In a further embodiment, the compositions and methods as described herein may enhance HIV activation in latent pro-viral cells. In additional embodiments, they may inhibit HIV-cytopathic effects.

In another embodiment, compositions containing phorbol esters and phorbol ester derivatives may be used for treating and managing symptoms of HIV and AIDS in mammalian subjects. Targeted symptoms for treatment and management employing the compositions and methods described herein include, but are not limited to, oral lesions, fatigue, skin thrush, fever, lack of appetite, diarrhea, apthous ulcers, malabsorbtion, thrombocytopenia, weight loss, anemia, lymph node enlargement, susceptibility to and severity of secondary conditions such as mycobacterium avium complex, salmonellosis, syphilis, neuroshyphilis, tuberculosis (TB), bacillary angiomatosis, aspergillosis, candidiasis, coccidioidomycosis, listeriosis, pelvic inflammatory disease, Burkitt's lymphoma, cryptococcal meningitis, histoplasmosis, Kaposi's sarcoma, lymphoma, systemic non-Hodgkin's lymphoma (NHL), primary CNS lymphoma, cryptosporidiosis, isosporiasis, microsporidiosis, pneumocystis carinii pneumonia (PCP), toxoplasmosis, cytomegalovirus (CMV), hepatitis, herpes simplex, herpes zoster, human papiloma virus (HPV, genital warts, cervical cancer), molluscum contagiosum, oral hairy leukoplakia (OHL), and progressive multifocal leukoencephalopathy (PML).

In a further embodiment, compounds containing phorbol esters and derivatives of phorbol esters may be used to treat neoplastic diseases. Such neoplasms may be malignant or benign. In some embodiments, neoplasms may be solid or non-solid cancers. In other embodiments, the neoplasms may be relapses. In another embodiment, the neoplasm may be refractory. Exemplary neoplasms include, but are not limited to, hematologic malignancies/bone marrow disorders, including, but not limited to, leukemia, including acute myeloid leukemia (AML), chronic myeloid leukemia (CML), chronic myeloid leukemia blast crisis, myelodysplasia, and myeloproliferative syndrome; lymphoma, including Hodgkin's and non-Hodgkin's lymphoma; subcutaneous adenocarcinoma; ovarian teratocarcinoma; liver cancer; breast cancer; bone cancer; lung cancer; pancreatic, non-small cell lung cancer and prostate cancer. Other neoplastic conditions amenable to treatment using the methods and compositions as described herein include other cancer disorders and conditions, including solid tumors of various types. Successful treatment and/or remission will be determined according to conventional methods, such as determining size reduction of solid tumors, and/or histopathological studies to assess growth, stage, metastatic state or potential, presence or expression levels of histological cancer markers, etc.

Compositions and methods herein may additionally be used treat symptoms of neoplastic disease including, but not limited to, anemia; chronic fatigue; excessive or easy bleeding, such as bleeding of the nose, gums, and under the skin; easy bruising, particularly bruising with no apparent cause; shortness of breath; petechiae; recurrent fever; swollen gums; slow healing of cuts; bone and joint discomfort; recurrent infections; weight loss; itching; night sweats; lymph node swelling; fever; abdominal pain and discomfort; disturbances in vision; coughing; loss of appetite; pain in the chest; difficulty swallowing; swelling of the face, neck and upper extremities; a need to urinate frequently, especially at night; difficulty starting urination or holding back urine; weak or interrupted flow of urine; painful or burning urination; difficulty in having an erection; painful ejaculation; blood in urine or semen; frequent pain or stiffness in the lower back, hips, or upper thighs; and weakness.

Compositions and methods herein may further be used to treat the side effects of chemotherapy and radiation therapy which are commonly used as treatments for neoplastic disease. Such side effects include, but not limited to, alopecia, nausea, vomiting, poor appetite, soreness, neutropenia, anemia, thrombocytopenia, dizziness, fatigue, constipation, oral ulcers, itchy skin, peeling, nerve and muscle damage, auditory changes, weight loss, diarrhea, immunosuppression, bruising, heart damage, bleeding, liver damage, kidney damage, edema, mouth and throat sores, infertility, fibrosis, epilation, moist desquamation, mucosal dryness, vertigo and encephalopathy.

In yet another embodiment, the phorbol esters and derivatives of phorbol esters as described herein may be used to modulate cell signaling pathways. Such modulation may have a variety of results, for example, in some embodiments, the use of compositions containing phorbol esters and derivatives of phorbol esters may increase white blood cell counts in mammalian subjects. In another embodiment, compositions containing phorbol esters and/or phorbol ester derivatives may alter the release of Th1 cytokines in mammalian subjects. In a further embodiment, compositions containing phorbol esters and/or phorbol ester derivatives may alter the release of interleukin 2 (IL-2) in mammalian subjects. In an additional embodiment, compositions containing phorbol esters and/or phorbol ester derivatives may alter the release of interferon in mammalian subjects. In yet another embodiment, compositions containing phorbol esters and/or phorbol ester derivatives may alter the rate of ERK phosphorylation.

In a further embodiment, the phorbol esters and derivatives of phorbol esters as described herein may be used in the prevention and treatment of stroke and damage due to stroke. Effects of stroke that may be prevented or treated by using the phorbol esters and derivatives of phorbol esters as described herein include, but are not limited to, paralysis, spatial impairment, impaired judgment, left-sided neglect, memory loss, aphasia, coordination and balance problems, nausea, vomiting, cognitive impairment, perception impairment, orientation impairment, homonymous hemianopsia and impulsivity.

In yet another embodiment, the phorbol esters and derivatives of phorbol esters as described herein may be used in the treatment of rheumatoid arthritis. Symptoms of rheumatoid arthritis that may be prevented or treated by the phorbol esters and derivatives of phorbol esters as described herein include, but are not limited to, sore joints, morning stiffness, firm bumps of tissue under the skin of the arms, fatigue, loss of energy, lack of appetite, low-grade fever or muscle and joint aches.

In additional embodiments, the phorbol esters and derivatives of phorbol esters as described herein may be used in the treatment of prostate hypertrophy. The compositions and methods as described herein may be used to prevent or treat symptoms of prostate hypertrophy including, but not limited to, dribbling at the end of urination, urinary retention, incomplete emptying of the bladder, incontinence, excessive urinary frequency, pain with urination, bloody urine, delayed urination, straining to urinate, weak urine stream or strong and sudden urge to urinate.

In a further embodiment, the phorbol esters and derivatives of phorbol esters as described herein may be used in the treatment of kidney disease.

In an additional embodiment, the phorbol esters and derivatives of phorbol esters as described herein may be used in the treatment of urinary incontinence.

In another embodiment, the phorbol esters and derivative of phorbol esters as described herein may be used in the treatment of uterine fibroids.

In another embodiment, the phorbol esters and derivative of phorbol esters as described herein may be used in the treatment of dementia.

In another embodiment, the phorbol esters and derivative of phorbol esters as described herein may be used in the treatment of diabetes.

In an embodiment, the phorbol esters and derivatives of phorbol esters as described herein may be used to decrease visible signs of aging in individuals.

In an additional embodiment, the phorbol esters and derivatives of phorbol esters as described herein may be used to decrease swelling around the eyes.

In a further embodiment, the phorbol esters and derivatives of phorbol esters as described herein may be used in the treatment of autoimmune disorders including, but not limited to, myasthenia gravis. Symptoms of myasthenia gravis that may be prevented or treated by use of the compositions and methods described herein include, but are not limited to, ptosis, diplopia, speech impairment, fatiguability, muscle weakness, dysphagia or dysarthria.

In an additional embodiment, the phorbol esters and derivatives of phorbol esters as described herein may be used in the treatment and prevention of central nervous system disorders such as Parkinson's disease. Symptoms of Parkinson's disease that may be treated or prevented by the use of the compositions and methods described herein include, but are not limited to, tremor at rest, stiffness, bradykinesia, rigidity, speech impairment, cognitive impairment, dementia, mood impairment, drowsiness, insomnia and postural instability.

In yet another embodiment, the phorbol esters and derivatives of phorbol esters as described herein may be used in the treatment and prevention of carpal tunnel syndrome.

The invention achieves the foregoing and satisfies additional objects and advantages by providing novel and surprisingly effective methods and compositions for modulating cell signaling pathways and/or treating diseases and symptoms of diseases or conditions using compositions containing a phorbol ester or derivative composition of the Formula I, below:

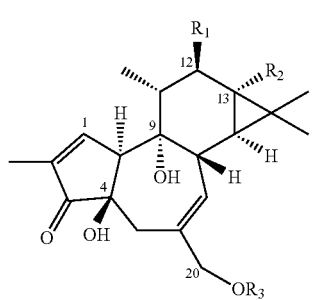

Formula I wherein $R_1$ and $R_2$ may be hydrogen; hydroxyl,

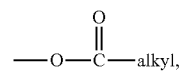

wherein the alkyl group contains 1 to 15 carbon atoms;

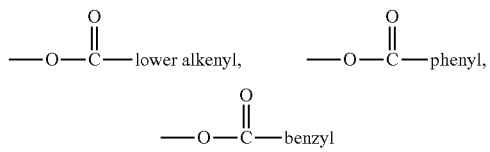

and substituted derivatives thereof and $R_3$ may be hydrogen or

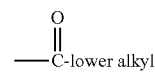

and substituted derivatives thereof.

In some embodiments, at least one of $R_1$ and $R_2$ are other than hydrogen and $R_3$ is hydrogen or

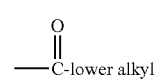

and substituted derivatives thereof. In another embodiment, either $R_1$ or $R_2$ is

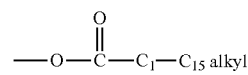

the remaining $R_1$ or $R_2$ is

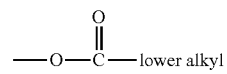

and $R_3$ is hydrogen.

The alkyl, alkenyl, phenyl and benzyl groups of the formulas herein may be unsubstituted or substituted with halogens, preferably, chlorine, fluorine or bromine; nitro; amino; and/or similar type radicals.

In a further embodiment, the invention achieves these objects and satisfies additional objects and advantages by providing novel and surprisingly effective methods and compositions for modulating cell signaling pathways and/or treating diseases or conditions associated with diseases using an exemplary phorbol ester composition such as 12-O-tetradecanoylphorbol-13-acetate (TPA) of Formula II, below:

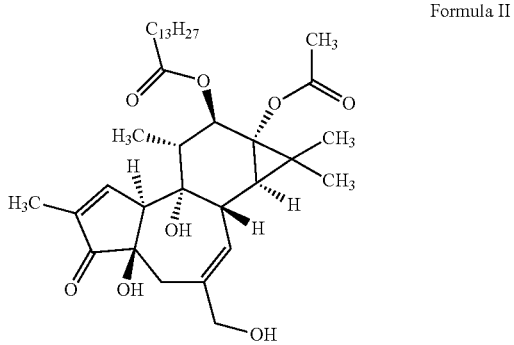

Formula II

Useful phorbol esters and related compounds and derivatives within the formulations and methods of the invention include, but are not limited to, other pharmaceutically acceptable active salts of said compounds, as well as active isomers, enantiomers, polymorphs, glycosylated derivatives, solvates, hydrates, and/or prodrugs of said compounds. Exemplary forms of phorbol esters for use within the compositions and methods of the invention include, but are not limited to, phorbol 13-butyrate; phorbol 12-decanoate; phorbol 13-decanoate; phorbol 12,13-diacetate; phorbol 13,20-diacetate; phorbol 12,13-dibenzoate; phorbol 12,13-dibutyrate; phorbol 12,13-didecanoate; phorbol 12,13-dihexanoate; phorbol 12,13-dipropionate; phorbol 12-myristate; phorbol 13-myristate; phorbol 12-myristate-13-acetate (also known as TPA or PMA); phorbol 12,13,20-triacetate; 12-deoxyphorbol 13-angelate; 12-deoxyphorbol 13-angelate 20-acetate; 12-deoxyphorbol 13-isobutyrate; 12-deoxyphorbol 13-isobutyrate-20-acetate; 12-deoxyphorbol 13-phenylacetate; 12-deoxyphorbol 13-phenylacetate 20-acetate; 12-deoxyphorbol 13-tetradecanoate; phorbol 12-tigliate 13-decanoate; 12-deoxyphorbol 13-acetate; phorbol 12-acetate; and phorbol 13-acetate.

Mammalian subjects amenable to treatment with phorbol esters of Formula I, particularly TPA, according to the methods of the invention include, but are not limited to, subjects with HIV and AIDS, as well as subjects with symptoms, or secondary or opportunistic diseases associated with HIV and AIDS, such as oral lesions, fatigue, skin thrush, fever, lack of appetite, diarrhea, apthous ulcers, malabsorption, thrombocytopenia, weight loss, anemia, lymph node enlargement, mycobacterium avium complex, salmonellosis, syphilis, neuroshyphilis, tuberculosis (TB), bacillary angiomatosis, aspergillosis, candidiasis, coccidioidomycosis, listeriosis, pelvic inflammatory disease, Burkitt's lymphoma, cryptococcal meningitis, histoplasmosis, Kaposi's sarcoma, lymphoma, systemic non-Hodgkin's lymphoma (NHL), primary CNS lymphoma, cryptosporidiosis, isosporiasis, microsporidiosis, pneumocystis carinii pneumonia (PCP), toxoplasmosis, cytomegalovirus (CMV), hepatitis, herpes simplex, herpes zoster, human papiloma virus (HPV, genital warts, cervical cancer), molluscum contagiosum, oral hairy leukoplakia (OHL), and progressive multifocal leukoencephalopathy (PML).

Additional mammalian subjects amenable to treatment with phorbol esters of Formula I, particularly TPA, according to the methods of the present invention include, but are not limited to, subjects suffering from neoplastic diseases including malignant neoplastic diseases such as solid and non-solid cancers. Non-solid cancers may include, hematologic malignancies/bone marrow disorders, including, but not limited to, leukemia, including acute myeloid leukemia (AML), chronic myeloid leukemia (CML), chronic myeloid leukemia blast crisis, myelodysplasia, myeloproliferative syndrome. Solid cancers may include, but are not limited to, lymphoma, including Hodgkin's and non-Hodgkin's lymphoma, subcutaneous adenocarcinoma, ovarian teratocarcinoma, lung cancer; bone cancer; breast cancer; liver cancer; pancreatic cancer; oral cancer; non-small cell lung cancer and prostate cancer.

Subjects amenable to treatment with phorbol esters of Formula I, particularly TPA, further include those suffering from symptoms of such neoplastic diseases such as, but not limited to, anemia; chronic fatigue; excessive or easy bleeding, such as bleeding of the nose, gums, and under the skin; easy bruising, particularly bruising with no apparent cause; shortness of breath; petechiae; recurrent fever; swollen gums; slow healing of cuts; bone and joint discomfort; recurrent infections; weight loss; itching; night sweats; lymph node swelling; fever; abdominal pain and discomfort; disturbances in vision; coughing; loss of appetite; pain in the chest; difficulty swallowing; swelling of the face, neck and upper extremities; a need to urinate frequently, especially at night; difficulty starting urination or holding back urine; weak or interrupted flow of urine; painful or burning urination; difficulty in having an erection; painful ejaculation; blood in urine or semen; frequent pain or stiffness in the lower back, hips, or upper thighs; and weakness. In some embodiments, such cancers may be relapses or refractory.

Further mammalian subjects that are amenable to treatment with phorbol esters of Formula I, particularly TPA, according to the methods of the present invention include, but are not limited to, subjects suffering from side effects of chemotherapy or radiation therapy for the treatment of neoplastic diseases including malignant neoplastic diseases such as solid and non-solid cancers. Such side effects include, but are not limited to alopecia, nausea, vomiting, poor appetite, soreness, neutropenia, anemia, thrombocytopenia, dizziness, fatigue, constipation, oral ulcers, itchy skin, peeling, nerve and muscle damage, auditory changes, weight loss, diarrhea, immunosuppression, bruising, heart damage, bleeding, liver damage, kidney damage, edema, mouth and throat sores, infertility, fibrosis, epilation, and moist desquamation, mucosal dryness, vertigo and encephalopathy.

Additional mammalian subjects, including humans, amenable to treatment with phorbol esters of Formula I, particularly TPA, according to the methods and compositions of the present invention include, but are not limited to individuals who have suffered a stroke. Subjects amenable to treatment with phorbol esters of Formula I, particularly TPA, additionally include those suffering from the effects of a stroke including, but not limited to, paralysis, spatial impairment, impaired judgment, left-sided neglect, memory loss, aphasia, coordination and balance problems, nausea, vomiting, cognitive impairment, perception impairment, orientation impairment, homonymous hemianopsia and impulsivity.

Other mammalian subjects, including humans, amenable to treatment with phorbol esters of Formula I, particularly TPA, according to the methods of the present invention, include individuals suffering from rheumatoid arthritis. Symptoms of rheumatoid arthritis that may be prevented or treated by the phorbol esters of Formula I, particularly TPA, include, but are not limited to, sore joints, morning stiffness, firm bumps of tissue under the skin of the arms, fatigue, loss of energy, lack of appetite, low-grade fever or muscle and joint aches.

Additional mammalian subjects, including humans, amenable to treatment with phorbol esters of Formula I, particularly TPA, according to the methods of the present invention, include individuals suffering from prostate hypertrophy. The compositions and methods as described herein may be used to prevent or treat symptoms of prostate hypertrophy including, but not limited to, dribbling at the end of urination, urinary retention, incomplete emptying of the bladder, incontinence, excessive urinary frequency, pain with urination, bloody urine, delayed urination, straining to urinate, weak urine stream or strong and sudden urge to urinate.

Further mammalian subjects, including humans, amenable to treatment with phorbol esters of Formula I, particularly TPA, according to the methods of the present invention include individuals suffering from kidney disease.

Further mammalian subjects, including humans, amenable to treatment with phorbol esters of Formula I, particularly TPA, according to the methods of the present invention include individuals suffering from urinary incontinence.

Additional mammalian subjects, including humans, amenable to treatment with phorbol esters of Formula I, particularly TPA, according to the methods of the present invention include individuals with visible signs of aging.

Other mammalian subjects, including humans, amenable to treatment with phorbol esters of Formula I, particularly TPA, according to the methods of the present invention include individuals with swelling around the eyes.

Additional mammalian subjects, including humans, amenable to treatment with phorbol esters of Formula I, particularly TPA, according to the methods of the present invention include individuals with uterine fibroids.

Additional mammalian subjects, including humans, amenable to treatment with phorbol esters of Formula I, particularly TPA, according to the methods of the present invention include individuals with dementia.

Additional mammalian subjects, including humans, amenable to treatment with phorbol esters of Formula I, particularly TPA, according to the methods of the present invention include individuals with diabetes.

Further mammalian subjects, including humans, amenable to treatment with phorbol esters of Formula I, particularly TPA, according to the methods of the present invention include those suffering from autoimmune disorders including, but not limited to, myasthenia gravis. Symptoms of myasthenia gravis that may be prevented or treated by use of the compositions and methods described herein include, but are not limited to, ptosis, diplopia, speech impairment, fatiguability, muscle weakness, dysphagia or dysarthria.

Additional mammalian subjects, including humans, amenable to treatment with phorbol esters of Formula I, particularly TPA, according to the methods of the present invention include individuals with Parkinson's disease. Symptoms of Parkinson's disease that may be treated or prevented by the use of the compositions and methods described herein include, but are not limited to, tremor at rest, stiffness, bradykinesia, rigidity, speech impairment, cognitive impairment, dementia, mood impairment, drowsiness, insomnia and postural instability.

In yet another embodiment, mammalian subjects with carpal tunnel syndrome may be treated with phorbol esters of Formula I, particularly TPA, according to the methods of the present invention.

These and other subjects are effectively treated, prophylactically and/or therapeutically, by administering to the subject an effective amount of a phorbol ester of Formula I sufficient to prevent or reduce viral load, decrease latent reservoirs of HIV, increase immune responsiveness, increase the release of Th1 cytokines, prevent or reduce symptoms and conditions associated with HIV and AIDS, decrease and/or eliminate neoplastic cells, increase white blood cell counts, induce remission, maintain remission, prevent or reduce symptoms and conditions associated with malignancies, increase ERK phosphorylation, decrease or eliminate radiation damage, boost the immune system, decrease nausea, decrease or prevent hair loss, increase appetite, decrease soreness, increase energy levels, relieve gastrointestinal distress, decrease bruising, eliminate oral ulcers, decrease or eliminate skin damage due to radiation, increase or maintain neutrophil levels, increase or maintain platelet levels, decrease edema, decrease or eliminate moist desquamation, prevent or treat paralysis, increase spatial awareness, decrease memory loss, decrease aphasia, increase coordination and balance, improve cognition, decrease or eliminate tremors, decrease or eliminate stiffness and rigidity, improve sleep quality, increase stability, improve mobility, improve bladder control, improve appetite, ease muscle or joint aches, improve vision, and/or improve muscle control.

Therapeutically useful methods and formulations of the invention will effectively use a phorbol ester of Formula I in a variety of forms, as noted above, including any active, pharmaceutically acceptable salts of said compounds, as well as active isomers, enantiomers, polymorphs, solvates, hydrates, prodrugs, and/or combinations thereof. TPA of formula II is employed as an illustrative embodiment of the invention within the examples herein below.

Within additional aspects of the invention, combinatorial formulations and methods are provided which employ an effective amount of a phorbol ester of Formula I in combination with one or more secondary or adjunctive active agent(s) that is/are combinatorially formulated or coordinately administered with the phorbol ester compound of Formula I to yield an effective response in the subject.

Exemplary combinatorial formulations and coordinate treatment methods in the treatment of viral cytopathic diseases such as HIV and AIDS employ the phorbol ester compound of Formula I in combination with one or more additional, retroviral, HIV or AIDS treating or other indicated secondary or adjunctive therapeutic agents. Such combinatorial formulations and coordinate treatment methods may, for example, follow or be derived from various highly active antiretroviral therapy protocols (HAART protocols) and include regimens such as, but not limited to, two nucleoside analogue reverse transcriptase inhibitors plus one or more protease inhibitor or non-nucleoside analogue reverse transcriptase inhibitor among other combinations. Other combinatorial formulations and coordinate treatment methods may, for example, include treatments for opportunistic infections as well as the compounds for the HAART protocols. The secondary or adjunctive therapeutic agents used in combination with a phorbol ester, e.g., TPA, in these embodiments may possess direct or indirect antiviral effects, alone or in combination with, e.g. TPA; may exhibit other useful adjunctive therapeutic activity in combination with a phorbol ester, e.g. TPA (such as HIV preventing, HIV treating, HIV reservoir activating, Th1 cytokine increasing activity); or may exhibit adjunctive therapeutic activity useful for treating opportunistic infections associated with HIV alone or in combination with a phorbol ester, e.g. TPA.

Useful adjunctive therapeutic agents in these combinatorial formulations and coordinate treatment methods include, for example, protease inhibitors, including, but not limited to, saquinavir, indinavir, ritonavir, nelfinavir, atazanavir, darunavir, fosamprenavir, tipranavir and amprenavir; nucleoside reverse transcriptase inhibitors including but not limited to, zidovudine, didanosine, stavudine, lamivudine, zalcitabine, emtricitabine, tenofovir disoproxil fumarate, AVX754 and abacavir; non-nucleoside reverse transcriptase inhibitors including, but not limited to, nevaripine, delavirdine, calanolide A, TMC125 and efavirenz; combination drugs including, but not limited to, efavirenz/emtricitabine/tenofovir disoproxil fumarate, lamivudine/zidovudine, abacavir/lamivudine, abacavir/lamivudine/zidovudine, emtricitabine/tenofovir disoproxil fumarate, sulfamethoxazole/trimethoprim, and lopinavir/ritonavir; entry and fusion inhibitors, including, but not limited to, enfuvirtide, AMD070, BMS-488043, fozivudine tidoxil, GSK-873,140, PRO 140, PRO 542, Peptide T, SCH-D, TNX-355, and UK-427,857; treatments for opportunistic infections and other conditions associated with AIDS and HIV including, but not limited to, acyclovir, adefovir dipivoxil, aldesleukin, amphotericin b, azithromycin, calcium hydroxylapatite, clarithromycin, doxorubicin, dronabinol, entecavir, epoetin alfa, etoposide, fluconazole, ganciclovir, immunoglobulins, interferon alfa-2, isoniazid, itraconazole, megestrol, paclitaxel, peginterferon alfa-2, pentamidine, poly-1-lactic acid, ribavirin, rifabutin, rifampin, somatropin, testosterone, trimetrexate, and valganciclovir; integrase inhibitors including, but not limited to, GS 9137, MK-0518; microbicides, including, but not limited to, BMS-378806, C31G, carbopol 974P, carrageenan, cellulose sulfate, cyanovirin-N, dextran sulfate, hydroxyethyl cellulose, PRO 2000, SPL7013, tenofovir, UC-781 and IL-2.

Exemplary combinatorial formulations and coordinate treatment methods in the treatment of neoplastic disease employ a phorbol ester compound of Formula I in combination with one or more additional, neoplastic disease treating or other indicated, secondary or adjunctive therapeutic agents. The secondary or adjunctive therapeutic agents used in combination with a phorbol ester, e.g., TPA, in these embodiments may possess direct or indirect chemotherapeutic effects, alone or in combination with, e.g. TPA; may exhibit other useful adjunctive therapeutic activity in combination with a phorbol ester, e.g. TPA (such as cytotoxic, anti-inflammatory, NF-κB inhibiting, apoptosis inducing, Th1 cytokine increasing activity); or may exhibit adjunctive therapeutic activity useful for treating neoplasms or associated symptoms alone or in combination with, e.g. TPA.

Useful adjunctive or secondary therapeutic agents in these combinatorial formulations and coordinate treatment methods for the treatment of neoplastic diseases include doxorubicin, vitamin D3, cytarabine, cytosine arabinoside, daunorubicin, cyclophosphamide, gemtuzumab ozogamicin, idarubicin, mercaptopurine, mitoxantrone, thioguanine, aldesleukin, asparaginase, carboplatin, etoposide phosphate, fludarabine, methotrexate, etoposide, dexamethasone, and choline magnesium trisalicylate. In addition, adjunctive or secondary therapies may be used such as, but not limited to, radiation treatment, hormone therapy and surgery.

Exemplary combinatorial formulations and coordinate treatment methods in the prevention or treatment of side effects from chemotherapy employ a phorbol ester compound of Formula I in combination with one or more additional, chemoprotective or other indicated, secondary or adjunctive therapeutic agents. The secondary or adjunctive therapeutic agents used in combination with the phorbol ester, e.g., TPA, in these embodiments may possess direct or indirect chemoprotective effects, alone or in combination with the phorbol ester, e.g. TPA; may exhibit other useful adjunctive therapeutic activity in combination with a phorbol ester, e.g. TPA (such as anti-inflammatory, neutrophil stimulating, erythropoiesis stimulating, bone resorption inhibiting, bone strengthening, antiemetic, pain relieving); or may exhibit adjunctive therapeutic activity useful for treating or preventing side effects of chemotherapy or associated symptoms alone or in combination with a phorbol ester, e.g. TPA.

Useful adjunctive or secondary therapeutic agents in these combinatorial formulations and coordinate treatment methods for the prevention or treatment of side effects of chemotherapy in a mammalian subject include, but are not limited to, pegfilgrastim, epoeitn alfa, darbepoetin alfa, alendronate sodium, risedronate, ibandronate, G-CSF, 5-HT$_3$ receptor antagonists, NK$_1$ antagonists, olanzapine, corticosteroids, dopamine antagonists, serotonin antagonists, benzodiazepines, aprepitant, and cannabinoids.

Exemplary combinatorial formulations and coordinate treatment methods in the prevention or treatment of side effects from radiation therapy as contemplated herein employ a phorbol ester compound of Formula I in combination with one or more additional, radiation protective or other indicated, secondary or adjunctive therapeutic agents. The secondary or adjunctive therapeutic agents used in combination with a phorbol ester e.g., TPA, in these embodiments may possess direct or indirect protection from radiation damage, alone or in combination with a phorbol ester, e.g. TPA; may exhibit other useful adjunctive therapeutic activity in combination with the phorbol ester, e.g. TPA (such as anti-swelling, cytoprotective, anti-mucositis, epithelial stimulating, anti-fibrotic, platelet stimulating); or may exhibit adjunctive therapeutic activity useful for treating or preventing side effects of radiation therapy or associated symptoms alone or in combination with, e.g. TPA.

Useful adjunctive or secondary therapeutic agents in these combinatorial formulations and coordinate treatment methods for the prevention or treatment of side effects of radiation therapy in a mammalian subject include, but are not limited to, steroids, amifostine, chlorhexidine, benzydamine, sucralfate, keratinocyte growth factor (KGF), palifermin, Cu/Zn superoxide dismutase, Interleukin 11, or prostaglandins.

Exemplary combinatorial formulations and coordinate treatment methods in the treatment of stroke employ a phorbol ester compound of Formula I in combination with one or more additional, stroke preventing, treating or other indicated, secondary or adjunctive therapeutic agents. The secondary or adjunctive therapeutic agents used in combination with a phorbol ester, e.g., TPA, in these embodiments may possess direct or indirect effects on prevention or recovery from stroke, alone or in combination with the phorbol ester, e.g. TPA; may exhibit other useful adjunctive therapeutic activity in combination with, e.g. TPA (such as anti-clotting, anticholesterolemic, vasodilating, antihypertensive); or may exhibit adjunctive therapeutic activity useful for treating or preventing stroke or associated symptoms alone or in combination with, e.g. TPA.

Useful adjunctive or secondary therapeutic agents in these combinatorial formulations and coordinate treatment methods for the prevention or treatment of stroke in a mammalian subject include, but are not limited to, tissue plasminogen activator, anticoagulant, statin, angiotensin II receptor blockers, angiotensin-converting enzyme inhibitor, beta-blocker, calcium channel blocker, or diuretic. In addition, adjunctive or secondary therapies may be used such as, but not limited to, carotid endarterectomy, angioplasty, stent placement, craniotomy, endovascular coil emobilization, or patent foramen ovale closure.

Exemplary combinatorial formulations and coordinate treatment methods in the treatment of Parkinson's disease employ the phorbol ester compound of Formula I in combination with one or more additional, Parkinson's disease treating or other indicated, secondary, or adjunctive therapeutic agents. The secondary or adjunctive therapeutic agents used in combination with a phorbol ester, e.g., TPA, in these embodiments may possess direct or indirect anti-Parkinsonian effects, alone or in combination with, e.g. TPA; may exhibit other useful adjunctive therapeutic activity in combination with, e.g. TPA (dopamine increasing, catechol-O-methyl transferase inhibiting, aromatic L-amino acid decarboxylase inhibiting, dopamine agonist, neuroprotective, anticholinergic); or may exhibit adjunctive therapeutic activity useful for treating or preventing side effects of chemotherapy or associated symptoms alone or in combination with, e.g. TPA.

Useful adjunctive or secondary therapeutic agents in these combinatorial formulations and coordinate treatment methods for the prevention or treatment of symptoms of Parkinson's disease in a mammalian subject include, but are not limited to, levodopa, tolcapone, carbidopa, dopamine agonist, MAO-B inhibitors, pyridoxine, amantidine, pyridoxine, seleyiline, rasagiline, or anticholinergics. In addition, adjunctive or secondary therapies may be used such as, but not limited to, deep brain stimulation or lesion formation.

Exemplary combinatorial formulations and coordinate treatment methods in the treatment of prostate hypertrophy employ a phorbol ester compound of Formula I in combination with one or more additional, prostate hypertrophy treating or other indicated, secondary or adjunctive therapeutic agents. The secondary or adjunctive therapeutic agents used in combination with a phorbol ester, e.g., TPA, in these embodiments may possess direct or indirect effects, alone or in combination; may exhibit other useful adjunctive therapeutic activity in combination with, e.g. TPA (type II 5-alpha reductase inhibitor, muscle relaxant); or may exhibit adjunctive therapeutic activity useful for treating or preventing prostate hypertrophy or associated symptoms alone or in combination with, e.g. TPA.

Useful adjunctive or secondary therapeutic agents in these combinatorial formulations and coordinate treatment methods for the prevention or treatment of prostate hypertrophy in a mammalian subject include, but are not limited to, finasteride, dutasteride, terazosin, doxazosin, tamsulosin, or an alpha blocker. In addition, adjunctive or secondary therapies may be used such as, but not limited to, transurethral resection of the prostate, transurethral incision of the prostate, laser surgery, or prostatectomy.

Exemplary combinatorial formulations and coordinate treatment methods in the treatment of rheumatoid arthritis employ a phorbol ester compound of Formula I in combination with one or more additional, rheumatoid arthritis treating or other indicated, secondary or adjunctive therapeutic agents. The secondary or adjunctive therapeutic agents used in combination with a phorbol ester, e.g., TPA, in these embodiments may possess direct or indirect effects, alone or in combination with a phorbol ester, e.g. TPA; may exhibit other useful adjunctive therapeutic activity in combination with a phorbol ester, e.g. TPA (such as anti-inflammatory, immunosuppressing, TNF inhibiting, antibiotic, calcineurin inhibitor, pyrimidine synthesis inhibitor, 5-LO inhibitor, antifolate, IL-1 receptor antagonist, T cell costimulation inhibitor); or may exhibit adjunctive therapeutic activity useful for treating or preventing rheumatoid arthritis or associated symptoms alone or in combination with, e.g. TPA.

Useful adjunctive or secondary therapeutic agents in these combinatorial formulations and coordinate treatment methods for the prevention or treatment of rheumatoid arthritis in a mammalian subject include, but are not limited to, non-steroidal anti-inflammatory agent, steroid, disease-modifying anti-rheumatic drug, an immunosuppressant, TNF-α inhibitor, anakinra, abatacept, adalimumab, azathioprine, chloroquine, hydroxychloroquine, ciclosporin, D-penicillamine, etanercept, golimumab, gold salts, infliximab, leflunomide, methotrexate, minocycline, sulfasalazine, rituximab, or tocilizumab.

Exemplary combinatorial formulations and coordinate treatment methods in the treatment of autoimmune disorders employ a phorbol ester compound of Formula I in combination with one or more additional, autoimmune disease treating or other indicated, secondary or adjunctive therapeutic agents. The secondary or adjunctive therapeutic agents used in combination with a phorbol ester, e.g., TPA, in these embodiments may possess direct or indirect effects, alone or in combination with the phorbol ester, e.g. TPA; may exhibit other useful adjunctive therapeutic activity in combination with the phorbol ester, e.g. TPA (such as immunosuppressive, antibody suppressing, anticholinesterase); or may exhibit adjunctive therapeutic activity useful for treating or preventing autoimmune disorders including myasthemia gravis or associated symptoms alone or in combination with the phorbol ester, e.g. TPA.

Useful adjunctive or secondary therapeutic agents in these combinatorial formulations and coordinate treatment methods for the prevention or treatment of autoimmune disorders in a mammalian subject include, but are not limited to, anticholinesterase, corticosteroid, or immunosuppressive agent.

Exemplary combinatorial formulations and coordinate treatment methods in the treatment of kidney disease employ the phorbol ester compound of Formula I in combination with one or more additional, kidney disease treating or other indicated, secondary or adjunctive therapeutic agents. The secondary or adjunctive therapeutic agents used in combination with, e.g., TPA, in these embodiments may possess direct or indirect effects, alone or in combination with, e.g. TPA, may exhibit other useful adjunctive therapeutic activity in combination with, e.g. TPA (such as anticholinergic, antidepressant); or may exhibit adjunctive therapeutic activity useful for treating or preventing kidney disease or associated symptoms alone or in combination with, e.g. TPA.

Useful adjunctive or secondary therapeutic agents in these combinatorial formulations and coordinate treatment methods for the prevention or treatment of kidney disease in a mammalian subject include, but are not limited to, anticholinergic, topical estrogen, imipramine or duloxetine.

Exemplary combinatorial formulations and coordinate treatment methods in the treatment of urinary incontinence employ the phorbol ester compound of Formula I in combination with one or more additional, urinary incontinence treating or other indicated, secondary or adjunctive therapeutic agents. The secondary or adjunctive therapeutic agents used in combination with, e.g., TPA, in these embodiments may possess direct or indirect effects, alone or in combination with, e.g. TPA, may exhibit other useful adjunctive therapeutic activity in combination with, e.g. TPA (such as anticholinergic, antidepressant); or may exhibit adjunctive therapeutic activity useful for treating or preventing urinary incontinence or associated symptoms alone or in combination with, e.g. TPA.

Useful adjunctive or secondary therapeutic agents in these combinatorial formulations and coordinate treatment methods for the prevention or treatment of urinary incontinence in a mammalian subject include, but are not limited to, anticholinergic, topical estrogen, imipramine or duloxetine.

The forgoing and additional objects, features, aspects and advantages of the present invention will become apparent from the following detailed description.

DETAILED DESCRIPTION

Novel methods and compositions have been identified for use in treating chronic or recurring conditions, or to repair the damage left by episodes of illness or treatment of illness in mammalian subjects, including humans.

In various embodiments, the methods and compositions are effective to prevent or treat HIV and AIDS and related conditions, diseases caused by HIV and AIDS, symptoms of HIV and AIDS, and/or diseases acquired because of HIV or AIDS infection. In other embodiments, the methods and compositions are effective to prevent or treat neoplastic diseases and symptoms of such diseases. Such neoplastic diseases may or may not be malignant. In some embodiments, the neoplastic diseases may be solid or non-solid cancers. In other embodiments, the cancers may be refractory or relapses. In additional embodiments, the methods and compositions are effective in preventing or ameliorating damage or side effects from chemotherapeutic agents. In further embodiments, the methods and compositions as described herein are effective in preventing or ameliorating damage or side effects from radiation therapy. In other embodiments, the methods and compositions as described herein are effective in preventing or treating damage from stroke. In additional embodiments, the methods and compositions as described herein are effective in treating rheumatoid arthritis. In other embodiments, the methods and compositions as described herein are effective in decreasing the signs of aging. In another embodiment, the methods and compositions as described herein are effective in treating prostate hypertrophy. In additional embodiments, the methods and compositions as described herein are effective in treating autoimmune disorders. In further embodiments, the methods and compositions as described herein are effective in treating urinary incontinence. In other embodiments, the methods and compositions as described herein are effective in treating kidney disease. In additional embodiments, the methods and compositions as described herein are effective in treating Parkinson's disease.

The composition and methods as described herein may prevent or reduce viral load, decrease latent reservoirs of HIV, increase immune responsiveness, increase the release of Th1 cytokines, prevent or reduce symptoms and conditions associated with HIV and AIDS, decrease and/or eliminate neoplastic cells, increase white blood cell counts, induce remission, maintain remission, prevent or reduce symptoms and conditions associated with malignancies, increase ERK phosphorylation, decrease or eliminate radiation damage, boost the immune system, decrease nausea, decrease or prevent hair loss, increase appetite, decrease soreness, increase energy levels, relieve gastrointestinal distress, decrease bruising, eliminate oral ulcers, decrease or eliminate skin damage due to radiation, increase or maintain neutrophil levels, increase or maintain platelet levels, decrease edema, decrease or eliminate moist desquamation, prevent or treat paralysis, increase spatial awareness, decrease memory loss, decrease aphasia, increase coordination and balance, improve cognition, decrease or eliminate tremors, decrease or eliminate stiffness and rigidity, improve sleep quality, increase stability, improve mobility, improve bladder control, increase continence, improve appetite, ease muscle or joint aches, improve vision, and/or improve muscle control, and strengthening in the immune system.

Formulations and methods provided herein employ a phorbol ester or derivative compound of Formula I as more fully described in U.S. patent application Ser. No. 12/023,753, filed Jan. 31, 2008, which claims priority benefit of U.S. Provisional patent application Ser. No. 60/898,810, filed Jan. 31, 2007, each of which is incorporated herein in its entirety by reference,

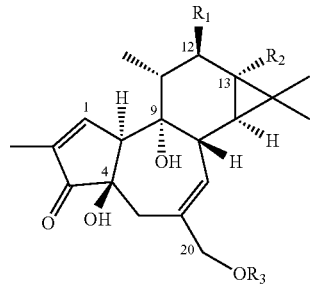

Formula I wherein $R_1$ and $R_2$ may be hydrogen; hydroxyl,

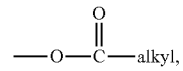

wherein the alkyl group contains 1 to 15 carbon atoms;

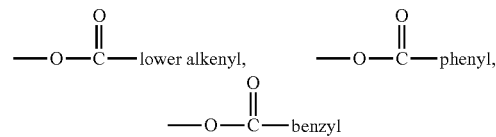

and substituted derivatives thereof and $R_3$ may be hydrogen or

including all active pharmaceutically acceptable compounds of this description as well as various foreseen and readily provided complexes, salts, solvates, isomers, enantiomers, polymorphs and prodrugs of these compounds and combinations thereof as novel HIV and AIDS treating compounds.

Viral load decreasing formulations and methods provided herein employ a phorbol ester or derivative compound of Formula I, above, including all active pharmaceutically acceptable compounds of this description as well as various foreseen and readily provided complexes, salts, solvates, isomers, enantiomers, polymorphs and prodrugs of these compounds and combinations thereof as novel viral load decreasing agents.

Immune responsiveness increasing formulations and methods provided herein employ a phorbol ester or derivative compound of Formula I, above, including all active pharmaceutically acceptable compounds of this description as well as various foreseen and readily provided complexes, salts, solvates, isomers, enantiomers, polymorphs and prodrugs of these compounds and combinations thereof as immune stimulatory compounds.

Th1 cytokine increasing formulations and methods provided herein employ a phorbol ester or derivative compound of Formula I, above, including all active pharmaceutically acceptable compounds of this description as well as various foreseen and readily provided complexes, salts, solvates, isomers, enantiomers, polymorphs and prodrugs of these compounds and combinations thereof as novel Th1 cytokine increasing agents.

Formulations and methods provided herein additionally employ a phorbol ester or derivative compound of Formula I, above, including all active pharmaceutically acceptable compounds of this description as well as various foreseen and readily provided complexes, salts, solvates, isomers, enantiomers, polymorphs and prodrugs of these compounds and combinations thereof in the treatment of neoplastic diseases.

Apoptosis inducing formulations and methods provided herein employ a phorbol ester or derivative compound of Formula I, above, including all active pharmaceutically acceptable compounds of this description as well as various foreseen and readily provided complexes, salts, solvates, isomers, enantiomers, polymorphs and prodrugs of these compounds and combinations thereof as chemotherapeutic agents that induce apoptosis in neoplasms.

Remission inducing formulations and methods provided herein employ a phorbol ester or derivative compound of Formula I, above, including all active pharmaceutically acceptable compounds of this description as well as various foreseen and readily provided complexes, salts, solvates, isomers, enantiomers, polymorphs and prodrugs of these compounds and combinations thereof as anti-neoplasm agents.

Formulations and methods provided herein further employ a phorbol ester or derivative compound of Formula I, above, including all active pharmaceutically acceptable compounds of this description as well as various foreseen and readily provided complexes, salts, solvates, isomers, enantiomers, polymorphs and prodrugs of these compounds and combinations thereof in the prevention or treatment of side effects from chemotherapy.

Formulations and methods provided herein additionally employ a phorbol ester or derivative compound of Formula I, above, including all active pharmaceutically acceptable compounds of this description as well as various foreseen and readily provided complexes, salts, solvates, isomers, enantiomers, polymorphs and prodrugs of these compounds and combinations thereof in the prevention or treatment of side effects from radiation therapy.

Stroke treating formulations and methods provided herein employ a phorbol ester or derivative compound of Formula I, above, including all active pharmaceutically acceptable compounds of this description as well as various foreseen and readily provided complexes, salts, solvates, isomers, enantiomers, polymorphs and prodrugs of these compounds and combinations thereof as anti-stroke agents.

Rheumatoid arthritis treating formulations and methods provided herein employ a phorbol ester or derivative compound of Formula I, above, including all active pharmaceutically acceptable compounds of this description as well as various foreseen and readily provided complexes, salts, solvates, isomers, enantiomers, polymorphs and prodrugs of these compounds and combinations thereof as anti-rheumatoid agents.

Anti-Parkinsonian formulations and methods provided herein employ a phorbol ester or derivative compound of Formula I, above, including all active pharmaceutically acceptable compounds of this description as well as various foreseen and readily provided complexes, salts, solvates, isomers, enantiomers, polymorphs and prodrugs of these compounds and combinations thereof as anti-Parkinsonian agents.

Formulations and methods provided herein also employ a phorbol ester or derivative compound of Formula I, above, including all active pharmaceutically acceptable compounds of this description as well as various foreseen and readily provided complexes, salts, solvates, isomers, enantiomers, polymorphs and prodrugs of these compounds and combinations thereof in the treatment of prostate hypertrophy.

Formulations and methods provided herein additionally employ a phorbol ester or derivative compound of Formula I, above, including all active pharmaceutically acceptable compounds of this description as well as various foreseen and readily provided complexes, salts, solvates, isomers, enantiomers, polymorphs and prodrugs of these compounds and combinations thereof in the treatment of autoimmune disorders.

Formulations and methods provided herein further employ a phorbol ester or derivative compound of Formula I, above, including all active pharmaceutically acceptable compounds of this description as well as various foreseen and readily provided complexes, salts, solvates, isomers, enantiomers, polymorphs and prodrugs of these compounds and combinations thereof in the treatment of carpal tunnel syndrome.

Formulations and methods provided herein additionally employ a phorbol ester or derivative compound of Formula I, above, including all active pharmaceutically acceptable compounds of this description as well as various foreseen and readily provided complexes, salts, solvates, isomers, enantiomers, polymorphs and prodrugs of these compounds and combinations thereof in the treatment of kidney disease.

Continence inducing formulations and methods provided herein employ a phorbol ester or derivative compound of Formula I, above, including all active pharmaceutically acceptable compounds of this description as well as various foreseen and readily provided complexes, salts, solvates, isomers, enantiomers, polymorphs and prodrugs of these compounds and combinations thereof as continence increasing agents.

A broad range of mammalian subjects, including human subjects, are amenable to treatment using the formulations and methods of the invention. These subjects include, but are not limited to, individuals suffering from diseases or conditions including neoplastic diseases and viral diseases such as HIV and AIDS, as well as individuals suffering from Parkinson's disease, stroke, rheumatoid arthritis, side effects from chemotherapy, side effects from radiation therapy, prostate hypertrophy, urinary incontinence, Myasthemia gravis, and kidney disease.

Subjects amenable to treatment include HIV+ human and other mammalian subjects presenting with oral lesions, fatigue, skin thrush, fever, lack of appetite, diarrhea, apthous ulcers, malabsorption, thrombocytopenia, weight loss, anemia, lymph node enlargement, susceptibility to and severity of secondary conditions such as mycobacterium avium complex, salmonellosis, syphilis, neuroshyphilis, tuberculosis (TB), bacillary angiomatosis, aspergillosis, candidiasis, coccidioidomycosis, listeriosis, pelvic inflammatory disease, Burkitt's lymphoma, cryptococcal meningitis, histoplasmosis, Kaposi's sarcoma, lymphoma, systemic non-Hodgkin's lymphoma (NHL), primary CNS lymphoma, cryptosporidiosis, isosporiasis, microsporidiosis, pneumocystis carinii pneumonia (PCP), toxoplasmosis, cytomegalovirus (CMV), hepatitis, herpes simplex, herpes zoster, human papiloma virus (HPV, genital warts, cervical cancer), molluscum contagiosum, oral hairy leukoplakia (OHL), and progressive multifocal leukoencephalopathy (PML).

Within the methods and compositions of the invention, one or more phorbol ester compound(s) of Formula I as disclosed herein is/are effectively formulated or administered as an agent effective for treating HIV/AIDS and/or related disorders. In exemplary embodiments, TPA is demonstrated for illustrative purposes to be an effective agent in pharmaceutical formulations and therapeutic methods, alone or in combination with one or more adjunctive therapeutic agent(s). The present disclosure further provides additional, pharmaceutically acceptable phorbol ester compounds in the form of a native or synthetic compound, including complexes, derivatives, salts, solvates, isomers, enantiomers, polymorphs, and prodrugs of the compounds disclosed herein, and combinations thereof, which are effective as therapeutic agents within the methods and compositions of the invention in the treatment of HIV/AIDS and related conditions.

Acquired immune deficiency syndrome or acquired immunodeficiency syndrome (AIDS or Aids) is a collection of symptoms and infections resulting from damage to the immune system caused by infection with the human immunodeficiency virus (HIV). The damage to the immune system leaves individuals prone to opportunistic infections and tumors. Although treatments for AIDS and HIV exist to slow the virus's progression and the severity of the symptoms, there is no known cure.

HIV is a retrovirus that primarily infects components of the human immune system such as CD4+ T cells, macrophages and dendritic cells. When CD4+ T cells are destroyed and their total count decreases to below 200 CD4+ T cells/μL of blood or the percentage of CD4+ T-cell as a fraction of the total lymphocytes falls to less than 14%, cellular immunity is lost, leading to AIDS.

It is currently believed that a change in the $T_h1$ and $T_h2$ cytokine balance can contribute to immune dysregulation associated with HIV infection. $T_h1$ cells produce cytokines that stimulate proliferation of cytotoxic T cells. $T_h2$ cells produce cytokines that are responsible for activation of the humoral immune responses in healthy people. Progression from HIV infection to AIDS is characterized by a decrease in levels of $T_h1$ cytokines IL-2, IL-12 and IFN-γ with a concomitant increase in levels of $T_h2$ cytokines IL-4, IL-5 and IL-10. (Clerci, Immunology Today, v. 14, No. 3, p. 107-110, 1993; Becker, Virus Genes 28:1, 5-18 (2004)). Resistance to HIV infection and/or resistance to progression to AIDS may therefore be dependent on a $T_h1>T_h2$ dominance.

A fraction of CD4+ memory T cells contain integrated transcritpionally inactive proviruses for HIV. These latent reservoirs may be activated to produce active infectious virus following activation by specific antigens or cytokines. The half life of these CD4 memory T cells is at least 44 months making it extremely difficult to eliminate HIV and requiring extended continuation of antiretroviral therapy even when HIV levels in the peripheral blood are undetectable.

Prostratin, 12-deoxyphorbol 13-acetate, a non-tumor promoting phorbol ester, has reportedly shown some effectiveness for inhibiting HIV induced cell killing and viral replication. Prostratin reportedly activated viral expression in latently-infected cell lines, but had little or no effect on chronically-infected cell lines. (Gulakowski, et al., Antiviral Research v. 33, 87-97 (1997); Williams, et al., JBC v. 279, No. 40, P. 42008-42017 (2004)). Prostratin represents a distinct subclass of protein kinase C activators which has unique biological activities that differ from tumor-promoting phorbol esters such as TPA.

Mammalian subjects amenable to treatment with phorbol esters of Formula I, particularly TPA, according to the methods of the present invention additionally include, but are not limited to, mammalian subjects with neoplastic diseases including solid and non-solid cancers, including hematologic malignancies/bone marrow disorders, such as leukemia, including acute myeloid leukemia (AML), chronic myeloid leukemia (CML), chronic myeloid leukemia blast crisis, myelodysplasia, myeloproliferative syndrome; lymphoma, including Hodgkin's and non-Hodgkin's lymphoma; subcutaneous adenocarcinoma; ovarian teratocarcinoma; and prostate cancer. In some embodiments, such cancers may be relapses or refractory.

Within the methods and compositions of the invention, one or more phorbol ester compound(s) of Formula I as disclosed herein is/are effectively formulated or administered as an agent effective for treating neoplastic diseases. In exemplary embodiments, TPA is demonstrated for illustrative purposes to be an effective agent in pharmaceutical formulations and therapeutic methods, alone or in combination with one or more adjunctive therapeutic agent(s). The present disclosure further provides additional, pharmaceutically acceptable phorbol ester compounds in the form of a native or synthetic compound, including complexes, derivatives, salts, solvates, isomers, enantiomers, polymorphs, and prodrugs of the compounds disclosed herein, and combinations thereof, which are effective as therapeutic agents within the methods and compositions of the invention in the treatment of neoplastic diseases and symptoms of such diseases.

Neoplastic disease is any growth or tumor caused by abnormal and uncontrolled cell division; it may spread to other parts of the body through the lymphatic system or the blood stream. Such growths may be malignant or benign, solid or non-solid.

In some embodiments, the neoplastic diseases may be a hematological neoplasm/bone marrow disorder such as acute myeloid leukemia (AML). AML (also called acute myelogenous leukemia, acute myeloblastic leukemia, acute granulocytic leukemia, and acute nonlymphocytic leukemia) is the most common type of acute leukemia in adults. In AML, stem cells produced by the bone marrow usually develop into a type of immature white blood cell called myeloblasts (or myeloid blasts). In individuals suffering from AML, these myeloblasts do not mature into healthy white blood cells. Additionally, stem cells in individuals with AML may develop into abnormal red blood cells or platelets. The lack of normal blood cells increases incidences of infection, anemia, and easy bleeding. Additionally, the leukemia cells can spread outside the blood to other parts of the body, including the central nervous system (brain and spinal cord), skin, and gums.

The average age of a patient with AML is over 64 years of age. Patients over the age of 60 treated for AML with standard chemotherapeutics have a remission rate of less than 20%. Additionally, patients who develop AML after an antecedent hematologic disorder or prior leukemogenic chemotherapy/radiation therapy have similarly poor outcomes.

Chemotherapy is the treatment of cancer with an antineoplastic drug or combination of such drugs. Chemotherapy works by impairing the reproduction of rapidly splitting cells, a property common in cancerous cells. However it does not actively distinguish between healthy cells that are also rapidly splitting and cancerous cells and it has a number of side effects such as, but not limited to, alopecia, nausea, vomiting, poor appetite, soreness, neutropenia, anemia, thrombocytopenia, dizziness, fatigue, constipation, oral ulcers, itchy skin, peeling, nerve and muscle leprosy, auditory changes, problems with blood, weight loss, diarrhea, immunosuppression, bruising, tendency to bleed easily, heart damage, liver damage, kidney damage, vertigo and encephalopathy.

Mammalian subjects amenable to treatment with phorbol esters of Formula I, particularly TPA, according to the methods of the present invention additionally include, but are not limited to, mammalian subjects undergoing chemotherapy.

Within the methods and compositions of the invention, one or more phorbol ester compound(s) of Formula I as disclosed herein is/are effectively formulated or administered as an agent effective for preventing or treating side effects due to chemotherapy. In exemplary embodiments, TPA is demonstrated for illustrative purposes to be an effective agent in pharmaceutical formulations and therapeutic methods, alone or in combination with one or more adjunctive therapeutic agent(s). The present disclosure further provides additional, pharmaceutically acceptable phorbol ester compounds in the form of a native or synthetic compound, including complexes, derivatives, salts, solvates, isomers, enantiomers, polymorphs, and prodrugs of the compounds disclosed herein, and combinations thereof, which are effective as therapeutic agents within the methods and compositions of the invention in the prevention or treatment of side effects due to chemotherapy.

Radiation therapy uses high-energy radiation to shrink tumors and kill cancer cells. It may be applied externally, internally, or systemically. It can cause acute or chronic side effects. Acute side effects occur during treatment, and chronic side effects occur months or even years after treatment ends. The side effects that develop depend on the area of the body being treated, the dose given per day, the total dose given, the patient's general medical condition, and other treatments given at the same time. (National Cancer Institute, 2011). Common side effects of radiation therapy are moist desquamation, soreness, diarrhea, nausea, vomiting, appetite loss, constipation, itchy skin, peeling, mouth and throat sores, edema, infertility, fibrosis, epilation, and mucosal dryness.

Mammalian subjects amenable to treatment with phorbol esters of Formula I, particularly TPA, according to the methods of the present invention additionally include, but are not limited to, mammalian subjects undergoing radiation therapy.

Within the methods and compositions of the invention, one or more phorbol ester compound(s) of Formula I as disclosed herein is/are effectively formulated or administered as an agent effective for preventing or treating side effects due to radiation therapy. In exemplary embodiments, TPA is demonstrated for illustrative purposes to be an effective agent in pharmaceutical formulations and therapeutic methods, alone or in combination with one or more adjunctive therapeutic agent(s). The present disclosure further provides additional, pharmaceutically acceptable phorbol ester compounds in the form of a native or synthetic compound, including complexes, derivatives, salts, solvates, isomers, enantiomers, polymorphs, and prodrugs of the compounds disclosed herein, and combinations thereof, which are effective as therapeutic agents within the methods and compositions of the invention in the prevention or treatment of side effects due to radiation therapy.

Rheumatoid arthritis affects about 1% of the U.S. population. While the cause is unknown, it is currently believed to be caused by a combination of genetic and environmental factors. It is a chronic form of arthritis that typically occurs in joints on both sides of the body and is also considered an autoimmune disease. In rheumatoid arthritis, the immune system attaches the synovium leading to fluid buildup in the joints, causing pain and frequently systemic inflammation. While symptoms present differently in different people, it generally causes joint pain, stiffness—particularly in the morning or after sitting for long periods of time, joint swelling, fever, muscle aches, inflammation of the joints, and rheumatoid nodules.

Mammalian subjects amenable to treatment with phorbol esters of Formula I, particularly TPA, according to the methods of the present invention additionally include, but are not limited to, mammalian subjects with rheumatoid arthritis.

Within the methods and compositions of the invention, one or more phorbol ester compound(s) of Formula I as disclosed herein is/are effectively formulated or administered as an agent effective for preventing or treating symptoms of rheumatoid arthritis. In exemplary embodiments, TPA is demonstrated for illustrative purposes to be an effective agent in pharmaceutical formulations and therapeutic methods, alone or in combination with one or more adjunctive therapeutic agent(s). The present disclosure further provides additional, pharmaceutically acceptable phorbol ester compounds in the form of a native or synthetic compound, including complexes, derivatives, salts, solvates, isomers, enantiomers, polymorphs, and prodrugs of the compounds disclosed herein, and combinations thereof, which are effective as therapeutic agents within the methods and compositions of the invention in the prevention or treatment of rheumatoid arthritis and symptoms thereof.

It is estimated that 4 to 6 million people worldwide suffer from Parkinson's disease, a chronic and progressive neurodegenerative brain disorder. It is believed to have both genetic and environmental triggers, but the exact cause is unknown. Many symptoms of Parkinson's disease result from a lack of dopamine and low norepinephrine levels. It is also characterized by the presence of Lewy bodies though their exact function is unknown. Parkinson's disease is characterized by tremors, bradykinesia, rigidity, speech impairment, postural instability and dementia.

Mammalian subjects amenable to treatment with phorbol esters of Formula I, particularly TPA, according to the methods of the present invention include, but are not limited to, mammalian subjects with Parkinson's disease.

Within the methods and compositions of the invention, one or more phorbol ester compound(s) of Formula I as disclosed herein is/are effectively formulated or administered as an agent effective for preventing or treating Parkinson's disease. In exemplary embodiments, TPA is demonstrated for illustrative purposes to be an effective agent in pharmaceutical formulations and therapeutic methods, alone or in combination with one or more adjunctive therapeutic agent(s). The present disclosure further provides additional, pharmaceutically acceptable phorbol ester compounds in the form of a native or synthetic compound, including complexes, derivatives, salts, solvates, isomers, enantiomers, polymorphs, and prodrugs of the compounds disclosed herein, and combinations thereof, which are effective as therapeutic agents within the methods and compositions of the invention in the prevention or treatment of Parkinson's disease and symptoms thereof.

Worldwide, stroke is the second leading cause of death, responsible for 4.4 million (9 percent) of the total 50.5 million deaths each year. (http://www.theuniversityhospital.com/stroke/stats.htm_University Hospital, Newark N.J., 2011) Ninety percent of stroke survivors suffer some type of impairment and it is the leading cause of disability among adults in the U.S. A stroke occurs when a blood vessel in the brain is blocked or bursts. Without oxygen, brain cells begin to die causing sudden numbness, tingling, weakness or loss of movement in the face, arm or leg. It can also cause sudden vision changes, trouble speaking, confusion, problems with walking or balance and a sudden, severe headache. After a stroke, an individual may suffer from paralysis, spatial impairment, impaired judgment, left-sided neglect, memory loss, aphasia, coordination and balance problems, nausea, vomiting, cognitive impairment, perception impairment, orientation impairment, homonymous hemianopsia and impulsivity.

Mammalian subjects amenable to treatment with phorbol esters of Formula I, particularly TPA, according to the methods of the present invention include, but are not limited to, mammalian subjects who have suffered or are at risk for a stroke.

Within the methods and compositions of the invention, one or more phorbol ester compound(s) of Formula I as disclosed herein is/are effectively formulated or administered as an agent effective for preventing or treating the effects of a stroke. In exemplary embodiments, TPA is demonstrated for illustrative purposes to be an effective agent in pharmaceutical formulations and therapeutic methods, alone or in combination with one or more adjunctive therapeutic agent(s). The present disclosure further provides additional, pharmaceutically acceptable phorbol ester compounds in the form of a native or synthetic compound, including complexes, derivatives, salts, solvates, isomers, enantiomers, polymorphs, and prodrugs of the compounds disclosed herein, and combinations thereof, which are effective as therapeutic agents within the methods and compositions of the invention in the prevention or treatment of stroke and symptoms thereof.

Prostate hypertrophy causes symptoms in more than half of men in their sixties and as many as 90 percent in their seventies and eighties. As the prostate enlarges, the layer of tissue surrounding it stops it from expanding, causing the gland to press against the urethra. The bladder wall becomes thicker and irritable and begins to contract even when it contains small amounts of urine, causing more frequent urination. Eventually, the bladder weakens and loses the ability to empty itself. (NIH Publication No. 07-3012, 2006) The most common symptoms of prostate hypertrophy are a hesitant, interrupted, weak stream; urgency and leaking or dribbling; and more frequent urination, especially at night. Additional symptoms include dribbling at the end of urination, urinary retention, incomplete emptying of the bladder, incontinence, urinary frequency, pain with urination, bloody urine, slowed or delayed urination, or straining to urinate.

Mammalian subjects amenable to treatment with phorbol esters of Formula I, particularly TPA, according to the methods of the present invention include, but are not limited to, mammalian subjects who have suffered or are at risk for prostate hypertrophy.

Within the methods and compositions of the invention, one or more phorbol ester compound(s) of Formula I as disclosed herein is/are effectively formulated or administered as an agent effective for preventing or treating prostate hypertrophy. In exemplary embodiments, TPA is demonstrated for illustrative purposes to be an effective agent in pharmaceutical formulations and therapeutic methods, alone or in combination with one or more adjunctive therapeutic agent(s). The present disclosure further provides additional, pharmaceutically acceptable phorbol ester compounds in the form of a native or synthetic compound, including complexes, derivatives, salts, solvates, isomers, enantiomers, polymorphs, and prodrugs of the compounds disclosed herein, and combinations thereof, which are effective as therapeutic agents within the methods and compositions of the invention in the prevention or treatment of prostate hypertrophy and symptoms thereof.

Autoimmune disorders are conditions that occur when the immune system mistakenly attacks and destroys healthy body tissue. In individuals with an autoimmune disorder, the immune system can't tell the difference between healthy body tissue and antigens. The result is an immune response that destroys normal body tissues. In Myasthemia Gravis, antibodies are directed against the body's own proteins. The autoantibodies most commonly act against the nicotinic acetylcholine receptor (nAChR), the receptor in the motor end plate for the neurotransmitter acetylcholine that stimulates muscular contraction. (Patrick J, Lindstrom J. Autoimmune response to acetylcholine receptor. Science (1973) 180:871-2.) Symptoms of myasthemia gravis include ptosis, diplopia, speech impairment, fatigability, muscle weakness, dysphagia, or dysarthria.

Mammalian subjects amenable to treatment with phorbol esters of Formula I, particularly TPA, according to the methods of the present invention include, but are not limited to, mammalian subjects who have or are at risk for autoimmune disorders.

Within the methods and compositions of the invention, one or more phorbol ester compound(s) of Formula I as disclosed herein is/are effectively formulated or administered as an agent effective for preventing or treating autoimmune disorders including myasthenia gravis. In exemplary embodiments, TPA is demonstrated for illustrative purposes to be an effective agent in pharmaceutical formulations and therapeutic methods, alone or in combination with one or more adjunctive therapeutic agent(s). The present disclosure further provides additional, pharmaceutically acceptable phorbol ester compounds in the form of a native or synthetic compound, including complexes, derivatives, salts, solvates, isomers, enantiomers, polymorphs, and prodrugs of the compounds disclosed herein, and combinations thereof, which are effective as therapeutic agents within the methods and compositions of the invention in the prevention or treatment of autoimmune disorders including myasthemia gravis and symptoms thereof.

Carpal tunnel syndrome occurs when the median nerve, which runs from the forearm into the palm of the hand, becomes pressed or squeezed at the wrist. Sometimes, thickening from irritated tendons or other swelling narrows the tunnel and causes the median nerve to be compressed. The result may be pain, weakness, or numbness in the hand and wrist, radiating up the arm. Although painful sensations may indicate other conditions, carpal tunnel syndrome is the most common and widely known of the entrapment neuropathies in which the body's peripheral nerves are compressed or traumatized. (NIH Publication No. 03-4898, 2002)

Mammalian subjects amenable to treatment with phorbol esters of Formula I, particularly TPA, according to the methods of the present invention include, but are not limited to, mammalian subjects who have or are at risk for carpal tunnel syndrome.

Within the methods and compositions of the invention, one or more phorbol ester compound(s) of Formula I as disclosed herein is/are effectively formulated or administered as an agent effective for preventing or treating carpal tunnel syndrome. In exemplary embodiments, TPA is demonstrated for illustrative purposes to be an effective agent in pharmaceutical formulations and therapeutic methods, alone or in combination with one or more adjunctive therapeutic agent(s). The present disclosure further provides additional, pharmaceutically acceptable phorbol ester compounds in the form of a native or synthetic compound, including complexes, derivatives, salts, solvates, isomers, enantiomers, polymorphs, and prodrugs of the compounds disclosed herein, and combinations thereof, which are effective as therapeutic agents within the methods and compositions of the invention in the prevention or treatment of carpal tunnel syndrome.

Chronic kidney disease are conditions that damage the kidneys and decrease their ability to regulate the balance of water and electrolytes, discharge metabolic waste and secreting hormones essential to human body. Symptoms of kidney disease include urinary incontinence, increased excretion of urine, uremia, and oliguria.

Mammalian subjects amenable to treatment with phorbol esters of Formula I, particularly TPA, according to the methods of the present invention include, but are not limited to, mammalian subjects who have or are at risk for kidney disease.

Within the methods and compositions of the invention, one or more phorbol ester compound(s) of Formula I as disclosed herein is/are effectively formulated or administered as an agent effective for preventing or treating kidney disease. In exemplary embodiments, TPA is demonstrated for illustrative purposes to be an effective agent in pharmaceutical formulations and therapeutic methods, alone or in combination with one or more adjunctive therapeutic agent(s). The present disclosure further provides additional, pharmaceutically acceptable phorbol ester compounds in the form of a native or synthetic compound, including complexes, derivatives, salts, solvates, isomers, enantiomers, polymorphs, and prodrugs of the compounds disclosed herein, and combinations thereof, which are effective as therapeutic agents within the methods and compositions of the invention in the prevention or treatment of kidney disease and symptoms thereof.

Urinary incontinence is a common and often embarrassing problem. The severity can range from occasionally leaking urine when coughing or sneezing, to losing complete control. Urinary incontinence may be caused by a variety of conditions including infection, pregnancy, aging, bladder stones, prostate cancer, bladder cancer, obstruction, prostatitis, hysterectomy, and medication. It may be transitory or permanent.

Mammalian subjects amenable to treatment with phorbol esters of Formula I, particularly TPA, according to the methods of the present invention include, but are not limited to, mammalian subjects who have or are at risk for urinary incontinence.

Within the methods and compositions of the invention, one or more phorbol ester compound(s) of Formula I as disclosed herein is/are effectively formulated or administered as an agent effective for preventing or treating urinary incontinence. In exemplary embodiments, TPA is demonstrated for illustrative purposes to be an effective agent in pharmaceutical formulations and therapeutic methods, alone or in combination with one or more adjunctive therapeutic agent(s). The present disclosure further provides additional, pharmaceutically acceptable phorbol ester compounds in the form of a native or synthetic compound, including complexes, derivatives, salts, solvates, isomers, enantiomers, polymorphs, and prodrugs of the compounds disclosed herein, and combinations thereof, which are effective as therapeutic agents within the methods and compositions of the invention in the prevention or treatment of urinary incontinence and symptoms thereof.

Phorbol is a natural, plant-derived polycyclic alcohol of the tigliane family of diterpenes. It was first isolated in 1934 as the hydrolysis product of croton oil derived from the seeds of *Croton tiglium*. It is well soluble in most polar organic solvents and in water. Esters of phorbol have the general structure of Formula I, below:

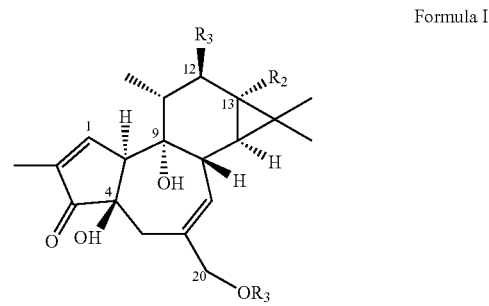

Formula I wherein $R_1$ and $R_2$ are selected from the group consisting of hydrogen; hydroxyl,

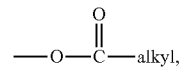

wherein the alkyl group contains 1 to 15 carbon atoms,

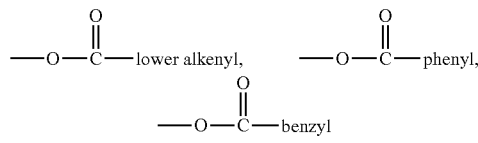

and substituted derivatives thereof and $R_3$ may be hydrogen,

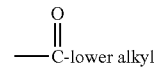

or substituted derivatives thereof.

The term "lower alkyl" or "lower alkenyl" as used herein means moieties containing 1-7 carbon atoms. In the compounds of the Formula I, the alkyl or alkenyl groups may be straight or branched chain. In some embodiments, either or both $R_1$ or $R_1$, are a long chain carbon moiety (i.e., Formula I is decanoate or myristate).

The alkyl, alkenyl, phenyl and benzyl groups of the formulas herein may be unsubstituted or substituted with halogens, preferably, chlorine, fluorine or bromine; nitro; amino and similar type radicals.

Organic and synthetic forms of phorbol esters, including any preparations or extracts from herbal sources such as *croton tigliun*, are contemplated as useful compositions comprising phorbol esters (or phorbol ester analogs, related compounds and/or derivatives) for use within the embodiments herein. Useful phorbol esters and/or related compounds for use within the embodiments herein will typically have a structure as illustrated in Foiuiula I, although functionally equivalent analogs, complexes, conjugates, and derivatives of such compounds will also he appreciated by those skilled in the art as within the scope of the invention.

In more detailed embodiments, illustrative structural modifications according to Formula I above will be selected to provide useful candidate compounds for treating and/or preventing HIV and AIDS and/or neoplastic diseases, wherein: at least one of $R_1$ and $R_2$ are other than hydrogen and $R_3$ is selected from the group consisting of hydrogen

and substituted derivatives thereof. In another embodiment, either $R_1$ or $R_2$ is

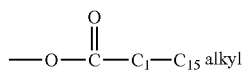

the remaining $R_1$ or $R_2$ is

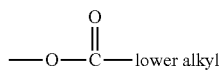

and $R_3$ is hydrogen.

An exemplary embodiment of a phorbol ester compound of Formula I useful in the treatment of cytopathic diseases such as HIV and AIDS and/or neoplastic diseases, particularly AML, is found in phorbol 12-myristate-13-acetate (also known as PMA or 12-O-tetradecanoyl-phorbol-13-acetate (TPA)) shown in Formula II, below.

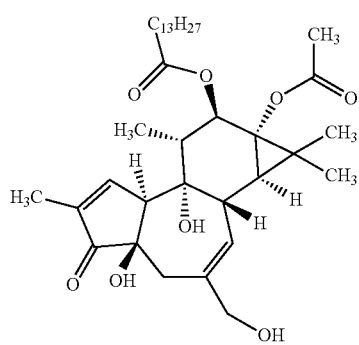

Formula II

Additional useful phorbol esters and related compounds and derivatives within the formulations and methods of the invention include, but are not limited to, other pharmaceutically acceptable active salts of said compounds, as well as active isomers, enantiomers, polymorphs, glycosylated derivatives, solvates, hydrates, and/or prodrugs of said compounds. Further exemplary forms of phorbol esters for use within the compositions and methods of the invention include, but are not limited to, phorbol 13-butyrate; phorbol 12-decanoate; phorbol 13-decanoate; phorbol 12,13-diacetate; phorbol 13,20-diacetate; phorbol 12,13-dibenzoate; phorbol 12,13-dibutyrate; phorbol 12,13-didecanoate; phorbol 12,13-dihexanoate; phorbol 12,13-dipropionate; phorbol 12-myristate; phorbol 13-myristate; phorbol 12,13,20-triacetate; 12-deoxyphorbol 13-angelate; 12-deoxyphorbol 13-angelate 20-acetate; 12-deoxyphorbol 13-isobutyrate; 12-deoxyphorbol 13-isobutyrate-20-acetate; 12-deoxyphorbol 13-phenylacetate; 12-deoxyphorbol 13-phenylacetate 20-acetate; 12-deoxyphorbol 13-tetradecanoate; phorbol 12-tigliate 13-decanoate; 12-deoxyphorbol 13-acetate; phorbol 12-acetate; and phorbol 13-acetate.

Phorbol ester compositions herein comprise HIV- and AIDS-treating compositions comprising an anti-AIDS effective amount of a phorbol ester compound of Formula I, which is effective for prophylaxis and/or treatment of HIV, AIDS, and/or HIV-related symptoms, including opportunistic infections, in a mammalian subject. An "anti-HIV", "anti-AIDS", or "AIDS treating" effective amount of the active compound is therapeutically effective, in a single or multiple unit dosage form, over a specified period of therapeutic intervention, to measurably alleviate one or more symptoms of AIDS in a subject, and/or to alleviate one or more symptom(s) or condition(s) associated with HIV infection in the subject. Within exemplary embodiments, the compositions of the invention are effective in treatment methods to alleviate symptoms of AIDS or other HIV-related conditions in human and other mammalian subjects vulnerable to HIV infection.

Phorbol ester compositions herein additionally may comprise chemotherapeutic compositions comprising an antineoplastic effective amount of a phorbol ester or derivative compound of Formula I, which is effective for maintenance and treatment of malignancies or symptoms caused by cancer in a mammalian subject. A "chemotherapeutic", "anti-tumor," "cancer treating", "apoptosis inducing", "remission inducing", "remission maintaining" effective amount of the active compound is therapeutically effective, in a single or multiple unit dosage form, over a specified period of therapeutic intervention, to measurably alleviate one or more symptoms of malignancy in a subject, and/or to alleviate one or more symptom(s) or condition(s) associated with malignancy in the subject. Within exemplary embodiments, the compositions of the invention are effective in treatment methods to alleviate symptoms of neoplastic disease related conditions in human and other mammalian subjects vulnerable to malignancies.

Compositions as described herein comprise chemoprotective compositions comprising an effective amount of a phorbol ester compound of Formula I to prevent or alleviate the side effects of chemotherapy. A "chemoprotective," "anti-inflammatory," "neutrophil stimulating," "erythropoiesis stimulating," "bone resorbtion inhibiting," "bone strengthening," "antiemetic," "pain relieving" effective amount of the active compound is therapeutically effective, in a single or multiple unit dosage form, over a specified period of therapeutic intervention, to measurably alleviate one or more of the side effects of chemotherapy in a subject. Within exemplary embodiments, the compositions of the invention are effective in treatment methods to alleviate side effects of chemotherapy in human and other mammalian subjects undergoing chemotherapy.

Compositions as described herein comprise radiation therapy protective compositions comprising an effective amount of a phorbol ester compound of Formula I to prevent or alleviate the side effects of radiation therapy. A "radiation protective," "radioprotective," "anti-swelling," "cytoprotective," "anti-mucositis," "epithelial stimulating," "anti-fibrotic," "platelet stimulating" effective amount of the active compound is therapeutically effective, in single or multiple unit dosage form, over a specified period of therapeutic intervention, to measurably alleviate one or more of the side effects of chemotherapy in a subject. Within exemplary embodiments, the compositions of the invention are effective in treatment methods to alleviate side effects of radiation therapy in human and other mammalian subjects undergoing radiation therapy.

Compositions as described herein comprise stroke treating compositions comprising a stroke damage alleviating or preventing effective amount of a phorbol ester compound of Formula I, which is effective for prophylaxis and/or treatment of stroke or stroke related symptoms or sequelae in a mammalian subject. A "stroke treating," "anti-clotting," "anticholesterolemic," "vasodilating," "antihypertensive," or "neuroprotective" effective amount of the active compound is therapeutically effective, in a single or multiple unit dosage form, over a specified period of therapeutic intervention, to measurably alleviate one or more symptoms or sequelae of stroke in the subject. Within exemplary embodiments, the compositions of the invention are effective in treatment methods to prevent or alleviate symptoms of stroke or sequelae of stroke in human and other mammalian subjects vulnerable to or who have suffered a stroke.

Compositions as described herein further comprise Parkinson's disease treating compositions comprising an effective amount of a phorbol ester compound of Formula I which is effective for prophylaxis and/or treatment of Parkinson's disease or related symptoms in a mammalian subject. A "Parkinson's disease treating," "dopamine increasing," "catechol-O-methyl transferase inhibiting," "aromatic L-amino acid decarboxylase inhibiting," "dopamine agonist," "neuroprotective," or "anticholinergic" effective amount of the active compound is therapeutically effective in a single or multiple unit dosage form, over a specified period of therapeutic intervention, to measurably alleviate or prevent one or more of the symptoms of Parkinson's disease in the subject. Within exemplary embodiments, the compositions of the invention are effective in treatment methods to prevent or alleviate symptoms of Parkinson's disease in human and other mammalian subjects suffering from or at risk for Parkinson's disease.

Compositions as described herein additionally comprise prostate hypertrophy treating compositions comprising an effective amount of a phorbol ester of a compound of Formula I, which is effective for prophylaxis and/or treatment of prostate hypertrophy or related symptoms or sequelae in a mammalian subject. A "prostate hypertrophy treating", "type II 5-alpha reductase inhibitor," or "muscle relaxant" effective amount of the active compound is therapeutically effective, in a single or multiple unit dosage form, over a specified period of therapeutic intervention, to measurably alleviate one or more symptoms or sequelae of prostate hypertrophy in the subject. Within exemplary embodiments, the compositions of the invention are effective in treatment methods to prevent or alleviate symptoms of prostate hypertrophy or sequelae in human and other mammalian subjects who have or are at risk for prostate hypertrophy.

Compositions as described herein further comprise rheumatoid arthritis treating compositions comprising anti-rheumatoid effective amounts of a phorbol ester of a compound of Formula I, which is effective for prophylaxis and/or treatment of rheumatoid arthritis or related symptoms in a mammalian subject. A "anti-rheumatoid," "anti-inflammatory," "immunosuppressing," "TNF inhibiting," "antibiotic," "calcineurin inhibitor," "pyrimidine synthesis inhibitor," "5-LO inhibitor," "antifolate," "IL-1 receptor antagonist," or "T cell costimulation inhibitor" effective amount of the active compound is therapeutically effective, in a single or multiple unit dosage form, over a specified period of therapeutic intervention, to measurably alleviate one or more symptoms of rheumatoid arthritis in the subject. Within exemplary embodiments, the compositions of the invention are effective in treatment methods to prevent or alleviate symptoms of rheumatoid arthritis in human and other mammalian subjects who have or are at risk for rheumatoid arthritis.

Compositions as described herein additionally comprise autoimmune disease treating compositions comprising an autoimmune disease treating effective amount of a phorbol ester of a compound of Formula I, which is effective for prophylaxis and/or treatment of an autoimmune disease such as myasthemia gravis or related symptoms or sequelae in a mammalian subject. An "autoimmune disorder treating," "myasthemia gravis treating," "immunosuppressive," "antibody suppressing," or "anticholinesterase" effective amount of the active compound is therapeutically effective, in a single or multiple unit dosage form, over a specified period of therapeutic intervention, to measurably alleviate one or more symptoms or sequelae of autoimmune disease, specifically myasthemia gravis in the subject. Within exemplary embodiments, the compositions of the invention are effective in treatment methods to prevent or alleviate symptoms of myasthemia gravis in human and other mammalian subjects who have or are at risk for myasthemia gravis.

Compositions as described herein additionally comprise kidney disease treating compositions comprising an effective amount of a phorbol ester of a compound of Formula I, which is effective for prophylaxis and/or treatment of kidney disease or related symptoms or sequelae in a mammalian subject. A "kidney disease treating," "anticholinergic," or "antidepressant" effective amount of the active compound is therapeutically effective, in a single or multiple unit dosage form, over a specified period of therapeutic intervention, to measurably alleviate one or more symptoms or sequelae of kidney disease, including incontinence in the subject. Within exemplary embodiments, the compositions of the invention are effective in treatment methods to prevent or alleviate symptoms of kidney disease in human and other mammalian subjects who have or are at risk for kidney disease.

Compositions as described herein additionally comprise urinary incontinence treating compositions comprising an effective amount of a phorbol ester of a compound of Formula I, which is effective for prophylaxis and/or treatment of urinary incontinence in a mammalian subject. A "continence increasing," "anticholinergic," "antibiotic," or "antidepressant" effective amount of the active compound is therapeutically effective, in a single or multiple unit dosage form, over a specified period of therapeutic intervention, to measurably alleviate one or more symptoms of urinary incontinence in the subject. Within exemplary embodiments, the compositions of the invention are effective in treatment methods to prevent or alleviate symptoms of urinary incontinence in human and other mammalian subjects who have or are at risk for kidney disease.

Phorbol ester treating, including chemotherapeutic, chemoprotectant, radioprotectant, stroke mitigating, Parkinson's disease treating, prostate hypertrophy treating, rheumatoid arthritis treating, anti-aging, kidney disease treating, continence increasing, autoimmune disease treating, and HIV treating, compositions of the invention typically comprise an effective amount or unit dosage of a phorbol ester compound of Formula I, which may be formulated with one or more pharmaceutically acceptable carriers, excipients, vehicles, emulsifiers, stabilizers, preservatives, buffers, and/or other additives that may enhance stability, delivery, absorption, half-life, efficacy, pharmacokinetics, and/or pharmacodynamics, reduce adverse side effects, or provide other advantages for pharmaceutical use. Effective amounts of a phorbol ester compound or related or derivative compound of Formula I (e.g., a unit dose comprising an effective concentration/amount of TPA, or of a selected pharmaceutically acceptable salt, isomer, enantiomer, solvate, polymorph and/or prodrug of TPA) will be readily determined by those of ordinary skill in the art, depending on clinical and patient-specific factors. Suitable effective unit dosage amounts of the active compounds for administration to mammalian subjects, including humans, may range from about 10 to about 1500 µg, about 20 to about 1000 µg, about 25 to about 750 µg, about 50 to about 500 µg, about 150 to about 500 µg, about 125 µg to about 500 µg, about 180 to about 500 µg, about 190 to about 500 µg, about 220 to about 500 µg, about 240 to about 500 µg, about 260 to about 500 µg, about 290 to about 500 µg. In certain embodiments, the disease treating effective dosage of a phorbol ester compound or related or derivative compound of Formula I may be selected within narrower ranges of, for example, 10 to 25 µg, 30-50 µg, 75 to 100 µg, 100 to 300 µg, or 150 to 500 µg. These and other effective unit dosage amounts may be administered in a single dose, or in the form of multiple daily, weekly or monthly doses, for example in a dosing regimen comprising from 1 to 5, or 2 to 3, doses administered per day, per week, or per month. In one exemplary embodiment, dosages of 10 to 30 µg, 30 to 50 µg, 50 to 100 µg, 100 to 300 µg, or 300 to 500 µg, are administered one, two, three, four, or five times per day. In more detailed embodiments, dosages of 50-100 µg, 100-300 µg, 300-400 µg, or 400-600 µg are administered once or twice daily. In a further embodiment, dosages of 50-100 µg, 100-300 µg, 300-400 µg, or 400-600 µg are administered every other day. In alternate embodiments, dosages are calculated based on body weight, and may be administered, for example, in amounts from about 0.5 µg/m$^2$ to about 300 µg/m$^2$ per day, about 1 µg/m$^2$ to about 200 g/m$^2$, about 1 µg/m$^2$ to about 187.5 µg/m$^2$ per day, about 1 µg/m$^2$ per day to about 175 µg/m$^2$ per day, about 1 µg/m$^2$ per day to about 157 µg/m$^2$ per day about 1 µg/m$^2$ to about 125 µg/m$^2$ per day, about 1 µg/m$^2$ to about 75 µg/m$^2$ per day, 1 µg/m$^2$ to about 50/g/m$^2$ per day, 2 µg/m$^2$ to about 50 µg/m$^2$ per day, 2 µg/m$^2$ to about 30 µg/m$^2$ per day or 3 µg/m$^2$ to about 30 µg/m$^2$ per day.

In other embodiments, dosages may be administered less frequently, for example, 0.5 µg/m$^2$ to about 300 µg/m$^2$ every other day, about 1 µg/m$^2$ to about 200 µg/m$^2$, about 1 µg/m$^2$ to about 187.5 µg/m$^2$ every other day, about 1 µg/m$^2$ to about 175 µg/m$^2$ every other day, about 1 µg/m$^2$ per day to about 157 µg/m$^2$ every other day about 1 g/m$^2$ to about 125 µg/m$^2$ every other day, about 1 µg/m$^2$ to about 75 µg/m$^2$ every other day, 1 µg/m$^2$ to about 50 µg/m$^2$ every other day, 2 µg/m$^2$ to about 50 µg/m$^2$ every other day, 2 µg/m$^2$ to about 30 µg/m$^2$ per day or 3 µg/m$^2$ to about 30 g/m$^2$ per day. In additional embodiments, dosages may be administered 3 times/week, 4 times/week, 5 times/week, only on weekdays, only in concert with other treatment regimens, on consecutive days, or in any appropriate dosage regimen depending on clinical and patient-specific factors The amount, timing and mode of delivery of compositions of the invention comprising a cytopathic disease treating effective amount of a phorbol ester compound of Formula I (AIDS treating, HIV preventing, HIV treating, HIV reservoir activating, Th1 cytokine increasing, ERK phosphorylation inducing, chemotherapeutic, anti-tumor, cancer treating, remission inducing, remission maintaining, apoptosis inducing effective amount) will be routinely adjusted on an individual basis, depending on such factors as weight, age, gender, and condition of the individual, the acuteness of the cytopathic disease and/or related symptoms, whether the administration is prophylactic or therapeutic, and on the basis of other factors known to effect drug delivery, absorption, pharmacokinetics, including half-life, and efficacy.

An effective dose or multi-dose treatment regimen for the instant disease treating (alternatively, "AIDS treating", "HIV treating", "HIV preventing", "HIV reservoir activating", or "Th1 cytokine increasing", "ERK phosphorylation inducing", "chemotherapeutic", "anti-tumor", "cancer treating", "apoptosis inducing", "remission inducing", "remission maintaining", "chemoprotective," "anti-inflammatory," "neutrophil stimulating," "erythropoiesis stimulating," "bone resorbtion inhibiting," "bone strengthening," "anti-emetic," "pain relieving," "radiation protective," "anti-swelling," "cytoprotective," "anti-mucositis," "epithelial stimulating," "anti-fibrotic," "platelet stimulating," "stroke treating," "anti-clotting," "anticholesterolemic," "vasodilating," "antihypertensive," "Parkinson's disease treating," "dopamine increasing," "catechol-O-methyl transferase inhibiting," "aromatic L-amino acid decarboxylase inhibiting," "dopamine agonist," "neuroprotective," "anticholinergic," "prostate hypertrophy treating", "type II 5-alpha reductase inhibitor," "muscle relaxant," "anti-rheumatoid," "anti-inflammatory," "immunosuppressing," "TNF inhibiting," "antibiotic," "calcineurin inhibitor," "pyrimidine synthesis inhibitor," "5-LO inhibitor," "antifolate," "IL-1 receptor antagonist," "T cell costimulation inhibitor," "autoimmune disorder treating," "myasthemia gravis treating," "immunosuppressive," "antibody suppressing," "anticholinesterase" "kidney disease treating," "continence increasing," "antidepressant") formulations of the invention will ordinarily be selected to approximate a minimal dosing regimen that is necessary and sufficient to substantially prevent or alleviate the symptoms of the disease including AIDS or neoplastic diseases such as cancer and related opportunistic diseases, stroke, autoimmune disease, kidney disease, urinary incontinence, Parkinson's disease, carpal tunnel syndrome, or prostate hypertrophy, in the subject, and/or to substantially prevent or alleviate one or more symptoms associated with AIDS, neoplastic diseases such as cancer, stroke, autoimmune disease, aging, urinary incontinence, kidney disease, Parkinson's disease, carpal tunnel syndrome, prostate hypertrophy, chemotherapy treatment, or radiation treatment in the subject. A dosage and administration protocol will often include repeated dosing therapy over a course of several days or even one or more weeks or years. An effective treatment regime may also involve prophylactic dosage administered on a day or multi-dose per day basis lasting over the course of days, weeks, months or even years.

Various assays and model systems can be readily employed to determine the therapeutic effectiveness of the treatment of cytopathic diseases. For example in the treatment of HIV or AIDS effectiveness may be demonstrated by a decrease in viral load, an increase in CD4 counts, an increase in CD3 counts, an increase in IL-2 and IFN production, a decrease in IL-4 and IL-10 production, and a decrease or elimination of the symptoms of AIDS among other methods of determining effectiveness known to those of skill in the art.

Effectiveness of the compositions and methods of the invention may be demonstrated, for example, through blood tests for HIV antibodies, viral load, CD4 levels, CD8 counts, and CD3 counts. Normal levels of CD4 are usually between 600 and 1200 per microliter, or 32-68% of lymphocytes. Individuals with a CD4 count of less than 350 have a weakened immune system. Those with a CD4 count of less than 200 are considered to have AIDS. CD8 levels in a healthy individual are generally between 150-1000 per microliter. CD3 levels in a healthy individual are generally between about 885-2270 per microliter. Levels of CD3, CD4 and CD8 cells may be measured, for example, using flow cytometry. Effective amounts of the compositions of the invention will increase levels of CD3, CD4 and CD8 positive cells by at least 10%, 20%, 30%, 50% or greater reduction, up to a 75-90%, or 95% or greater. Effective amounts will also move the CD3, CD4 and CD8 profile of an individual towards the optimal category for each type of glycoprotein.

Individuals may also be evaluated using a beta$_2$-microglobulin (beta$_2$-M) test. Beta$_2$-microglobulin is a protein released into the blood when a cell dies. A rising beta$_2$-M blood level can be used to measure the progression of AIDS. Effective amounts of a composition of the present invention will lead to a decrease or cessation of increase in the amount of beta$_2$-M.

Effectiveness may further be demonstrated using a complete blood count (CBC). The measurements taken in a CBC include a white blood cell count (WBC), a red blood cell count (RBC), the red cell distribution width, the hematocrit, and the amount of hemoglobin. Specific AIDS-related signs in a CBC include a low hematocrit, a sharp decrease in the number of blood platelets, and a low level of neutrophils. An effective amount of a composition of the present invention will increase the levels measured in a complete blood count by 10%, 20%, 30%, 50% or greater increase, up to a 75-90%, or 95% or greater. Effective amounts will also move the blood protein of an individual towards the optimal category for each type of protein.

Effectiveness of the compositions and methods of the invention may also be demonstrated by a decrease in the symptoms of HIV or AIDS including, but not limited to, oral lesions, fatigue, skin thrush, fever, lack of appetite, diarrhea, apthous ulcers, malabsorption, thrombocytopenia, weight loss, anemia, and lymph node enlargement.

Effectiveness of the compositions and methods of the invention may also be demonstrated by a decrease in the susceptibility to and severity of secondary or opportunistic conditions such as mycobacterium avium complex, salmonellosis, syphilis, neuroshyphilis, tuberculosis (TB), bacillary angiomatosis, aspergillosis, candidiasis, coccidioidomycosis, listeriosis, pelvic inflammatory disease, Burkitt's lymphoma, cryptococcal meningitis, histoplasmosis, Kaposi's sarcoma, lymphoma, systemic non-Hodgkin's lymphoma (NHL), primary CNS lymphoma, cryptosporidiosis, isosporiasis, microsporidiosis, pneumocystis carinii pneumonia (PCP), toxoplasmosis, cytomegalovirus (CMV), hepatitis, herpes simplex, herpes zoster, human papiloma virus (HPV, genital warts, cervical cancer), molluscum contagiosum, oral hairy leukoplakia (OHL), and progressive multifocal leukoencephalopathy (PML).

Effectiveness may further be demonstrated by reduction of detectable HIV in the HIV-infected subject; maintaining a normal T cell count; or maintaining normal p24 antigen levels.

Effectiveness in the treatment of neoplastic diseases may also be determined by a number of methods such as, but not limited to, ECOG Performance Scale, the Karnofsky Performance Scale, microscopic examination of blood cells, bone marrow aspiration and biopsy, cytogenetic analysis, biopsy, immunophenotyping, blood chemistry studies, a complete blood count, lymph node biopsy, peripheral blood smear, visual analysis of a tumor or lesion, or any other method of evaluating and/or diagnosing malignancies and tumor progression known to those of skill in the art.

For example, effectiveness of the compositions and methods herein in the treatment of hematologic malignancies/bone marrow disorders may be evaluated using, an absolute neutrophil count (ANC). A normal ANC is between 1,500 to 8,000/mm$^3$. Individuals suffering from hematologic malignancies/bone marrow disorders frequently have an ANC below 1500/mm$^3$, and may even reach levels below 500/mm$^3$. Effective amounts of the compositions and methods herein will increase an individual's ANC by 10%, 20%, 30%, 50% or greater increase, up to a 75-90%, or 95% or greater. Effective amounts may increase ANC levels above 1500/mm$^3$.

Effectiveness of the compositions and methods herein in the treatment of hematologic malignancies/bone marrow disorders may further be evaluated using, for example, a platelet count. A platelet count is normally between 150,000 to 450,000 platelets per microliter (×10-6/Liter). Individuals suffering from hematologic malignancies/bone marrow disorder may have platelet counts below 100,000 per microliter. Effective amounts of the compositions and methods herein will increase an individual's platelet count by 10%, 20%, 30%, 50% or greater increase, up to a 75-90%, or 95% or greater. Effective amounts may increase platelet levels above 100,000 per microliter.

Effectiveness of the compositions and methods herein in the treatment of hematologic malignancies/bone marrow disorders may additionally be evaluated, for example, by measuring the number of myeloblasts. Myeloblasts normally represent less than 5% of the cells in the bone marrow but should not be present in circulating blood. Effective amounts of the compositions and methods herein will decrease the number of myeloblasts by 10%, 20%, 30%, 50% or more, up to a 75-90%, 96% or greater decrease. Effective amounts may decrease myeloblasts to below 5%.

Effectiveness of the compositions and methods herein in the treatment of hematologic malignancies/bone marrow disorders may further be evaluated by examining myeloblasts for the presence of Auer rods. Effective amounts of the compositions of the present invention will decrease the number of Auer rods visible by 10%, 20%, 30%, 50% or more, up to a 75-90%, 96% or greater decrease up to the complete elimination of Auer rods.

Effectiveness of the compositions and methods of the invention may also be demonstrated by a decrease in the symptoms of subjects suffering from neoplastic disease including, but not limited to, anemia; chronic fatigue; excessive or easy bleeding, such as bleeding of the nose, gums, and under the skin; easy bruising, particularly bruising with no apparent cause; shortness of breath; petechiae; recurrent fever; swollen gums; slow healing of cuts; bone and joint discomfort; recurrent infections; weight loss; itching; night sweats; lymph node swelling; fever; abdominal pain and discomfort; disturbances in vision; coughing; loss of appetite; pain in the chest; difficulty swallowing; swelling of the face, neck and upper extremities; a need to urinate frequently, especially at night; difficulty starting urination or holding back urine; weak or interrupted flow of urine; painful or burning urination; difficulty in having an erection; painful ejaculation; blood in urine or semen; frequent pain or stiffness in the lower back, hips, or upper thighs; and weakness.

Effectiveness of the compositions and methods of the invention may also be demonstrated by a decrease in the symptoms of chemotherapeutic treatment including, but not limited to, alopecia, nausea, vomiting, poor appetite, soreness, neutropenia, anemia, thrombocytopenia, dizziness, fatigue, constipation, oral ulcers, itchy skin, peeling, nerve and muscle leprosy, auditory changes, problems with blood, weight loss, diarrhea, immunosuppression, bruising, tendency to bleed easily, heart damage, liver damage, kidney damage, vertigo and encephalopathy.

Effectiveness of the compositions and methods of the invention may also be demonstrated by a decrease in the symptoms that accompany radiation therapy including, but not limited to, moist desquamation, soreness, diarrhea, nausea, vomiting, appetite loss, constipation, itchy skin, peeling, mouth and throat sores, edema, infertility, fibrosis, epilation, and mucosal dryness in comparison to others who have received similar radiotherapy treatments.

Effectiveness in the treatment of rheumatoid arthritis may be demonstrated, for example, through the use of a variety of animal models including collagen-induced arthritis, as described below in Example 30, pristane induced arthritis, adjuvant induced arthritis, streptococcal cell wall induced arthritis, ovalbumin induced arthritis, antigen induced arthritis, or the air-pouch model.

Effectiveness of the compositions and methods of the invention in the treatment of rheumatoid arthritis may also be demonstrated by a decrease in the symptoms of rheumatoid arthritis including, but not limited to, joint pain, stiffness—particularly in the morning or after sitting for long periods of time, joint swelling, fever, muscle aches, inflammation of the joints, and rheumatoid nodules.

Effectiveness of the compositions and methods of the invention in the treatment of rheumatoid arthritis may also be demonstrated by a change in the erythrocyte sedimentation rate. Individuals with rheumatoid arthritis frequently have elevated levels of erythrocyte sedimentation. An effective amount of the compositions of the invention would decrease the levels of erythrocyte sedimentation by 10%, 20%, 30%, 50% or more, up to a 75-90%, 96% or greater decrease over the initial diagnostic levels of erythrocyte sedimentation. Effectiveness may also be demonstrated by a change in the levels of rheumatoid factor and anti-cyclic citrullinated antibodies.

Effectiveness of the compositions and methods of the invention in the treatment of Parkinson's disease may be demonstrated by a decrease in the symptoms of Parkinson's including, but not limited to, tremors, bradykinesia, rigidity, speech impairment, postural instability and dementia. Effectiveness of the phorbol ester compounds of the present invention in the treatment of Parkinson's disease may further be demonstrated by an increase in dopamine and/or norepinephrine levels. Such levels may increase 10%, 20%, 30%, 50% or greater increase, up to a 75-90%, or 95% or greater of normal levels.

Effectiveness of the compositions and methods of the invention in the treatment of Parkinson's disease may further be demonstrated by a decrease in the presence of Lewy bodies. Effectiveness may also demonstrated through the use of animal models, such as MPTP induced Parkinson's, retenone induced Parkinson's, surgically induced Parkinson's, paraquat induced Parkinson's, 6-OHDA induced Parkinson's, or α-synuclein overexpressing mice. The use of the compositions and methods of the invention will decrease the symptoms of Parkinson's disease expressed in these models by 0%, 20%, 30%, 50% or more, up to a 75-90%, 96% or greater decrease over control animals.

Effectiveness of the compositions and methods of the invention in the treatment of stroke may be demonstrated using a variety of model systems including temporary middle cerebral artery occlusion as shown in Example 22, permanent middle cerebral artery occlusion as shown in Example 21, endovascular filament middle cerebral artery occlusion, embolic middle cerebral artery occlusion as shown in Example 20, endothelin-1-induced constriction of arteries and veins, or cerebrocortical photothrombosis. Use of the phorbol ester compositions of the present invention will decrease the symptoms exhibited by the model systems by 0%, 20%, 30%, 50% or more, up to a 75-90%, 96% or greater decrease over control animals.

Effectiveness of the compositions and methods of the invention in the treatment of stroke may further be demonstrated by a decrease in the symptoms exhibited in individuals who have suffered a stroke. Such symptoms include, but are not limited to, paralysis, spatial impairment, impaired judgment, left-sided neglect, memory loss, aphasia, coordination and balance problems, nausea, vomiting, cognitive impairment, perception impairment, orientation impairment, homonymous hemianopsia and impulsivity. Use of the phorbol ester compositions of the present invention will decrease the symptoms exhibited by individuals by 0%, 20%, 30%, 50% or more, up to a 75-90%, 96% or greater decrease over initial states.

Effectiveness of the compositions and methods of the invention in the treatment of prostate hypertrophy may be demonstrated by a decrease in the symptoms associated with prostate hypertrophy including, but not limited to, hesitant, interrupted, weak stream; urgency and leaking or dribbling; more frequent urination; dribbling at the end of urination; urinary retention; incomplete emptying of the bladder; incontinence; urinary frequency; pain with urination; bloody urine; slowed or delayed urination; or straining to urinate. Use of the phorbol ester compositions of the present invention will decrease the symptoms exhibited by individuals by 0%, 20%, 30%, 50% or more, up to a 75-90%, 96% or greater decrease over initial states.

Effectiveness of the compositions and methods of the invention in the treatment of prostate hypertrophy may additionally be demonstrated through the use of various tests such as post-void residual urine test, pressure flow studies or a cytoscopy. Use of the phorbol ester compositions of the present invention will decrease the amount of residual urine, or increase the pressure flow by 0%, 20%, 30%, 50% or more, up to a 75-90%, 96% or greater over the results prior to treatment with a phorbol ester compound.

Effectiveness of the compositions and methods of the invention in the treatment of Myasthemia gravis may be demonstrated by a decrease in the symptoms associated with Myasthemia gravis including, but not limited to, ptosis, diplopia, speech impairment, fatigability, muscle weakness, dysphagia, or dysarthria. Use of the phorbol ester compositions of the present invention will decrease the symptoms exhibited by individuals by 0%, 20%, 30%, 50% or more, up to a 75-90%, 96% or greater decrease over initial states.

Effectiveness of the compositions and methods of the invention in the treatment of Myasthemia gravis may also be determined using the Tensilon test or the ice test, nerve conduction studies, Single Fibre EMG, or detection of serum antibodies to the acetylcholine receptor. Effectiveness can additionally be determined using animal models of Myasthemia gravis such as by immunizing animals with torpedo *californica* acetylcholine receptors (AChR) in complete Freund's adjuvant. Use of the phorbol ester compositions of the present invention will decrease the symptoms exhibited by individuals by 0%, 20%, 30%, 50% or more, up to a 75-90%, 96% or greater decrease over initial states and/or controls.

Effectiveness of the compositions and methods of the invention in the treatment of Carpal Tunnel syndrome maybe demonstrated by a decrease in symptoms associated with carpal tunnel syndrome including, but not limited to, pain, weakness, or numbness in the hand and wrist, radiating up the arm. Use of the phorbol ester compositions of the present invention will decrease the symptoms exhibited by individuals by 0%, 20%, 30%, 50% or more, up to a 75-90%, 96% or greater decrease over initial states.

Effectiveness of the compositions and methods of the invention in the treatment of kidney disease may be demonstrated by a decrease in symptoms associated with kidney disease including, but not limited to, urinary incontinence, increased excretion of urine, uremia, or oliguria. Use of the phorbol ester compositions of the present invention will decrease the symptoms exhibited by individuals by 0%, 20%, 30%, 50% or more, up to a 75-90%, 96% or greater decrease over initial states.

Effectiveness of the compositions and methods of the invention in the treatment of urinary incontinence may be demonstrated by a decrease in symptoms associated with urinary incontinence. Use of phorbol ester compositions of the present invention will decrease the symptoms exhibited by individuals by 0%, 20%, 30%, 50% or more, up to a 75-90%, 96% or greater decrease over initial states.

For each of the indicated conditions described herein, test subjects will exhibit a 10%, 20%, 30%, 50% or greater reduction, up to a 75-90%, or 96% or greater, reduction, in one or more symptom(s) caused by, or associated with, the disease, or related diseases or conditions in the subject, compared to placebo-treated or other suitable control subjects.

Within additional aspects of the invention, combinatorial disease treating ("AIDS treating," "HIV preventing," "HIV treating," "HIV reservoir activating," "Th1 cytokine increasing," "ERK phosphorylation inducing," "apoptosis inducing," "chemotherapeutic," "anti-tumor," "cancer treating," "remission inducing," "remission maintaining," "chemoprotective," "anti-inflammatory," "neutrophil stimulating," "erythropoiesis stimulating," "bone resorbtion inhibiting," "bone strengthening," "antiemetic," "pain relieving," "radiation protective," "anti-swelling," "cytoprotective," "anti-mucositis," "epithelial stimulating," "anti-fibrotic," "platelet stimulating," "stroke treating," "anti-clotting," "anticholesterolemic," "vasodilating," "antihypertensive," "incontinence increasing," "Parkinson's disease treating," "dopamine increasing," "catechol-O-methyl transferase inhibiting," "aromatic L-amino acid decarboxylase inhibiting," "dopamine agonist," "neuroprotective," "anticholinergic," "prostate hypertrophy treating", "type II 5-alpha reductase inhibitor," "muscle relaxant," "anti-rheumatoid," "anti-inflammatory," "immunosuppressing," "TNF inhibiting," "antibiotic," "calcineurin inhibitor," "pyrimidine synthesis inhibitor," "5-LO inhibitor," "antifolate," "IL-1 receptor antagonist," "T cell costimulation inhibitor," "autoimmune disorder treating," "myasthemia gravis treating," "antibody suppressing," "anticholinesterase" "kidney disease treating," "antidepressant") formulations and coordinate administration methods are provided which employ an effective amount of a phorbol ester compound of Formula I and one or more secondary or adjunctive agent(s) that is/are combinatorially formulated or coordinately administered with the phorbol ester compound of Formula I to yield a combined, multi-active disease treating composition or coordinate treatment method.

Exemplary combinatorial formulations and coordinate treatment methods in this context employ the phorbol ester of Formula I in combination with the one or more secondary anti-AIDS agent(s), or with one or more adjunctive therapeutic agent(s) that is/are useful for treatment or prophylaxis of the targeted (or associated) disease, condition and/or symptom(s) in the selected combinatorial formulation or coordinate treatment regimen. For most combinatorial formulations and coordinate treatment methods of the invention, a phorbol ester compound of Formula I or related or derivative compound is formulated, or coordinately administered, in combination with one or more secondary or adjunctive therapeutic agent(s), to yield a combined formulation or coordinate treatment method that is combinatorially effective or coordinately useful to treat HIV/AIDS and/or one or more symptom(s) of a opportunistic or secondary disease or condition in the subject. Exemplary combinatorial formulations and coordinate treatment methods in this context employ a phorbol ester compound of Formula I in combination with one or more secondary or adjunctive therapeutic agents selected from, e.g., protease inhibitors, including, but not limited to, saquinavir, indinavir, ritonavir, nelfinavir, atazanavir, darunavir, fosamprenavir, tipranavir and amprenavir; nucleoside reverse transcriptase inhibitors including but not limited to, zidovudine, didanosine, stavudine, lamivudine, zalcitabine, emtricitabine, tenofovir disoproxil fumarate, AVX754 and abacavir; non-nucleoside reverse transcriptase inhibitors including, but not limited to, nevaripine, delavirdine, calanolide A, TMC125 and efavirenz; combination drugs including, but not limited to, efavirenz/emtricitabine/tenofovir disoproxil fumarate, lamivudine/zidovudine, abacavir/lamivudine, abacavir/lamivudine/zidovudine, emtricitabine/tenofovir disoproxil fumarate, sulfamethoxazole/trimethoprim, and lopinavir/ritonavir; entry and fusion inhibitors, including, but not limited to, enfuvirtide, AMD070, BMS-488043, fozivudine tidoxil, GSK-873,140, PRO 140, PRO 542, Peptide T, SCH-D, TNX-355, and UK-427,857; treatments for opportunistic infections and other conditions associated with AIDS and HIV including, but not limited to, acyclovir, adefovir dipivoxil, aldesleukin, amphotericin b, azithromycin, calcium hydroxylapatite, clarithromycin, doxorubicin, dronabinol, entecavir, epoetin alfa, etoposide, fluconazole, ganciclovir, immunoglobulins, interferon alfa-2, isoniazid, itraconazole, megestrol, paclitaxel, peginterferon alfa-2, pentamidine, poly-1-lactic acid, ribavirin, rifabutin, rifampin, somatropin, testosterone, trimetrexate, and valganciclovir; integrase inhibitors including, but not limited to, GS 9137, MK-0518; microbicides, including, but not limited to, BMS-378806, C31G, carbopol 974P, carrageenan, cellulose sulfate, cyanovirin-N, dextran sulfate, hydroxyethyl cellulose, PRO 2000, SPL7013, tenofovir, UC-781, and IL-2.

Additional exemplary combinatorial formulations and coordinate treatment methods may additionally employ the phorbol ester of Formula I in combination with one or more secondary anti-tumor agent(s), or with one or more adjunctive therapeutic agent(s) that is/are useful for treatment or prophylaxis of the targeted (or associated) disease, condition and/or symptom(s) in the selected combinatorial formulation or coordinate treatment regimen. For most combinatorial formulations and coordinate treatment methods of the invention, a phorbol ester compound of Formula I or related or derivative compound is formulated, or coordinately administered, in combination with one or more secondary or adjunctive therapeutic agent(s), to yield a combined formulation or coordinate treatment method that is combinatorially effective or coordinately useful to treat neoplastic diseases and one or more symptom(s) of a secondary disease or condition in the subject. Exemplary combinatorial formulations and coordinate treatment methods in this context employ a phorbol ester compound of Formula I in combination with one or more secondary or adjunctive therapeutic agents selected from, e.g., chemotherapeutic agents, anti-inflammatory agents, doxorubicin, vitamin D3, cytarabine, cytosine arabinoside, daunorubicin, cyclophosphamide, gemtuzumab ozogamicin, idarubicin, mercaptopurine, mitoxantrone, thioguanine, aldesleukin, asparaginase, carboplatin, etoposide phosphate, fludarabine, methotrexate, etoposide, dexamethasone, and choline magnesium trisalicylate. In addition, adjunctive or secondary therapies may be used such as, but not limited to, radiation treatment, hormone therapy and surgery.

Exemplary combinatorial formulations and coordinate treatment methods in the prevention or treatment of side effects from chemotherapy employ the phorbol ester compound of Formula I in combination with one or more additional, chemoprotective or other indicated, secondary or adjunctive therapeutic agents that is/are useful for treatment or prophylaxis of the targeted disease, condition and/or symptom(s). For most combinatorial formulations and coordinate treatment methods of the invention, a phorbol ester compound of Formula I or related or derivative compound is formulated, or coordinately administered, in combination with one or more secondary or adjunctive therapeutic agent(s), to yield a combined formulation or coordinate treatment method that is combinatorially effective or coordinately useful to prevent or treat side effects of chemotherapy in the subject. Exemplary combinatorial formulations and coordinate treatment methods in this context employ a phorbol ester compound of Formula I in combination with one or more secondary or adjunctive therapeutic agents selected from, pegfilgrastim, epoeitn alfa, darbepoetin alfa, alendronate sodium, risedronate, ibandronate, G-CSF, 5-HT$_3$ receptor antagonists, NK$_1$ antagonists, olanzapine, corticosteroids, dopamine antagonists, serotonin antagonists, benzodiazepines, aprepitant, and cannabinoids.

Exemplary combinatorial formulations and coordinate treatment methods in the prevention or treatment of side effects from radiation therapy employ the phorbol ester compound of Formula I in combination with one or more additional, radioprotective or other indicated, secondary or adjunctive therapeutic agents that is/are useful for treatment or prophylaxis of the targeted condition and/or symptom(s). For most combinatorial formulations and coordinate treatment methods of the invention, a phorbol ester compound of Formula I or related or derivative compound is formulated, or coordinately administered, in combination with one or more secondary or adjunctive therapeutic agent(s), to yield a combined formulation or coordinate treatment method that is combinatorially effective or coordinately useful to prevent or treat side effects of radiation therapy in the subject. Exemplary combinatorial formulations and coordinate treatment methods in this context employ a phorbol ester compound of Formula I in combination with one or more secondary or adjunctive therapeutic agents selected from steroids, amifostine, chlorhexidine, benzydamine, sucralfate, keratinocyte growth factor (KGF), palifermin, Cu/Zn superoxide dismutase, Interleukin 11, or prostaglandins.

Exemplary combinatorial formulations and coordinate treatment methods in the prevention or treatment of stoke employ the phorbol ester compound of Formula I in combination with one or more additional, neuroprotective or other indicated, secondary or adjunctive therapeutic agents that is/are useful for treatment or prophylaxis of the targeted disease, condition and/or symptom(s). For most combinatorial formulations and coordinate treatment methods of the invention, a phorbol ester compound of Formula I or related or derivative compound is formulated, or coordinately administered, in combination with one or more secondary or adjunctive therapeutic agent(s), to yield a combined formulation or coordinate treatment method that is combinatorially effective or coordinately useful to prevent or treat stroke, or the effects of stroke. Exemplary combinatorial formulations and coordinate treatment methods in this context employ a phorbol ester compound of Formula I in combination with one or more secondary or adjunctive therapeutic agents selected from tissue plasminogen activator, an anticoagulant, a statin, angiotensin II receptor blockers, angiotensin-converting enzyme inhibitor, beta-blocker, calcium channel blocker, or diuretic.

Exemplary combinatorial formulations and coordinate treatment methods in the prevention or treatment of Parkinson's disease employ the phorbol ester compound of Formula I in combination with one or more additional, neuroprotective or other indicated, secondary or adjunctive therapeutic agents that is/are useful for treatment or prophylaxis of the targeted disease, condition and/or symptom(s). For most combinatorial formulations and coordinate treatment methods of the invention, a phorbol ester compound of Formula I or related or derivative compound is formulated, or coordinately administered, in combination with one or more secondary or adjunctive therapeutic agent(s), to yield a combined formulation or coordinate treatment method that is combinatorially effective or coordinately useful to prevent or treat Parkinson's disease. Exemplary combinatorial formulations and coordinate treatment methods in this context employ a phorbol ester compound of Formula I in combination with one or more secondary or adjunctive therapeutic agents selected from MAO-B inhibitors, pyridoxine, amantidine, pyridoxine, seleyiline, rasagiline, or anticholinergics.

Exemplary combinatorial formulations and coordinate treatment methods in the prevention or treatment of prostate hypertrophy employ the phorbol ester compound of Formula I in combination with one or more indicated, secondary or adjunctive therapeutic agents that is/are useful for treatment or prophylaxis of the targeted disease, condition and/or symptom(s). For most combinatorial formulations and coordinate treatment methods of the invention, a phorbol ester compound of Formula I or related or derivative compound is formulated, or coordinately administered, in combination with one or more secondary or adjunctive therapeutic agent(s), to yield a combined formulation or coordinate treatment method that is combinatorially effective or coordinately useful to prevent or treat prostate hypertrophy. Exemplary combinatorial formulations and coordinate treatment methods in this context employ a phorbol ester compound of Formula I in combination with one or more secondary or adjunctive therapeutic agents selected from finasteride, dutasteride, terazosin, doxazosin, tamsulosin, or an alpha blocker.

Exemplary combinatorial formulations and coordinate treatment methods in the prevention or treatment of rheumatoid arthritis employ the phorbol ester compound of Formula I in combination with one or more additional, anti-rheumatoid or other indicated, secondary or adjunctive therapeutic agents that is/are useful for treatment or prophylaxis of the targeted disease, condition and/or symptom(s). For most combinatorial formulations and coordinate treatment methods of the invention, a phorbol ester compound of Formula I or related or derivative compound is formulated, or coordinately administered, in combination with one or more secondary or adjunctive therapeutic agent(s), to yield a combined formulation or coordinate treatment method that is combinatorially effective or coordinately useful to prevent or treat rheumatoid arthritis. Exemplary combinatorial formulations and coordinate treatment methods in this context employ a phorbol ester compound of Formula I in combination with one or more secondary or adjunctive therapeutic agents selected from non-steroidal anti-inflammatory agent, steroid, disease-modifying anti-rheumatic drug, an immunosuppressant, TNF-α inhibitor, anakinra, abatacept, adalimumab, azathioprine, chloroquine, hydroxychloroquine, ciclosporin, D-penicillamine, etanercept, golimumab, gold salts, infliximab, leflunomide, methotrexate, minocycline, sulfasalazine, rituximab, or tocilizumab.

Exemplary combinatorial formulations and coordinate treatment methods in the prevention or treatment of myasthemia gravis employ the phorbol ester compound of Formula I in combination with one or more indicated, secondary or adjunctive therapeutic agents that is/are useful for treatment or prophylaxis of the targeted disease, condition and/or symptom(s). For most combinatorial formulations and coordinate treatment methods of the invention, a phorbol ester compound of Formula I or related or derivative compound is formulated, or coordinately administered, in combination with one or more secondary or adjunctive therapeutic agent(s), to yield a combined formulation or coordinate treatment method that is combinatorially effective or coordinately useful to prevent or treat myasthemia gravis. Exemplary combinatorial formulations and coordinate treatment methods in this context employ a phorbol ester compound of Formula I in combination with one or more secondary or adjunctive therapeutic agents selected from anticholinesterase, corticosteroid, or immunosuppressive agent.

Exemplary combinatorial formulations and coordinate treatment methods in the prevention or treatment of kidney disease employ the phorbol ester compound of Formula I in combination with one or more anti-incontinent or other indicated, secondary or adjunctive therapeutic agents that is/are useful for treatment or prophylaxis of the targeted disease, condition and/or symptom(s). For most combinatorial formulations and coordinate treatment methods of the invention, a phorbol ester compound of Formula I or related or derivative compound is formulated, or coordinately administered, in combination with one or more secondary or adjunctive therapeutic agent(s), to yield a combined formulation or coordinate treatment method that is combinatorially effective or coordinately useful to prevent or treat kidney disease. Exemplary combinatorial formulations and coordinate treatment methods in this context employ anticholinergic, topical estrogen, imipramine or duloxetine.

In certain embodiments the invention provides combinatorial disease treating ("AIDS treating," "HIV preventing," "HIV treating," "HIV reservoir activating," "Th1 cytokine increasing," "ERK phosphorylation inducing," "apoptosis inducing," "chemotherapeutic," "anti-tumor," "cancer treating," "remission inducing," "remission maintaining," "chemoprotective," "anti-inflammatory," "neutrophil stimulating," "erythropoiesis stimulating," "bone resorbtion inhibiting," "bone strengthening," "antiemetic," "pain relieving," "radiation protective," "anti-swelling," "cytoprotective," "anti-mucositis," "epithelial stimulating," "anti-fibrotic," "platelet stimulating," "stroke treating," "anti-clotting," "anticholesterolemic," "vasodilating," "antihypertensive," "Parkinson's disease treating," "dopamine increasing," "catechol-O-methyl transferase inhibiting," "aromatic L-amino acid decarboxylase inhibiting," "dopamine agonist," "neuroprotective," "anticholinergic," "prostate hypertrophy treating", "type II 5-alpha reductase inhibitor," "muscle relaxant," "anti-rheumatoid," "anti-inflammatory," "immunosuppressing," "TNF inhibiting," "antibiotic," "calcineurin inhibitor," "pyrimidine synthesis inhibitor," "5-LO inhibitor," "antifolate," "IL-1 receptor antagonist," "T cell costimulation inhibitor," "autoimmune disorder treating," "myasthemia gravis treating," "immunosuppressive," "antibody suppressing," "anticholinesterase" "kidney disease treating," "antidepressant") formulations comprising a phorbol ester and one or more adjunctive agent(s) having disease treating activity. Within such combinatorial formulations, a phorbol ester of Formula I and the adjunctive agent(s) having disease treating activity will be present in a combined formulation in disease treating ("AIDS treating," "HIV preventing," "HIV treating," "HIV reservoir activating," "Th1 cytokine increasing," "ERK phosphorylation inducing," "apoptosis inducing," "chemotherapeutic," "anti-tumor," "cancer treating," "remission inducing," "remission maintaining," "chemoprotective," "anti-inflammatory," "neutrophil stimulating," "erythropoiesis stimulating," "bone resorbtion inhibiting," "bone strengthening," "antiemetic," "pain relieving," "radiation protective," "anti-swelling," "cytoprotective," "anti-mucositis," "epithelial stimulating," "anti-fibrotic," "platelet stimulating," "stroke treating," "anti-clotting," "anticholesterolemic," "vasodilating," "antihypertensive," "Parkinson's disease treating," "dopamine increasing," "catechol-O-methyl transferase inhibiting," "aromatic L-amino acid decarboxylase inhibiting," "dopamine agonist," "neuroprotective," "anticholinergic," "prostate hypertrophy treating", "type II 5-alpha reductase inhibitor," "muscle relaxant," "anti-rheumatoid," "anti-inflammatory," "immunosuppressing," "TNF inhibiting," "antibiotic," "calcineurin inhibitor," "pyrimidine synthesis inhibitor," "5-LO inhibitor," "antifolate," "IL-1 receptor antagonist," "T cell costimulation inhibitor," "autoimmune disorder treating," "myasthemia gravis treating," "continence increasing," "antibody suppressing," "anticholinesterase" "kidney disease treating," "antidepressant")) effective amounts, alone or in combination. In exemplary embodiments, a phorbol ester compound of Formula I and a non-phorbol ester agent(s) will each be present in a disease treating/preventing amount (i.e., in singular dosage which will alone elicit a detectable alleviation of symptoms in the subject). Alternatively, the combinatorial formulation may comprise one or both the phorbol ester compound of Formula I and the non-phorbol ester agents in sub-therapeutic singular dosage amount(s), wherein the combinatorial formulation comprising both agents features a combined dosage of both agents that is collectively effective in eliciting a cytopathic disease or condition symptom alleviating response. Thus, one or both of the phorbol ester of Formula I and non-phorbol ester agents may be present in the formulation, or administered in a coordinate administration protocol, at a sub-therapeutic dose, but collectively in the formulation or method they elicit a detectable decrease in symptoms of cytopathic disease in the subject. For example, in some embodiments, the combinatorial formulation may include one or more compounds from a highly active antiretroviral therapy protocol (HAART protocols) in combination with a phorbol ester, among other combinations. Other combinatorial formulations may, for example, include a phorbol ester and/or compounds effective in treating the opportunistic infections of AIDS as well as compounds from HAART protocols. In other embodiments, the combinatorial formulation may include one or more additional chemotherapeutic agents. In a further embodiment, the combinatorial formulation may include one or more additional chemoprotective agents. In other embodiments, the combinatorial formulation may include one or more radioprotective agents. In yet another embodiment, the combinatorial formulation may include one or more neuroprotective agents. In a further embodiment, the combinatorial formulation may include one or more anti-inflammatory agents or other secondary or additional therapeutic agents as described herein.

To practice coordinate administration methods of the invention, a phorbol ester compound of Formula I may be administered, simultaneously or sequentially, in a coordinate treatment protocol with one or more of the secondary or adjunctive therapeutic agents contemplated herein. Thus, in certain embodiments a compound is administered coordinately with a non-phorbol ester agent, or any other secondary or adjunctive therapeutic agent contemplated herein, using separate formulations or a combinatorial formulation as described above (i.e., comprising both a phorbol ester compound of Formula I or related or derivative compound, and a non-phorbol ester therapeutic agent). This coordinate administration may be done simultaneously or sequentially in either order, and there may be a time period while only one or both (or all) active therapeutic agents individually and/or collectively exert their biological activities.

In one embodiment, such coordinate treatment methods may, for example, follow or be derived from various highly active antiretroviral therapy protocols (HAART protocols) and include regimens such as, but not limited to, two nucleoside analogue reverse transcriptase inhibitors plus one or more protease inhibitor or non-nucleoside analogue reverse transcriptase inhibitor with a phorbol ester of Formula I, among other combinations. Other coordinate treatment methods may, for example, include a phorbol ester and/or treatments for opportunistic infections as well as compounds from HAART protocols. A distinguishing aspect of all such coordinate treatment methods is that the phorbol ester compound of Formula I exerts at least some activity, which yields a favorable clinical response in conjunction with a complementary AIDS symptom decreasing, or distinct, clinical response provided by the secondary or adjunctive therapeutic agent. Often, the coordinate administration of the phorbol ester compound of Formula I with the secondary or adjunctive therapeutic agent will yield improved therapeutic or prophylactic results in the subject beyond a therapeutic effect elicited by the phorbol ester compound of Formula I, or the secondary or adjunctive therapeutic agent administered alone. This qualification contemplates both direct effects, as well as indirect effects.

Within exemplary embodiments, a phorbol ester compound of Formula I will be coordinately administered (simultaneously or sequentially, in combined or separate formulation(s)), with one or more secondary HIV treating agents, or other indicated or adjunctive therapeutic agents, e.g., selected from, for example, protease inhibitors, including, but not limited to, saquinavir, indinavir, ritonavir, nelfinavir, atazanavir, darunavir, fosamprenavir, tipranavir and amprenavir; nucleoside reverse transcriptase inhibitors including but not limited to, zidovudine, didanosine, stavudine, lamivudine, zalcitabine, emtricitabine, tenofovir disoproxil fumarate, AVX754 and abacavir; non-nucleoside reverse transcriptase inhibitors including, but not limited to, nevaripine, delavirdine, calanolide A, TMC125 and efavirenz; combination drugs including, but not limited to, efavirenz/emtricitabine/tenofovir disoproxil fumarate, lamivudine/zidovudine, abacavir/lamivudine, abacavir/lamivudine/zidovudine, emtricitabine/tenofovir disoproxil fumarate, sulfamethoxazole/trimethoprim, and lopinavir/ritonavir; entry and fusion inhibitors, including, but not limited to, enfuvirtide, AMD070, BMS-488043, fozivudine tidoxil, GSK-873,140, PRO 140, PRO 542, Peptide T, SCH-D, TNX-355, and UK-427,857; treatments for opportunistic infections and other conditions associated with AIDS and HIV including, but not limited to, acyclovir, adefovir dipivoxil, aldesleukin, amphotericin b, azithromycin, calcium hydroxylapatite, clarithromycin, doxorubicin, dronabinol, entecavir, epoetin alfa, etoposide, fluconazole, ganciclovir, immunoglobulins, interferon alfa-2, isoniazid, itraconazole, megestrol, paclitaxel, peginterferon alfa-2, pentamidine, poly-1-lactic acid, ribavirin, rifabutin, rifampin, somatropin, testosterone, trimetrexate, and valganciclovir; integrase inhibitors including, but not limited to, GS 9137, MK-0518; microbicides, including, but not limited to, BMS-378806, C31G, carbopol 974P, carrageenan, cellulose sulfate, cyanovirin-N, dextran sulfate, hydroxyethyl cellulose, PRO 2000, SPL7013, tenofovir, and UC-781, and IL-2.

In another embodiment, such coordinate treatment methods may, for example, follow or be derived from various chemotherapeutic protocols. Other coordinate treatment methods may, for example, include a phorbol ester and/or treatments for additional symptoms of neoplastic diseases. A distinguishing aspect of all such coordinate treatment methods is that the phorbol ester compound of Formula I exerts at least some activity, which yields a favorable clinical response in conjunction with a complementary neoplastic disease symptom decreasing, or distinct, clinical response provided by the secondary or adjunctive therapeutic agent. Often, the coordinate administration of the phorbol ester compound of Formula I with the secondary or adjunctive therapeutic agent will yield improved therapeutic or prophylactic results in the subject beyond a therapeutic effect elicited by the phorbol ester compound of Formula I, or the secondary or adjunctive therapeutic agent administered alone. This qualification contemplates both direct effects as well as indirect effects.

Within exemplary embodiments, a phorbol ester compound of Formula I will be coordinately administered (simultaneously or sequentially, in combined or separate formulation(s)), with one or more secondary cancer treating agents, or other indicated or adjunctive therapeutic agents, e.g. doxorubicin, vitamin D3, cytarabine, cytosine arabinoside, daunorubicin, cyclophosphamide, gemtuzumab ozogamicin, idarubicin, mercaptopurine, mitoxantrone, thioguanine, aldesleukin, asparaginase, carboplatin, etoposide phosphate, fludarabine, methotrexate, etoposide, dexamethasone, and choline magnesium trisalicylate.

In another embodiment, such coordinate treatment methods may, for example, follow or be derived from various palliative protocols for chemotherapy patients.

Coordinate treatment methods may, for example, include a phorbol ester and/or treatments for additional side effects of chemotherapy. A distinguishing aspect of all such coordinate treatment methods is that the phorbol ester compound of Formula I exerts at least some activity, which yields a favorable clinical response in conjunction with a complementary chemotherapeutic side effect alleviating, or distinct, clinical response provided by the secondary or adjunctive therapeutic agent. Often, the coordinate administration of the phorbol ester compound of Formula I with the secondary or adjunctive therapeutic agent will yield improved therapeutic or prophylactic results in the subject beyond a therapeutic effect elicited by the phorbol ester compound of Formula I, or the secondary or adjunctive therapeutic agent administered alone. This qualification contemplates both direct effects as well as indirect effects.

Within exemplary embodiments, a phorbol ester compound of Formula I will be coordinately administered (simultaneously or sequentially, in combined or separate formulation(s)), with one or more secondary chemotherapeutic side affect alleviating compounds or other indicated or adjunctive therapeutic agents, e.g. pegfilgrastim, epoeitn alfa, darbepoetin alfa, alendronate sodium, risedronate, ibandronate, G-CSF, 5-HT$_3$ receptor antagonists, NK$_1$ antagonists, olanzapine, corticosteroids, dopamine antagonists, serotonin antagonists, benzodiazepines, aprepitant, and cannabinoids.

In another embodiment, such coordinate treatment methods may, for example, follow or be derived from various palliative protocols for radiation therapy patients. Coordinate treatment methods may, for example, include a phorbol ester and/or treatments for additional side effects of radiation therapy. A distinguishing aspect of all such coordinate treatment methods is that the phorbol ester compound of Formula I exerts at least some activity, which yields a favorable clinical response in conjunction with a complementary radiotherapy side effect alleviating, or distinct, clinical response provided by the secondary or adjunctive therapeutic agent. Often, the coordinate administration of the phorbol ester compound of Formula I with the secondary or adjunctive therapeutic agent will yield improved therapeutic or prophylactic results in the subject beyond a therapeutic effect elicited by the phorbol ester compound of Formula I, or the secondary or adjunctive therapeutic agent administered alone. This qualification contemplates both direct effects as well as indirect effects.

Within exemplary embodiments, a phorbol ester compound of Formula I will be coordinately administered (simultaneously or sequentially, in combined or separate formulation(s)), with one or more secondary radiotherapy side affect alleviating compounds or other indicated or adjunctive therapeutic agents, e.g. steroids, amifostine, chlorhexidine, benzydamine, sucralfate, keratinocyte growth factor (KGF), palifermin, Cu/Zn superoxide dismutase, Interleukin 11, or prostaglandins.

In another embodiment, such coordinate treatment methods may, for example, follow or be derived from various protocols for the treatment of stroke. Coordinate treatment methods may, for example, include a phorbol ester and/or treatments for prevention or treatment of damage caused by a stroke. A distinguishing aspect of all such coordinate treatment methods is that the phorbol ester compound of Formula I exerts at least some activity, which yields a favorable clinical response in conjunction with a complementary stroke preventing or treating agent, or distinct, clinical response provided by the secondary or adjunctive therapeutic agent. Often, the coordinate administration of the phorbol ester compound of Formula I with the secondary or adjunctive therapeutic agent will yield improved therapeutic or prophylactic results in the subject beyond a therapeutic effect elicited by the phorbol ester compound of Formula I, or the secondary or adjunctive therapeutic agent administered alone. This qualification contemplates both direct effects as well as indirect effects.

Within exemplary embodiments, a phorbol ester compound of Formula I will be coordinately administered (simultaneously or sequentially, in combined or separate formulation(s)), with one or more secondary stroke treating compounds or other indicated or adjunctive therapeutic agents, e.g. tissue plasminogen activator, an anticoagulant, a statin, angiotensin II receptor blockers, angiotensin-converting enzyme inhibitor, beta-blocker, calcium channel blocker, or diuretic. In addition, adjunctive or secondary therapies may be used in the treatment of stroke or the effects of stroke such as, but not limited to, carotid endarterectomy, angioplasty, stent placement, craniotomny, endovascular coil emobilization, or patent foramen ovale closure.

In another embodiment, such coordinate treatment methods may, for example, follow or be derived from various protocols for the treatment of Parkinson's disease. Coordinate treatment methods may, for example, include a phorbol ester and/or treatments for prevention or treatment of Parkinson's disease. A distinguishing aspect of all such coordinate treatment methods is that the phorbol ester compound of Formula I exerts at least some activity, which yields a favorable clinical response in conjunction with a complementary Parkinson's disease preventing or treating agent, or distinct, clinical response provided by the secondary or adjunctive therapeutic agent. Often, the coordinate administration of the phorbol ester compound of Formula I with the secondary or adjunctive therapeutic agent will yield improved therapeutic or prophylactic results in the subject beyond a therapeutic effect elicited by the phorbol ester compound of Formula I, or the secondary or adjunctive therapeutic agent administered alone. This qualification contemplates both direct effects as well as indirect effects.

Within exemplary embodiments, a phorbol ester compound of Formula I will be coordinately administered (simultaneously or sequentially, in combined or separate formulation(s)), with one or more secondary Parkinson's disease treating compounds or other indicated or adjunctive therapeutic agents, e.g. levodopa, tolcapone, carbidopa, dopamine agonist, MAO-B inhibitors, pyridoxine, amantidine, pyridoxine, seleyiline, rasagiline, or anticholinergics. In addition, adjunctive or secondary therapies may be used in the treatment of Parkinson's disease such as, but not limited to, deep brain stimulation or lesion formation.

In another embodiment, such coordinate treatment methods may, for example, follow or be derived from various protocols for the treatment of prostate hypertrophy. Coordinate treatment methods may, for example, include a phorbol ester and/or treatments for prevention or treatment of prostate hypertrophy. A distinguishing aspect of all such coordinate treatment methods is that the phorbol ester compound of Formula I exerts at least some activity, which yields a favorable clinical response in conjunction with a complementary prostate hypertrophy preventing or treating agent, or distinct, clinical response provided by the secondary or adjunctive therapeutic agent. Often, the coordinate administration of the phorbol ester compound of Formula I with the secondary or adjunctive therapeutic agent will yield improved therapeutic or prophylactic results in the subject beyond a therapeutic effect elicited by the phorbol ester compound of Formula I, or the secondary or adjunctive therapeutic agent administered alone. This qualification contemplates both direct effects as well as indirect effects.

Within exemplary embodiments, a phorbol ester compound of Formula I will be coordinately administered (simultaneously or sequentially, in combined or separate formulation(s)), with one or more secondary prostate hypertrophy treating compounds or other indicated or adjunctive therapeutic agents, e.g. finasteride, dutasteride, terazosin, doxazosin, tamsulosin, or an alpha blocker. In addition, adjunctive or secondary therapies may be used in the treatment of prostate hypertrophy such as, but not limited to, transurethral resection of the prostate, transurethral incision of the prostate, laser surgery, or prostatectomy.

In another embodiment, such coordinate treatment methods may, for example, follow or be derived from various protocols for the treatment of rheumatoid arthritis. Coordinate treatment methods may, for example, include a phorbol ester and/or treatments for the prevention or treatment of rheumatoid arthritis. A distinguishing aspect of all such coordinate treatment methods is that the phorbol ester compound of Formula I exerts at least some activity, which yields a favorable clinical response in conjunction with a complementary rheumatoid arthritis preventing or treating agent, or distinct, clinical response provided by the secondary or adjunctive therapeutic agent. Often, the coordinate administration of the phorbol ester compound of Formula I with the secondary or adjunctive therapeutic agent will yield improved therapeutic or prophylactic results in the subject beyond a therapeutic effect elicited by the phorbol ester compound of Formula I, or the secondary or adjunctive therapeutic agent administered alone. This qualification contemplates both direct effects as well as indirect effects.

Within exemplary embodiments, a phorbol ester compound of Formula I will be coordinately administered (simultaneously or sequentially, in combined or separate formulation(s)), with one or more secondary rheumatoid arthritis treating compounds or other indicated or adjunctive therapeutic agents, e.g. non-steroidal anti-inflammatory agent, steroid, disease-modifying anti-rheumatic drug, an immunosuppressant, TNF-α inhibitor, anakinra, abatacept, adalimumab, azathioprine, chloroquine, hydroxychloroquine, ciclosporin, D-penicillamine, etanercept, golimumab, gold salts, infliximab, leflunomide, methotrexate, minocycline, sulfasalazine, rituximab, or tocilizumab.

In another embodiment, such coordinate treatment methods may, for example, follow or be derived from various protocols for the treatment of autoimmune disease. Coordinate treatment methods may, for example, include a phorbol ester and/or treatments for the prevention or treatment of myasthemia gravis. A distinguishing aspect of all such coordinate treatment methods is that the phorbol ester compound of Formula I exerts at least some activity, which yields a favorable clinical response in conjunction with a complementary myasthemia gravis preventing or treating agent, or distinct, clinical response provided by the secondary or adjunctive therapeutic agent. Often, the coordinate administration of the phorbol ester compound of Formula I with the secondary or adjunctive therapeutic agent will yield improved therapeutic or prophylactic results in the subject beyond a therapeutic effect elicited by the phorbol ester compound of Formula I, or the secondary or adjunctive therapeutic agent administered alone. This qualification contemplates both direct effects as well as indirect effects.

Within exemplary embodiments, a phorbol ester compound of Formula I will be coordinately administered (simultaneously or sequentially, in combined or separate formulation(s)), with one or more secondary myasthemia gravis treating compounds or other indicated or adjunctive therapeutic agents, e.g. anticholinesterase, corticosteroid, or immunosuppressive agent.

In another embodiment, such coordinate treatment methods may, for example, follow or be derived from various protocols for the treatment of kidney disease. Coordinate treatment methods may, for example, include a phorbol ester and/or treatments for the prevention or treatment of kidney disease and symptoms of kidney disease. A distinguishing aspect of all such coordinate treatment methods is that the phorbol ester compound of Formula I exerts at least some activity, which yields a favorable clinical response in conjunction with a complementary kidney disease preventing or treating agent, or distinct, clinical response provided by the secondary or adjunctive therapeutic agent. Often, the coordinate administration of the phorbol ester compound of Formula I with the secondary or adjunctive therapeutic agent will yield improved therapeutic or prophylactic results in the subject beyond a therapeutic effect elicited by the phorbol ester compound of Formula I, or the secondary or adjunctive therapeutic agent administered alone. This qualification contemplates both direct effects as well as indirect effects.

Within exemplary embodiments, a phorbol ester compound of Formula I will be coordinately administered (simultaneously or sequentially, in combined or separate formulation(s)), with one or more secondary kidney disease treating compounds or other indicated or adjunctive therapeutic agents, e.g. anticholinergic, topical estrogen, imipramine or duloxetine.

In another embodiment, such coordinate treatment methods may, for example, follow or be derived from various protocols for the treatment of urinary incontinence. Coordinate treatment methods may, for example, include a phorbol ester and/or treatments for the prevention or treatment of urinary incontinence. A distinguishing aspect of all such coordinate treatment methods is that the phorbol ester compound of Formula I exerts at least some activity, which yields a favorable clinical response in conjunction with a complementary urinary incontinence preventing or treating agent, or distinct, clinical response provided by the secondary or adjunctive therapeutic agent. Often, the coordinate administration of the phorbol ester compound of Formula I with the secondary or adjunctive therapeutic agent will yield improved therapeutic or prophylactic results in the subject beyond a therapeutic effect elicited by the phorbol ester compound of Formula I, or the secondary or adjunctive therapeutic agent administered alone. This qualification contemplates both direct effects as well as indirect effects.

Within exemplary embodiments, a phorbol ester compound of Formula I will be coordinately administered (simultaneously or sequentially, in combined or separate formulation(s)), with one or more secondary urinary incontinence treating compounds or other indicated or adjunctive therapeutic agents, e.g. anticholinergic, topical estrogen, imipramine or duloxetine.

As noted above, in all of the various embodiments of the invention contemplated herein, the disease treating methods and formulations may employ a phorbol ester compound of Formula I in any of a variety of forms, including any one or combination of the subject compound's pharmaceutically acceptable salts, solvates, isomers, enantiomers, polymorphs, solvates, hydrates, and/or prodrugs. In exemplary embodiments of the invention, TPA is employed within the therapeutic formulations and methods for illustrative purposes.

The pharmaceutical compositions of the present invention may be administered by any means that achieve their intended therapeutic or prophylactic purpose. Suitable routes of administration for the compositions of the invention include, but are not limited to, conventional delivery routes, devices and methods including injectable methods such as, but not limited to, intravenous, intramuscular, intraperitoneal, intraspinal, intrathecal, intracerebroventricular, intraarterial, subcutaneous and intranasal routes.

The compositions of the present invention may further include a pharmaceutically acceptable carrier appropriate for the particular mode of administration being employed. Dosage forms of the compositions of the present invention include excipients recognized in the art of pharmaceutical compounding as being suitable for the preparation of dosage units as discussed above. Such excipients include, without intended limitation, binders, fillers, lubricants, emulsifiers, suspending agents, sweeteners, flavorings, preservatives, buffers, wetting agents, disintegrants, effervescent agents and other conventional excipients and additives.

If desired, the compositions of the invention can be administered in a controlled release form by use of a slow release carrier, such as a hydrophilic, slow release polymer. Exemplary controlled release agents in this context include, but are not limited to, hydroxypropyl methyl cellulose, having a viscosity in the range of about 100 cps to about 100,000 cps or other biocompatible matrices such as cholesterol.

Some phorbol ester compositions of Formula I of the invention are designed for parenteral administration, e.g. to be administered intravenously, intramuscularly, subcutaneously or intraperitoneally, including aqueous and non-aqueous sterile injectable solutions which, like many other contemplated compositions of the invention, may optionally contain anti-oxidants, buffers, bacteriostats and/or solutes which render the formulation isotonic with the blood of the mammalian subject; and aqueous and non-aqueous sterile suspensions which may include suspending agents and/or thickening agents. The formulations may be presented in unit-dose or multi-dose containers. Additional compositions and formulations of the invention may include polymers for extended release following parenteral administration. The parenteral preparations may be solutions, dispersions or emulsions suitable for such administration. The subject agents may also be formulated into polymers for extended release following parenteral administration. Pharmaceutically acceptable formulations and ingredients will typically be sterile or readily sterilizable, biologically inert, and easily administered. Such polymeric materials are well known to those of ordinary skill in the pharmaceutical compounding arts. Parenteral preparations typically contain buffering agents and preservatives, and injectable fluids that are pharmaceutically and physiologically acceptable such as water, physiological saline, balanced salt solutions, aqueous dextrose, glycerol or the like. Extemporaneous injection solutions, emulsions and suspensions may be prepared from sterile powders, granules and tablets of the kind previously described. Preferred unit dosage formulations are those containing a daily dose or unit, daily sub-dose, as described herein above, or an appropriate fraction thereof, of the active ingredient(s).

In more detailed embodiments, compositions of the invention may comprise a phorbol ester compound of Formula I encapsulated for delivery in microcapsules, microparticles, or microspheres, prepared, for example, by coacervation techniques or by interfacial polymerization, for example, hydroxymethylcellulose or gelatin-microcapsules and poly(methylmethacylate) microcapsules, respectively; in colloidal drug delivery systems (for example, liposomes, albumin microspheres, microemulsions, nano-particles and nanocapsules); or within macroemulsions.

As noted above, in certain embodiments the methods and compositions of the invention may employ pharmaceutically acceptable salts, e.g., acid addition or base salts of the above-described phorbol ester compounds of Formula I and/or related or derivative compounds. Examples of pharmaceutically acceptable addition salts include inorganic and organic acid addition salts. Suitable acid addition salts are formed from acids which form non-toxic salts, for example, hydrochloride, hydrobromide, hydroiodide, sulphate, hydrogen sulphate, nitrate, phosphate, and hydrogen phosphate salts. Additional pharmaceutically acceptable salts include, but are not limited to, metal salts such as sodium salts, potassium salts, cesium salts and the like; alkaline earth metals such as calcium salts, magnesium salts and the like; organic amine salts such as triethylamine salts, pyridine salts, picoline salts, ethanolamine salts, triethanolamine salts, dicyclohexylamine salts, N,N'-dibenzylethylenediamine salts and the like; organic acid salts such as acetate, citrate, lactate, succinate, tartrate, maleate, fumarate, mandelate, acetate, dichloroacetate, trifluoroacetate, oxalate, and formate salts; sulfonates such as methanesulfonate, benzenesulfonate, and p-toluenesulfonate salts; and amino acid salts such as arginate, asparginate, glutamate, tartrate, and gluconate salts. Suitable base salts are formed from bases that form non-toxic salts, for example aluminum, calcium, lithium, magnesium, potassium, sodium, zinc and diethanolamine salts.

Other detailed embodiments, the methods and compositions of the invention for employ prodrugs of phorbol esters of Formula I. Prodrugs are considered to be any covalently bonded carriers which release the active parent drug in vivo. Examples of prodrugs useful within the invention include esters or amides with hydroxyalkyl or aminoalkyl as a substituent, and these may be prepared by reacting such compounds as described above with anhydrides such as succinic anhydride.

The invention disclosed herein will also be understood to encompass methods and compositions comprising phorbol esters of Formula I using in vivo metabolic products of the said compounds (either generated in vivo after administration of the subject precursor compound, or directly administered in the form of the metabolic product itself). Such products may result for example from the oxidation, reduction, hydrolysis, amidation, esterification and the like of the administered compound, primarily due to enzymatic processes. Accordingly, the invention includes methods and compositions of the invention employing compounds produced by a process comprising contacting a phorbol ester compound of Formula I with a mammalian subject for a period of time sufficient to yield a metabolic product thereof. Such products typically are identified by preparing a radiolabelled compound of the invention, administering it parenterally in a detectable dose to an animal such as rat, mouse, guinea pig, monkey, or to man, allowing sufficient time for metabolism to occur and isolating its conversion products from the urine, blood or other biological samples.

The invention disclosed herein will also be understood to encompass diagnostic compositions for diagnosing the risk level, presence, severity, or treatment indicia of, or otherwise managing diseases including, but not limited to, neoplastic diseases including malignant neoplastic diseases such as leukemia, stroke, Parkinson's disease, myasthemia gravis, rheumatoid arthritis, kidney disease, prostate hypertrophy, and an AIDS or a related disease or condition in a mammalian subject, comprising contacting a labeled (e.g., isotopically labeled, fluorescent labeled or otherwise labeled to permit detection of the labeled compound using conventional methods) phorbol ester compound of Formula I to a mammalian subject (e.g., to a cell, tissue, organ, or individual) at risk or presenting with one or more symptom(s) of cancer, stroke, Parkinson's disease, myasthemia gravis, rheumatoid arthritis, kidney disease, prostate hypertrophy, and/or AIDS, and thereafter detecting the presence, location, metabolism, and/or binding state (e.g., detecting binding to an unlabeled binding partner involved in HIV receptor physiology/metabolism or malignant cell receptor physiology/metabolism) of the labeled compound using any of a broad array of known assays and labeling/detection methods. In exemplary embodiments, a phorbol ester compound of Formula I is isotopically-labeled by having one or more atoms replaced by an atom having a different atomic mass or mass number.

Examples of isotopes that can be incorporated into the disclosed compounds include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. The isotopically-labeled compound is then administered to an individual or other subject and subsequently detected as described above, yielding useful diagnostic and/or therapeutic management data, according to conventional techniques.

EXAMPLES

The experiments described below demonstrate novel and powerful uses for phorbol esters and derivative compounds as HIV treating drugs that can effectively decrease the symptoms of AIDS. In exemplary clinical trials, individuals who were unresponsive to traditional treatments for HIV and AIDS were responsive to treatments with TPA. The treatment with TPA was allowed as "compassionate" and recovery of some patients was considered life-saving according to the attending physicians. The experiments described below additionally demonstrate the usefulness of phorbol esters and derivative compounds in the treatment of neoplastic diseases, as chemoprotectants, radioprotectants, in the treatment of stroke, Parkinson's disease, prostate hypertrophy, rheumatoid arthritis, kidney disease, urinary incontinence and myasthemia gravis. Phorbol esters have additionally provided unexpected cosmetic results in the form of decreasing the appearance of dark circles and increasing the youthfulness of the skin. These and additional findings are further expanded and elucidated within the following examples.

Example I

Effect of TPA on the Peripheral White Blood Cells (WBC) and Hemoglobin (Hb) Counts in S180 Cell-Injected Mice Sarcoma 180 (S180) cells were injected into Kwen-Ming mice. On the third day, the mice were given TPA interperitoneally (i.p.). at 50, 100 or 200 µg/kg/day for 7 days. On the second day after the treatment was completed, blood samples were taken from the tails of the treated mice for WBC and Hb analyses. The WBC counts for the treated groups (50, 100, or 200 ug/kg/day for 7 days) were 16.1±7.4, 18.7±0.3.0 and 20.7±0.3.4×$10^9$/L, respectively; the WBC count for the control group was 13.6±1.8×$10^9$/L. The Hb of the treated groups were 136±11, 149±12 and 149±10 g/L, and the Hb of the control group was 134+−15 g/L. The results indicate that i.p. injection of TPA could increase the peripheral WBC counts in mice in a dose-dependent manner, whereas the Hb levels were not greatly affected in TPA treated mice when compared to the control mice.

Example II

Dose Ranging Study

Due to the strong local irritation caused by TPA application, TPA was given to patients by intravenous (i.v.) infusion. TPA solution in a sterile syringe was injected into 200 ml of sterile saline and mixed well for i.v. infusion.

The Toxicity and Side Effects of Different TPA Doses Administered Clinically:

(1) TPA Given at 1 mg/Patient/Week:

One mg TPA in solution was mixed well with 200 ml of sterile saline for intravenous infusion which was completed in 1 h at the rate of 16 µg/min. One hour after TPA administration, patients started to have chills which lasted for about 30 min, followed by fever, (the patients' temperature reached 37.5-39.5° C. which lasted for 3-5 h, then returned to normal) with light to heavy perspiration. The above symptoms could be alleviated by giving the patients glucocorticoids. TPA at this dose caused a minority of patients to bleed, several patients suffered for a short period of time difficulty in breathing, and Hb was detected in the urine. However, these side effects were short lived and reversible. The cardiac, hepatic, renal and pulmonary functions were all found to be normal.

(2) TPA Given at 0.5 mg/Patient×2/Week: (Two Doses a Week)

0.5 mg of TPA in solution was mixed well with 200 ml of saline for intravenous infusion which was completed in 1 h at the rate of 8 µg/min. The reactions after administration were similar to that of the 1 mg TPA dosage, but to a lesser extent than the 1 mg dose. The patients tolerated the lower dose more easily. Occasionally, Hb was detected in patients' urine. Difficulty in breathing was not observed. The cardiac, hepatic, renal and pulmonary functions were all normal.

(3) TPA Given at 0.25 mg/Patient×4/Week:

0.25 mg of TPA in solution was mixed well with 200 ml of saline for intravenous infusion which was completed in 1 h at the rate of 4 µg/min. After administration, symptoms such as chills and fever were also observed, but to a much lesser extent than with the higher dosages. No Hb was detected in the urine, and no patient suffered difficulty in breathing. The cardiac, hepatic, renal and pulmonary functions were all normal.

Example III

First Clinical Study of HIV+Patients Treated with TPA

Twelve symptomatic patients (five males and seven females) between the ages of 35 to 52 all of whom were infected with HIV in 1995 through blood transfusion and were refractory to standard treatments for HIV were treated with TPA. Each patient was administered a weight adjusted dosage of TPA (75 µg/sq m) in 200 ml of sterile saline by i.v. over one hour. This dose was administered once daily for the first three days of treatment. Each patient was then given this dose every other day for days 4 to 18 followed by a six month rest period prior to a second course of treatment according to the same protocol.

Blood samples were gathered prior to administration of the first dose of TPA and on days 4 and 40 of the treatment cycle. Levels of CD3, CD4 and CD8 in peripheral blood were measured using monoclonal antibodies (Becton Dickson Scientific Co., Franklin Lakes, N.J.) and a flow cytometer (B.D. Bioscience, San Diego, Calif.).

As can be seen in Table 1, no consistent change or correlation was observed in CD3, CD4, or CD8 levels.

TABLE ONE

CD$_4$ CD$_8$ CD$_3$ TEST RESULTS OF TWELVE HIV PATIENTS

| PATIENT NO | TEST TIME | CD$_4$ | CD$_8$ | CD$_3$ |
|---|---|---|---|---|
| 01-1 | Before TPA | 3 | 196 | 341 |
| 01-2 | Four days after TPA | 3 | 180 | 299 |
| 01-3 | Forty two days after TPA | 2 | 111 | 203 |
| 02-1 | Before TPA | 26 | 614 | 687 |
| 02-2 | Four days after TPA | 105 | <2000 | 2616 |
| 02-3 | Forty two days after TPA | 54 | 700 | 799 |
| 03-1 | Before TPA | 32 | 524 | 543 |
| 03-2 | Four days after TPA | 36 | 366 | 427 |
| 03-3 | Forty two days after TPA | 33 | 374 | 424 |
| 04-1 | Before TPA | 173 | 735 | 975 |
| 04-2 | Four days after TPA | 123 | 770 | 941 |
| 04-3 | Forty two days after TPA | 44 | 493 | 581 |
| 05-1 | Before TPA | 106 | 1556 | 1646 |
| 05-2 | Four days after TPA | 119 | 1330 | 1282 |
| 05-3 | Forty two days after TPA | 191 | 1429 | 1643 |
| 06-1 | Before TPA | 232 | 865 | 1221 |
| 06-2 | Four days after TPA | 179 | 570 | 808 |
| 06-3 | Forty two days after TPA | 49 | 429 | 537 |
| 07-1 | Before TPA | 10 | 988 | 1022 |
| 07-2 | Four days after TPA | 7 | 570 | 598 |
| 07-3 | Forty two days after TPA | 1 | 139 | 146 |
| 08-1 | Before TPA | 524 | 725 | 1332 |
| 08-2 | Four days after TPA | 318 | 355 | 739 |
| 08-3 | Forty two days after TPA | 241 | 527 | 868 |
| 09-1 | Before TPA | 442 | 1021 | 1479 |
| 09-2 | After TPA | 663 | <2000 | 2920 |
| 10-1 | Before TPA | 407 | 328 | 778 |
| 10-2 | After TPA | 445 | 591 | 1077 |
| 11-1 | Before TPA | 40 | 322 | 373 |
| 11-2 | After TPA | 131 | 724 | 874 |
| 12-1 | Before TPA | 84 | 256 | 375 |
| 12-2 | After TPA | 78 | 268 | 362 |

As can be seen in Table 2, below, there were similarly inconsistent results in the change of viral load with five patients having an increase in HIV and no change or a reduction in seven others.

TABLE TWO

BLOOD HIV COUNT OF THE TWELVE PATIENTS BEFORE DURING AND AFTER THE TPA TREATMENT

| PATIENT NO | TEST TIME | RESULTS (copies/ml) | LOG VALUE | FOOT NOTE |
|---|---|---|---|---|
| 01-1 | 3 days before TPA | $3.36 \times 10^5$ | 5.526 | |
| 01-2 | 4 days after initial TPA | $1.14 \times 10^4$ | 6.151 | |
| 01-3 | 15 days after initial TPA | $2.02 \times 10^4$ | 4.306 | |
| 01-4 | 25 days after initial TPA | $2.60 \times 10^4$ | 4.416 | |
| 02-1 | 3 days before TPA | $9.97 \times 10^4$ | 4.999 | |
| 02-2 | 4 days after initial TPA | $9.72 \times 10^6$ | 6.899 | |
| 02-3 | 15 days after initial TPA | $6.33 \times 10^6$ | 6.801 | |
| 02-4 | 25 days after initial TPA | $8.72 \times 10^6$ | 6.941 | |
| 03-1 | 3 days before TPA | $3.77 \times 10^5$ | 5.577 | |
| 03-2 | 4 days after initial TPA | $8.13 \times 10^4$ | 4.910 | |
| 03-3 | 15 days after initial TPA | $6.11 \times 10^3$ | 3.786 | |
| 03-4 | 25 days after initial TPA | $8.59 \times 10^5$ | 5.934 | |
| 04-1 | 3 days before TPA | $1.11 \times 10^6$ | 6.045 | |
| 04-2 | 4 days after initial TPA | $1.75 \times 10^7$ | 7.243 | |
| 04-3 | 15 days after initial TPA | $1.11 \times 10^6$ | 6.614 | |
| 04-4 | 25 days after initial TPA | $1.21 \times 10^4$ | 4.084 | |
| 05-1 | 3 days before TPA | $2.49 \times 10^4$ | 6.637 | |
| 05-2 | 4 days after initial TPA | $9.42 \times 10^5$ | 5.974 | |
| 05-3 | 15 days after initial TPA | $2.34 \times 10^7$ | 7.369 | |
| 05-4 | 25 days after initial TPA | $5.56 \times 10^6$ | 6.745 | |
| 06-1 | 3 days before TPA | $4.57 \times 10^5$ | 5.660 | |
| 06-2 | 4 days after initial TPA | $1.44 \times 10^4$ | 4.160 | |
| 06-3 | 15 days after initial TPA | $1.88 \times 10^5$ | 5.274 | |
| 06-4 | 7 days after TPA | $2.28 \times 10^6$ | 6.357 | |
| 07-1 | 3 days before TPA | $2.40 \times 10^5$ | 5.623 | |
| 07-2 | 4 days after initial TPA | $1.51 \times 10^5$ | 5.179 | |
| 07-3 | 15th day during TPA | $9.74 \times 10^4$ | 4.988 | |
| 07-4 | 25 days after initial TPA | $5.30 \times 10^3$ | 3.724 | |
| 08-1 | 3 days before TPA | $8.02 \times 10^5$ | 5.904 | |
| 08-2 | 4 days after initial TPA | $9.09 \times 10^5$ | 5.959 | |
| 08-3 | 15 days after initial TPA | $5.46 \times 10^6$ | 6.737 | |
| 08-4 | 25 days after initial TPA | $7.77 \times 10^6$ | 6.890 | |
| 09-1 | 3 days before TPA | undetectable | | |
| 09-2 | 25 days after TPA | undetectable | | |
| 10-1 | 3 days before TPA | $1.51 \times 10^4$ | 4.180 | Sample taken from the second cycle treatment |
| 10-2 | 25 days after initial TPA | $2.79 \times 10^4$ | 4.446 | |
| 11-1 | 3 days before TPA | $1.59 \times 10^5$ | 5.201 | Sample taken from the second cycle treatment |
| 11-2 | 25 days after initial TPA | $1.25 \times 10^5$ | 5.096 | |
| 12-1 | 3 days before TPA | $1.32 \times 10^4$ | 4.122 | Sample taken from the second cycle treatment |
| 12-2 | 25 days after initial TPA | $6.27 \times 10^3$ | 3.798 | |

Despite the lack of correlation with viral and CD3, CD4 and CD9 levels, eleven of the patients showed significant improvement following treatment. Eight patients became symptom free and five of them have been in remission for 6 to 12 months. Three additional patients had a decrease in symptoms.

Example IV

Second Clinical Study of HIV+Patients Treated with TPA

Nine of the patients in Example III were given a second treatment of TPA. Of these nine, seven were asymptomatic at the beginning of the second trial. A tenth patient (patient #2a) who was symptomatic and had not previously been treated with TPA was added to the study. Each patient was administered a weight adjusted dosage of TPA (75 µg/sq m) in 200 ml of sterile saline intravenously over one hour. This dosage was given to each patient once a day for ten consecutive days followed by a rest period of ten days for three cycles and a total of 30 doses of TPA. Patients 5a, 6a, and 8a stopped taking anti-AIDS drugs one month prior to beginning the TPA treatment and beginning again one month after the third cycle. Patients 1-4a, 7a, and 9a-10a continued taking anti-AIDS drugs throughout the treatment.

Blood samples were taken three days prior to starting treatment, after completing the first 10 day cycle of TPA infusion and again after the last TPA infusion and CD3, CD4, CD8, WBC, RBC, HGB and platelets were measured.

As shown in Table 3, there was an increase in CD3 in all patients after the first and third infusion with TPA with the highest value occurring after the third cycle, with the exception of two patients (5a & 10a). There was a trend for increases in the CD8 and in CD4. These results suggest a strengthening of the immune systems with TPA treatment. Varied results were obtained in the HIV count (Table 4). The HIV measurements in some of the patients were below the limits of detection of the method (less than 200) while it increased somewhat in others. There was normal variation in the measurement of WBC, RBC, HGB and platelets (Table 5).

TABLE THREE $CD_4$ $CD_8$ $CD_3$ TEST RESULTS OF 10 HIV PATIENTS

| PATIENT NO | TEST TIME | $CD_4$ | $CD_8$ | $CD_3$ |
|---|---|---|---|---|
| 01-1 | Before TPA | 5 | 576 | 1071 |
| 01-2 | After first 10-day TPA infusion cycle | 7 | 907 | 1323 |
| 01-3 | After third 10-day TPA infusion cycle | 19 | 1129 | 2037 |
| 02a-1 | Before TPA | 26 | 307 | 339 |
| 02a-2 | After first 10-day TPA infusion cycle | 76 | 335 | 476 |
| 02a-3 | After third 10-day TPA infusion cycle | 137 | 543 | 625 |
| 03a-1 | Before TPA | 295 | 571 | 870 |
| 03a-2 | After first 10-day TPA infusion cycle | 460 | 729 | 1200 |
| 03a-3 | After third 10-day TPA infusion cycle | 1002 | 980 | 2033 |
| 04a-1 | Before TPA | 152 | 672 | 896 |
| 04a-2 | After first 10-day TPA infusion cycle | 189 | 584 | 823 |
| 04a-3 | After third 10-day TPA infusion cycle | 205 | 916 | 1193 |
| 05a-1 | Before TPA | 92 | 1097 | 1175 |
| 05a-2 | After first 10-day TPA infusion cycle | 91 | 1507 | 1598 |
| 05a-3 | After third 10-day TPA infusion cycle | 94 | 1127 | 1257 |
| 06a-1 | Before TPA | 230 | 378 | 669 |
| 06a-2 | After first 10-day TPA infusion cycle | 285 | 429 | 758 |
| 06a-3 | After third 10-day TPA infusion cycle | 276 | 466 | 938 |
| 07a-1 | Before TPA | 567 | 1736 | 2258 |
| 07a-2 | After first 10-day TPA infusion cycle | 729 | >2000 | 3148 |
| 07a-3 | After third 10-day TPA infusion cycle | 786 | >2000 | 3347 |
| 08a-1 | Before TPA | 361 | 569 | 1023 |
| 08a-2 | After first 10-day TPA infusion cycle | 519 | 547 | 1143 |
| 08a-3 | After third 10-day TPA infusion cycle | 495 | 733 | 1295 |
| 09a-1 | Before TPA | 101 | 533 | 672 |
| 09a-2 | After first 10-day TPA infusion cycle | 136 | 574 | 712 |
| 09a-3 | After third 10-day TPA infusion cycle | 100 | 1221 | 1317 |
| 10a-1 | Before TPA | 49 | 178 | 240 |
| 10a-2 | After first 10-day TPA infusion cycle | 74 | 261 | 333 |
| 10a-3 | After third 10-day TPA infusion cycle | 63 | 208 | 308 |

TABLE FOUR

BLOOD HIV COUNT OF THE TEN PATIENTS BEFORE DURING AND AFTER THE THREE TEN-DAY TPA INFUSION

| PATIENT NO | TEST TIME | RESULTS (copies/ml) | LOG VALUE |
|---|---|---|---|
| 01-1 | 3 days before TPA | $4.57 \times 10^6$ | 6.660 |
| 01-2 | after first cycle TPA infusion | $2.99 \times 10^5$ | 5.475 |
| 01-3 | after third cycle TPA infusion | $9.41 \times 10^5$ | 5.973 |
| 02a-1 | 3 days before TPA | $2.71 \times 10^5$ | 5.433 |
| 02a-2 | after first cycle TPA infusion | $3.09 \times 10^5$ | 5.490 |
| 02a-3 | after third cycle TPA infusion | $9.24 \times 10^5$ | 5.966 |
| 03a-1 | 3 days before TPA | undetectable | — |
| 03a-2 | after first cycle TPA infusion | lower the 500 | 2.371 |
| 03a-3 | after third cycle TPA infusion | $9.55 \times 10^3$ | 3.980 |
| 04a-1 | 3 days before TPA | lower than 500 | 2.312 |
| 04a-2 | after first cycle TPA infusion | undetectable | — |
| 04a-3 | after third cycle TPA infusion | $2.38 \times 10^3$ | 3.376 |
| 05a-1 | 3 days before TPA | undetectable | — |
| 05a-2 | after first cycle TPA infusion | undetectable | — |
| 05a-3 | after third cycle TPA infusion | undetectable | — |
| 06a-1 | 3 days before TPA | undetectable | — |
| 06a-2 | after first cycle TPA infusion | undetectable | — |
| 06a-3 | after third cycle TPA infusion | undetectable | — |
| 07a-1 | 3 days before TPA | undetectable | — |
| 07a-2 | after first cycle TPA infusion | undetectable | — |
| 07a-3 | after third cycle TPA infusion | undetectable | — |
| 08a-1 | 3 days before TPA | $1.13 \times 10^4$ | 4.054 |
| 08a-2 | after first cycle TPA infusion | $6.68 \times 10^4$ | 4.825 |
| 08a-3 | after third cycle TPA infusion | $6.20 \times 10^4$ | 4.792 |
| 09a-1 | 3 days before TPA | $1.38 \times 10^5$ | 5.139 |
| 09a-2 | after first cycle TPA infusion | $1.65 \times 10^5$ | 5.217 |
| 09a-3 | after third cycle TPA infusion | $2.35 \times 10^5$ | 5.371 |
| 10a-1 | 3 days before TPA | $7.20 \times 10^5$ | 5.857 |
| 10a-2 | after first cycle TPA infusion | $2.82 \times 10^5$ | 5.450 |
| 10a-3 | after third cycle TPA infusion | $1.86 \times 10^5$ | 5.270 |

TABLE FIVE

PERIPHERY BLOOD COUNT OF THE TEN PATIENTS BEFORE
AND AFTER THE TPA THREE 10-DAY TREATMENT

| PATIENT NO | TEST TIME | WBC (×10⁹/L) | RBC (×10¹²/L) | HGB (g/L) | PLt (×10⁹/L) |
|---|---|---|---|---|---|
| 01-1 | Before TPA | 2.3 | 2.55 | 92 | 199 |
| 01-2 | After first 10-day TPA infusing | 4.4 | 2.61 | 99 | 325 |
| 01-3 | After third 10-day TPA infusing | 6.1 | 2.91 | 102 | 182 |
| 02a-1 | Before TPA | 5.7 | 2.44 | 114 | 227 |
| 02a-2 | After first 10-day TPA infusing | 3.7 | 2.14 | 88 | 238 |
| 02a-3 | After third 10-day TPA infusing | 11.1 | 2.52 | 100 | 124 |
| 03a-1 | Before TPA | 7.8 | 4.04 | 147 | 309 |
| 03a-2 | After first 10-day TPA infusing | 9.8 | 3.83 | 1.38 | 338 |
| 03a-3 | After third 10-day TPA infusing | 13.6 | 4.54 | 140 | 549 |
| 04a-1 | Before TPA | 3.9 | 3.34 | 127 | 232 |
| 04a-2 | After first 10-day TPA infusing | 3.6 | 2.92 | 107 | 306 |
| 04a-3 | After third 10-day TPA infusing | 9.2 | 2.85 | 105 | 105 |
| 05a-1 | Before TPA | 5.1 | 3.54 | 146 | 243 |
| 05a-2 | After first 10-day TPA infusing | 5.7 | 3.46 | 1.35 | 315 |
| 05a-3 | After third 10-day TPA infusing | 10.1 | 3.61 | 144 | 130 |
| 06a-1 | Before TPA | 5.0 | 4.21 | 171 | 198 |
| 06a-2 | After first 10-day TPA infusing | 4.2 | 3.48 | 142 | 256 |
| 06a-3 | After third 10-day TPA infusing | 6.5 | 3.66 | 154 | 169 |
| 07a-1 | Before TPA | 6.6 | 3.62 | 102 | 306 |
| 07a-2 | After first 10-day TPA infusing | 6.0 | 3.76 | 143 | 258 |
| 07a-3 | After third 10-day TPA infusing | 6.0 | 3.92 | 123 | 293 |
| 08a-1 | Before TPA | 3.1 | 4.03 | 125 | 116 |
| 08a-2 | After first 10-day TPA infusing | 4.3 | 3.86 | 128 | 221 |
| 08a-3 | After third 10-day TPA infusing | 6.8 | 4.19 | 128 | 138 |
| 09a-1 | Before TPA | 3.5 | 1.43 | 41 | 114 |
| 09a-2 | After first 10-day TPA infusing | 2.6 | 1.99 | 57 | 214 |
| 09a-3 | After third 10-day TPA infusing | 4.0 | 2.33 | 67 | 170 |
| 10a-1 | Before TPA | 2.6 | 2.65 | 78 | 297 |
| 10a-2 | After first 10-day TPA infusing | 2.9 | 2.58 | 92 | 187 |
| 10a-3 | After third 10-day TPA infusing | 7.0 | 4.31 | 130 | 138 |

Of nine patients previously treated with TPA in the first clinical study, only one (#9a) presented with some AIDS symptoms prior to the start of the second clinical study. Following treatment with three cycles of TPA in the second study, this patient and another (#2a), who had never been treated with TPA, experienced a disappearance of AIDS symptoms and both became sufficiently well to resume their normal activities. The other eight patients began the study without AIDS symptoms and were symptom free at the end of the study. All patients remain under observation. Treatment with anti-AIDS drugs continues uninterrupted.

As can be seen in Table 4, there was an increase in all patients in the CD 3, 4 and 8 levels with the most striking and consistent increases in CD3 levels. The viral load of HIV varied. It was undetectable in three patients (<200); it increased somewhat in six others and was reduced in one.

Example V

Third Clinical Study of HIV+Patients Treated with TPA

Six patients, two males and four females between the ages of 37 and 52 years of age (Patients #13-18), were treated with TPA. Four of these patients previously received TPA treatment in combination with anti-HIV drugs in the two previous clinical studies. The two remaining patients had never been treated with TPA, but had previously received anti-HIV drug regimens. All treatments were stopped three days prior to the initiation of the third clinical study and were not resumed until 60 days after completion of the TPA treatment. The resumption of the standard HIV treatments was required by local health authorities.

Each patient in the study received 150 g of TPA in 200 ml of sterile saline by intravenous infusion over a 1.5 to 2 hour period daily for 60 days for a total administered dose of 9.0 mg. Following completion of the 60 days of TPA therapy, these patients remained under observation for an additional 60 days though the received no further treatment.

CD3, CD4 and CD8 levels in peripheral blood were quantitated prior to starting treatment, and again at 30 and 60 days using flow cytometry and the appropriate antibodies obtained from B.D. Bioscience, San Diego, Calif. Viral load was determined using conventional methods at Kuang Ann men Hospital, Beijing, China. Patients RBC, WBC, platelets and hemoglobin levels were also measured.

As can be seen in Table 6, the viral load in the six patients was either low or undetectable at the beginning of the trial and remained low throughout the clinical trial period despite the discontinuation of traditional antiretroviral therapy. Additionally, there was no rebound in viral levels 6 to 15 days after stopping antiretroviral treatment as previously reported as occurring in patients with a plasma viral load below 50 HIV copies per ml. (Harrigan et al., AIDS 13, F59-F62 (1999)). The CD3, CD4 and CD8 levels were variable and inconclusive.

TABLE SIX

Study 3
CD4 CD8 CD3 AND HIV LOAD RESULTS OF 6 PATIENTS

| PATIENT NO. | *TEST TIME | CD3 | CD4 | CD8 | **HIV (copies/ml) |
|---|---|---|---|---|---|
| 13 | 1. | 3500 | 1135 | >2000 | undetectable |
|    | 2. | 2771 | 735  | 1938  | 0.533 |
|    | 3. | 2689 | 721  | 1897  | 0.133 |
| 14 | 1. | 1415 | 677  | 664   | 0.374 |
|    | 2. | 1522 | 613  | 796   | 0.353 |
|    | 3. | 902  | 369  | 485   | 0.038 |
| 15 | 1. | 759  | 9    | 542   | 0.533 |
|    | 2. | 1865 | 8    | 1408  | 1.99 |
|    | 3. | 2099 | 11   | 1507  | undetectable |
| 16 | 1. | 1368 | 128  | 1166  | undetectable |
|    | 2. | 1477 | 105  | 1318  | 1.28 |
|    | 3. | 1305 | 46   | 1220  | 0.012 |
| 17 | 1. | 428  | 95   | 297   | 0.002 |
|    | 2. | 594  | 112  | 424   | 0.152 |
|    | 3. | 317  | 31   | 246   | 0.056 |
| 18 | 1. | 1041 | 392  | 457   | undetectable |
|    | 2. | 703  | 229  | 343   | 0.174 |
|    | 3. | 579  | 165  | 290   | undetectable |

*Test time:
1. Before TPA
2. Thirty Days After TPA
3. Sixty Days After TPA
**All Figures in Millions White blood cells (WBC), red blood cells (RBC), hemoglobin (Rb) and platelets (PLt) were measured prior to starting TPA treatment, 15, 30, 45 and 60 days after starting TPA treatment and 30 days after stopping TPA treatment. As can be seen in Table 7, most values were within the normal range.

The patients involved in the third clinical study experienced no viral load rebound as typically seen when antiretroviral therapies are discontinued. They additionally had no recurrence of AIDS symptoms during the 120 day observation and treatment period, felt normal and were able to conduct their usual life activities.

TABLE SEVEN

Study 3
PERIPHERY BLOOD PROFILE OF 6 PATIENTS

| PATIENT NO. | *TEST TIME | WBC ($\times 10^9$/L) | RBC ($\times 10^{12}$/L) | Rb (g/L) | PLt ($\times 10^9$/L) |
|---|---|---|---|---|---|
| 13 | 1. | 9   | 3.75 | 139 | 246 |
|    | 2. | 9   | 3.88 | 140 | 240 |
|    | 3. | 8.9 | 4.35 | 148 | 275 |
|    | 4. | 3.6 | 3.9  | 125 | 304 |
|    | 5. | 8.8 | 4.55 | 126 | 221 |
|    | 6. | 7.5 | 4.55 | 130 | 272 |
| 14 | 1. | 4.2 | 4.16 | 111 | 188 |
|    | 2. | 4.1 | 4.03 | 114 | 169 |
|    | 3. | 5.9 | 4.48 | 116 | 232 |
|    | 4. | 3.9 | 4.44 | 109 | 152 |
|    | 5. | 4.4 | 4.31 | 96  | 227 |
|    | 6. | 6.5 | 4.4  | 104 | 193 |
| 15 | 1. | 5.9 | 3.67 | 110 | 397 |
|    | 2. | 5   | 3.41 | 101 | 219 |
|    | 3. | 5.2 | 4.83 | 113 | 247 |
|    | 4. | 6.2 | 4.13 | 110 | 262 |
|    | 5. | 6.2 | 4.04 | 99  | 239 |
|    | 6. | 8.4 | 3.9  | 110 | 278 |
| 16 | 1. | 6   | 3.62 | 144 | 297 |
|    | 2. | 8.1 | 3.65 | 142 | 415 |
|    | 3. | 4.3 | 4.03 | 145 | 345 |
|    | 4. | 4.6 | 3.86 | 124 | 291 |
|    | 5. | 5.1 | 4.1  | 123 | 276 |
|    | 6. | 3.8 | 4.71 | 144 | 224 |
| 17 | 1. | 5.5 | 3.06 | 124 | 242 |
|    | 2. | 6.4 | 2.98 | 118 | 151 |
|    | 3. | 4   | 3.2  | 121 | 177 |
|    | 4. | 3.9 | 3.49 | 116 | 131 |
|    | 5. | 7.7 | 3.34 | 99  | 121 |
|    | 6. | 4.8 | 3.42 | 100 | 178 |
| 18 | 1. | 7.4 | 3.91 | 156 | 240 |
|    | 2. | 8.1 | 3.69 | 141 | 208 |
|    | 3. | 4.5 | 4.32 | 154 | 228 |
|    | 4. | 4.9 | 4.14 | 131 | 149 |
|    | 5. | 3.5 | 4.56 | 136 | 222 |
|    | 6. | NA  | NA   | NA  | NA  |

*Test time:
1. Before TPA
2. Fifteen Days After TPA
3. Thirty Days After TPA
4. Forty Days After TPA
5. Sixty Days After TPA
6. Thirty Days After Stopping TPA Example VI Case Studies Results of treatment of initially symptomatic AIDS patients treated with TPA according to the protocols of Example III, IV, and V. Patients who participated in multiple studies are in some cases identified by more than one patient number. All patient identification numbers correspond to the patient numbers in Tables 1-7.

Patient #1 and 15: H.L.Y., female, 35, participated in all three clinical studies, diagnosed with AIDS and had clear symptoms of this disease in 2003. At the time the first study began, she had frequent fever, diarrhea, oral lesions, poor appetite, weight loss, left eye vision loss (syncytia formation) and coughing (tuberculosis). The patient started to receive antiviral medications Stavudine ($D_4T$), Lamivudine (3TC), Nevirapine (NVP) and Zidovudine (AZT) in 2004. Despite anti-AIDS drugs, she had a CD4 count of 3 and was unable to perform any physical work.

During the first study following the protocol of Example III, above, she experienced an increase in body temperature of 38-39° C. on four different occasions that lasted 2 to 4 hours. After treatment with TPA, there was a gradual improvement in symptoms. Her appetite improved and diarrhea, oral lesions, and fatigue disappeared but her eyesight remained impaired. She gained some weight and reported being able to resume housework. She continues to receive antiviral therapy. There appears to be no correlation in improvements in symptoms and changes in her CD 3, 4, 8 levels and viral count.

H. L. Y. participated in the second study described in Example IV, above. At the initiation of the second study she has no symptoms of AIDS. During this subsequent treatment with TPA she experienced no adverse effects. After both the first and third cycle of treatment with TPA, her CD3, CD4, and CD8 levels increased as did her white blood cell count. Her HIV count was somewhat higher, but she is able to function normally and continues to have no symptoms of AIDS.

H.L.Y. participated in the third study described in Example V, above. At the initiation of the third study, she was still having problems with her eye. During the third study, she experienced a fever of 38-38.5° C. during the third and fourth day of TPA infusion. No AIDS symptoms returned during either the study or the 60 day observation period. Except for her sight, she remains symptom free, feels normal and is able to conduct normal activities. She reinitiated antiviral therapy after completion of the 60 day observation period and remains under the care of a physician.

Patient #2: C.X., female, 49, participated in first clinical study, diagnosed with AIDS and had clear symptoms of this disease in 2004. She had mild oral lesions, fatigue, skin thrush, fever and poor appetite. Some of these symptoms were due to herpes virus.

She had been treated with AZT, DDI and NVP but drug treatment was terminated due to side effects. She received no drugs for 3 months prior to TPA treatment. She was hospitalized frequently and was unable to work. Her CD4 count prior to treatment was 26.

During TPA treatment according to the protocol of Example III, she experienced an increase in body temperature of 37.5 to 38 degrees centigrade on three different occasions that lasted 1-2 hours. After treatment with TPA, her oral lesions, skin thrush and fever disappeared. Her appetite improved sufficiently so that she gained weight and had sufficient energy to resume housework. She remained symptom free for five months and was not given any anti-AIDS drugs during this period. There appeared to be no correlation between the improvement in symptoms and her CD 3, 4, 8 levels and viral count.

Patient #2a M. S., male, 48, participated only in the second clinical study, had frequent fever, diarrhea, weight loss, a weak immune system, severe depression and was unable to work.

During treatment with TPA according to the protocols of Example IV, his body temperature increased to 38.5 to 39 degrees centigrade on five occasions for 2 to 4 hours.

After the third cycle of TPA treatment, the fever and diarrhea were no longer a problem. His CD3, CD4 and CD8 counts trended upwards as did the WBC and HIV count. His physical and mental condition returned to normal and he is able to work.

Patient #3: Y.P., male, 51, participated only in the first clinical study, diagnosed with AIDS and had clear symptoms of this disease in 2004. His major symptoms were diarrhea, fatigue, weight loss, anemia and purple marks on the skin of both legs; and he could only do light work. He was being treated with AZT, DDI and NVP but a serious anemia resulted in the termination of drug treatment four months prior to being given TPA. His initial CD4 count was 32.

During TPA treatment according to the protocol described in Example III, he experienced an increase in body temperature of 38 to 39° C. on three occasions that lasted 1 to 2 hours. After treatment with TPA, there was a marked improvement in his symptoms and he was able to return to work involving heavy labor and is leading a normal life. He was symptom free for five months after TPA therapy and was not treated with antiviral drugs during this period. There appeared to be no correlation between CD 3, 4, and 8 levels and improvement in symptoms but there was some increase in viral count.

Patient #4: L.W., male, 34, participated in only the first clinical study, tested positive for HIV and had clear symptoms of this disease in 2004. His major symptoms were diarrhea, fever, weight loss, cough (tuberculosis), right side neck lymph node enlargement and he was unable to work. His initial response to treatment was poor. The schedule of antiviral medication of 3TC, DDI and NVP was irregular and was stopped during TPA therapy. His initial CD4 count was 173.

During treatment with TPA according to the protocol of Example III, he experienced an increase in body temperature of 38 to 39° C. on five occasions that lasted 0.5 to 1 hours. After treatment, the occasional bout of diarrhea was treated successfully with and an anti-diarrhea drug. An improvement in appetite has resulted in an increase in weight and energy that resulted in his returning to a regular work schedule. The lymph node returned to normal size. He continues to be treated with anti-viral drugs. There appeared to be no correlation between the improvements in symptoms, CD3, 4, 8 levels and viral count.

Patient #5 and 3a: H.S., female, 37, participated in the first two clinical studies, tested positive for HIV and had clear symptoms of the disease in of 2004. At the time the first study began, her major symptoms were skin thrush, hair loss, mouth infection, weight loss and fatigue. She was being treated with $D_4T$, DDI, and NVP but treatment was stopped due to loss of kidney function. She had an initial CD4 count of 106 but could handle regular labor work.

During treatment with TPA according to the protocol of Example III, she experienced in increase in body temperature of 37.5 to 38° C. on five occasions that lasted 0.5 to 1.0 hours. After treatment with TPA, no improvement in symptoms occurred. Treatment with anti-viral drugs was resumed without return of the previous side effects and the intensity of her symptoms were reduced after one month. This treatment is being continued and she has returned to work. There appeared to be no correlation between the improvement in symptoms and changes in the CD 3, 4, and 8 levels or the HIV count.

At the time of the second study, she had no symptoms of AIDS and suffered no adverse effects to the course of treatment described in Example IV. After the second study, her CD3, CD4 and CD8 levels trended upwards as did her white blood count and platelet levels. Her HIV count was initially undetectable, but increased after the third cycle of treatment. She is currently able to work.

Patient #6, #4a, and #17: H.S.C., male, 36, participated in all three clinical studies, tested positive for HIV and had clear but mild symptoms in 2004. At the time the first study began, he suffered from dizziness, headache, poor appetite and an increased susceptibility to upper respiratory tract infections but was able to work regularly as a laborer. He was being treated with antiviral drugs AZT, DDI and NVP but terminated their use due to adverse reactions. His initial CD4 level was 232.

During treatment with TPA according to the protocol of Example III, he did not experience an increase in body temperature or any other side effect. After treatment, his symptoms remained unchanged and a reduction in platelets appeared unrelated to TPA treatment. He continued to be treated with antiviral drugs and is able to work as before. There appeared to be no correlation between the improvement in symptoms and the CD 3, 4, and 8 levels and viral load.

At the time of the second study, he had no symptoms and his immune system appeared to be functioning normally. During the second study according to Example IV, he again suffered no side effects from treatment with TPA. His CD3, CD4, and CD8 count increased somewhat as did his white blood cell count. The viral load was initially undetectable but increased after the third cycle of treatment. However, he does not have any symptoms of AIDS and has returned to work.

At the initiation of the third clinical study, he had no symptoms. During treatment with TPA according to the protocol of Example V, he experienced an incident of local irritation due to a leaking needle on day 32 but was treated successfully in three days. He remains symptom free, feels normal, and is able to do heavy labor. He started antiviral therapy after completion of the 60 day observation periods and remains under the care of a physician.

Patient #7, #5a and #16: H. C. L., male, 49, participated in all three clinical studies, tested positive for HIV and had clear symptoms of the disease in 2004. His major symptoms at the time of the first study were weight loss, skin thrush, fatigue, poor appetite and coughing (tuberculosis) but he was able to do light work. He was treated simultaneously with $D_4T$, DDI, NVP and antituberculosis medication. His initial CD4 count was 10.

During treatment with TPA according to the protocol outlined in Example III, he experienced an increase in body temperature to 38° C. on two occasions accompanied by mild dizziness and headache. After treatment, his symptoms remained unchanged and antiviral therapy was resumed one month later. With time, his cough, appetite and energy level improved and he is able to work. He continued both antiviral and anti-tuberculosis medication. There appeared to be no correlation between improvements in symptoms and his CD3, 4, and 8 levels or viral load.

At the time of the second clinical investigation, he had no symptoms of AIDS and his immune system appeared to be functioning normally. He suffered no adverse effects from treatment TPA during the second clinical investigation. After treatment, his CD4 level was unchanged, but his CD3 and CD8 levels trended upwards as did his white blood cell count. His viral load was undetectable. He has not had any symptoms of AIDS and has returned to work.

At the start of the third clinical investigation, he was not experiencing AIDS symptoms. During treatment according to the protocol outlined in Example V, he suffered from a fever on one occasion. He remains symptom free, feels normal, and is able to do heavy labor. He re-started antiviral drugs after completion of the 60 day observation period and remains under the care of a physician.

Patient #8, #6a, and 18: Y.X.O., female, 36, participated in all three clinical studies, tested positive for HIV in 2004. Her major symptom at the time of the first study was an increased susceptibility to upper respiratory tract infection. She was treated with AZT, DDI and NVP. At the start of the study, her CD4 level was 524 and she could handle regular labor work.

During treatment with TPA according to the protocol of Example III, she experienced an increase in body temperature to 38.5° C. on one occasion that lasted four hours. After treatment, the frequency of her colds decreased and she had no other symptoms. She continued to be treated with antiviral drugs and is able to work. There appeared to be no correlation between the improvement in symptoms and her CD 3, 4, or 8 levels or viral load.

At the time of the second clinical investigation, she had no symptoms of AIDS and her immune system appeared to be functioning normally. During the second study, according to the protocols of Example IV, her body temperature again rose to 38.5 degrees centigrade for two hours on a single occasion. After treatment, her CD3 and CD8 levels increased somewhat while her CD4 and white blood cell count remained unchanged. Her viral load is undetectable. She appears normal and is able to work at physically demanding tasks.

At the time of the third clinical investigation she was symptom free. The only side effects from treatment according to the protocol of Example V was as fever of 38-39° C. on the second day of the treatment that lasted for two hours and skin irritation from a leaking needle on day 36 that cleared in two days. She remains symptom free, feels normal and is able to do heavy labor. She re-started antiviral therapy after completion of the 60 day observation period and remains under the care of a physician.

Patient #9 and #7a: C.T.F., male, 44, participated in the first two clinical studies, tested positive for HIV and had clear symptoms of the disease in 2004. His symptoms at the initiation of the first study included persistent diarrhea, dizziness, headaches, poor appetite, weight loss and fatigue. He had a positive response to AZT, DDI and NVP treatment and blood HIV count was near the lowest limit. Despite the positive response, his symptoms persisted and he checked into the hospital due to diarrhea that persisted for 20 days. He was very depressed and unable to do any work.

During treatment with TPA according to the protocol of Example III, he experienced an increase in body temperature of 37.5 to 38° C. on six occasions that lasted 2 to 4 hours. A leaking needle caused a serious skin irritation during one administration of TPA but was treated successfully. After eight treatments with TPA, the mild dizziness and headache persisted but the incidence of diarrhea began to decrease and his appetite improved. A week later, his diarrhea was completely gone and he had a normal appetite. He was able to return to work and is receiving antiviral drug therapy. There appeared to be an upward trend of CD3, 4, 8 levels and the HIV count was undetectable.

At the time of the second clinical investigation, he had no symptoms of AIDS and his immune system appeared to be functioning normally. During TPA treatment according to the protocol of Example IV, he suffered no adverse effects. After treatment, his CD3, CD4 and CD8 levels increased somewhat while his white blood cell count remained unchanged. His HIV count continues to be undetectable. He is able to do strenuous work.

Patient #10 and #8a: W.F.W., Female, 47, participated in the first two studies, tested positive for HIV and had clear symptoms of the disease in 2003. Her symptoms at the initiation of the first study included low body temperature, diarrhea, low platelet count, coughing blood, bloody bowel movements, dizziness, headache, poor appetite, weight loss, fatigue with mild skin thrush and deep depression. She was hospitalized on one occasion for two months because of bloody bowel movements. She was very depressed and unable to work. She did not respond positively to the AZT, DDI and NVP treatment and her symptoms were not under control.

During her first treatment with TPA according to the protocol of Example III, she experienced an increase in body temperature to 38.5° C. on one occasion that lasted 4 hours. After TPA treatment, her dizziness, headache and diarrhea gradually lessened. Eventually, her appetite led to a weight gain and an improvement in her energy level. Her platelet count rose from 30,000 to 110,000 per microliter and the skin thrush and diarrhea were eliminated. She was able to work again and was treated with antiviral drugs. She had fever and diarrhea occasionally that she was able to control with drugs.

Six months later she suffered from mild headaches and dizziness and underwent a second treatment with TPA.

During her second treatment with TPA, she experienced an increase in body temperature to 37.5 to 38° C. on five occasions that lasted 2 to 4 hours. Twenty hours after the 13$^{th}$ injection of TPA, her temperature reached 40.5 degrees centigrade and lasted for several hours. It was concluded that the increase in temperature was not related to TPA therapy.

After her second treatment with TPA, her symptoms disappeared, her appetite improved and she gained weight, which enabled her to regain her energy, return to work and lead a normal life. She was free of symptoms for one year and has had few colds in the first six months after the second TPA treatment. There appears to be an upward trend for the CD 3, 4, and 8 levels and the HIV counts.

At the time of the second clinical trial according to the protocol of Example IV, this patient continued to display no symptoms of AIDS and her immune system appeared to be functioning normally. She suffered no adverse effects during treatment. After treatment, her CD3, CD4 and CD8 counts increased somewhat as did her WBC. Her HIV count increased somewhat. Since the studies, she has been healthy and engaged in laborious work.

Patient #11 and 9a: C.T.L., female, 40, participated in the first two studies, was diagnosed with AIDS and had clear symptoms of this disease in 2003. At the initiation of the first study she had persistent diarrhea, low body temperature, oral lesions, severe skin thrush, itching, purple blotches on her face and lips, dizziness, headache, poor appetite, and fatigue and depression. She responded poorly to AZT, 3TC and NVP treatment. Her symptoms were not under control and she was unable to work. Her initial CD4 count was 40.

During her first treatment with TPA, she experienced an increase in body temperature to 38 to 39° C. on four occasions that lasted 2 to 4 hours. She had shortness of breath on two occasions that lasted 20 to 30 minutes each.

After the sixth dose of TPA, her skin thrush began to disappear and upon completion of TPA treatment, the dizziness, headache, fever and skin thrush were improving and gradually faded away. Her appetite, physical condition and depression improved sufficiently for her to return to work.

This patient had a second treatment with TPA 18 months later due to the return of symptoms including mild skin thrush, diarrhea and dizziness. During this second treatment, she experienced an increase in body temperature to 37.5 to 38° C. three times that lasted 2 to 4 hours. There were no other adverse reactions. After treatment with TPA, her symptoms disappeared completely and her physical condition improved sufficiently to allow her to return to work. She has been without symptoms for one year and she has rarely had a cold. There appears to be an upward trend in CD 3, 4, and 8 levels, but her HIV counts did not change.

At the time of the second clinical study according to the protocol of Example IV, this patient exhibited symptoms of AIDS including headache, dizziness, poor appetite and a weak immune function. She suffered no adverse effects during treatment. After treatment, her CD3 and CD8 levels increased while her CD4 count was unchanged. Her HIV count increased slightly but no other changes were observed. Her mental and physical condition has improved considerably and she is doing strenuous physical work.

Patient #12 and #10a: C.C.L., female, 39, participated in the first two studies, diagnosed with AIDS and had clear symptoms of this disease in 2003. At the initiation of the first study she had persistent low body temperature, skin thrush, dizziness, headache, poor appetite, oral lesions, fatigue and deep depression. She was treated with AZT, 3TC and NVP but had poor results and she was unable to work. Her initial CD4 count was 84.

This patient was treated with TPA twice during the period March 2005 to March 2006. During the first treatment with TPA, she experienced an increase in body temperature to 38 to 38.5° C. on eight occasions that lasted 2 to 4 hours. She experienced shortness of breath on one occasion for 15 minutes and suffered a skin irritation due to a leaking needle.

After the seventh injection, her oral lesions disappeared. Upon completion of all the injections, all symptoms disappeared and her physical condition improved sufficiently for her to return to work.

Six months later, this patient was re-retreated with TPA due to the return of light diarrhea and dizziness. She experienced an increase in body temperature to 37.5 to 38° C. centigrade on six occasions associated with TPA administration that lasted 2 to 6 hours. Starting with the eighth injection, the dose was increased from approximately 150 μg to 250 μg TPA. No adverse effects occurred. Upon completion of TPA therapy, all her symptoms disappeared. Her physical condition was restored to normal and she returned to work and has had a normal life. She has been symptom free for one year and has rarely had a cold. There were no changes in CD 3, 4, or 8 levels, but her HIV count increased.

At the time of the second clinical study, this patient had no symptoms of AIDS though she did have a weakened immune system. She was treated according to the protocol of Example IV and suffered no adverse effects. After treatment, there were slight increases in her CD3, CD4 and CD8, and modest increases in WBC, RBC and HGB while platelets appeared to decrease. The HIV count was reduced somewhat. She has been healthy and engaged in strenuous physical work since her treatments.

Patient #13: L.F.L., female, 53, diagnosed with AIDS in 2004, participated in only the third clinical study. She presented with mild symptoms of poor appetite and weight loss. Long term antiviral drugs were effective and caused her virus count to decrease below detectable levels and CD3, CD4 and CD8 counts to increase to a high level. She had no symptoms prior to TPA treatment and had no side effects from its administration. She remains symptom free, feels normal, and is able to conduct normal activities. She re-started antiviral drug therapy after completion of the 60 day observation period.

Patent #14: K.S.M., female, 45, diagnosed with AIDS in 2004, participated in only the third clinical study. Her symptoms were mild and consisted of poor appetite and frequent colds. She had been treated with antiviral drugs, but stopped due to severe liver toxicity. She had no symptoms prior TPA treatment and the only TPA side effect was irritation due to a leaking needle on day 43 that was easily treated. No AIDS symptoms occurred during the entire treatment and observation period. She feels normal and is able to conduct her usual activities. After completion of the 60 day observation period she was lost to the study and did not renew antiviral therapy.

Example VII

Treatment of Relapsed/Refractory Malignancies with TPA

Patients with histologically documented relapsed/refractory hematologic malignancy/bone marrow disorders are treated with a combination of TPA (Xichuan Pharmaceuticals, Nan Yang, Henan, China), dexamethasone and choline magnesium trisalicylate. Comparable methods as set forth below for demonstrating the therapeutic use of TPA in the treatment of Acute Myelogenous Leukemia (AML) will be applied to demonstrate the use of TPA for treating other neoplastic conditions and malignancies. Other neoplastic conditions and malignant disorders amenable to treatment using the methods and compositions of the invention include various forms of cancer, including blood and bone malignancies and solid tumors of various types. In addition to the specific protocols herein, successful treatment and/or remission will be determined for different targeted neoplastic and malignant conditions using any of a wide variety of well known cancer detection and assessment methods—for example by determining size reduction of solid tumors, histopathological studies to evaluate tumor growth, stage, metastatic potential, presence/expression levels of histological cancer markers, etc.

AML is an aggressive disease that generally warrants urgent and intensive therapy. The average patient age at AML diagnosis is 64-68 years old, and patients over the age of 60 treated with standard chemotherapy are cured of their disease <20% of the time. Patients who develop AML after an antecedent hematologic disorder or prior leukemogenic chemotherapy/radiation therapy have similarly poor outcomes, as do patients whose disease is associated with specific adverse cytogenetic and clinical features. Hence, most patients diagnosed with AML have patient and/or disease-related features that are associated with a very poor prognosis. For patients with relapsed disease, no standard non-transplant therapy has demonstrated the capacity for cure. For these patients, AML is often a fatal disease. New approaches to the therapy of AML are needed.

Employing the methods and compositions of the instant invention, TPA, is developed as a therapeutic agent for treating patients with AML, based on TPA's novel role in modulating intracellular signaling pathways, it's capacity to induce differentiation and/or apoptosis in cell lines, and clinical data indicating the effectiveness of TPA in treating neoplastic and malignant disorders, including myeloid malignancies.

Thus far clinical evaluation of TPA has demonstrated that TPA exerts direct therapeutic cytotoxic effects in at least a subset of AML cases, as measured by cell viability and apoptosis assays. In all primary cultures analyzed by Western analysis, TPA strongly induced ERK phosphorylation by 1 hour in culture. TPA's cytotoxic effect on primary AML cells is associated with the subsequent loss of the phospho-ERK pro-survival signal after 24 hour ex vivo exposure. This observation is in good agreement with other studies that reported decreased primary AML survival after pharmacological interruption of ERK signaling by MEK inhibitors, such as PD98059, U0126 and PD 184352. In our studies, loss of ERK signaling was associated with induction of ERK phosphatases.

In addition to protein kinase C and ERK activation, TPA is a known inducer of NF-κB, a pro-survival transcription factor often constitutively active in AML blasts and leukemic stem cells. Recent work from our laboratory has demonstrated that AML cell NF-κB can be inhibited in vivo with 48 h of treatment with dexamethasone+choline magnesium trisalicylate (CMT). In addition, we have shown that dexamethasone can induce MKP-1 ERK phosphatase expression and enhance TPA cytotoxicity on primary AML samples. In this context, we have chosen in exemplary embodiments below to use dexamethasone and CMT as adjunctive medications to be used 24 h pre- and 24 h post treatment with TPA. These medications are well-tolerated and anticipated to reduce inflammatory adverse effects of treatment and enhance TPA cytotoxicity by increasing ERK phosphatase expression and inhibiting NF-κB. In addition dexamethasone and CMT will be used as adjunctive medications because they are anti-inflammatory, may ameliorate adverse effects, and may enhance anti-leukemic activity by inhibition of the anti-apoptotic effects of constitutive NF-κB expression and induction of phosphatases that decrease signaling pathway activity.

An initial TPA Phase 1 study enrolled 35 patients [23 with relapsed/refractory AML, 2 with other myeloid malignancies (CML-blast crisis, myelodysplasia with excess blasts), 3 with Hodgkin's Disease, 3 with non-Hodgkin's lymphoma and 4 with solid tumors]. The majority of patients had relapsed/refractory AML. Our clinical results include one AML patient with stable disease for >5 months, who received 8 TPA infusions. In a second AML patient, a pronounced (5-fold) decline in the number of circulating blasts was seen following TPA administration. This decline in leukemic blasts persisted for 4 weeks, and the patient eventually died from a fungal infection. Finally, a patient with relapsed and refractory Hodgkin's disease despite high dose chemotherapy with autologous stem cell rescue had a partial remission of a chest wall mass after TPA administration. TPA dose escalation has been completed, in the last cohort 2 out of 3 patients treated at a dose of 0.188 mg/m2 dl-5, 8-12 experienced grade III non-hematologic dose limiting toxicities (DLT), establishing the maximum tolerated TPA dose as a single agent at 0.125 mg/m2/d on dl-5 and 8-12.

In the case of AML and other hematologic malignancies, patients are given an initial dose of TPA of 1 mg/week×3 weeks (days 1, 8, 15) administered with continuous/intermittent pulse oximetry for 6 hours. Twenty four hours prior to initiation of TPA therapy, patients are given 10 mg of dexamethasone every six hours and 1500 mg of choline magnesium trisalicylate (CMT) every eight hours continuing until 24 hours after administration of TPA. After administration of the initial dose of TPA, patients have a two week rest period after which they may be reevaluated. Those patients that have a disease response or stabilization from the initial dose of TPA are treated for up to six cycles of twenty-eight days according to the protocol below.

Following the two week rest period, patients are pre-medicated with Tylenol 650 mg and Benadryl 25-50 mg (depending on the patient's size and age) thirty minutes prior to administration of TPA. They are then given an intravenous infusion of TPA through a central venous catheter daily for 5 days a week for two consecutive weeks followed by a 2-week rest period. TPA is administered at a dose of 1 mg in 200 ml of normal saline over 1 hour. Twenty four hours prior to initiation of TPA therapy, patients are given 10 mg of dexamethasone every six hours and 1500 mg of choline magnesium trisalicylate continuing every eight hours until 24 hours after administration of the TPA.

Blood levels of TPA are measured prior to and after infusion using a bioassay that measures organic solvent extractable differentiation activity. 1 ml of blood is extracted twice with 5 ml of ethyl acetate, redissolving the extraction residue in 50 μL of ethanol and addition of an aliquot of HL60 cells. After 48 hours, adherent cells are measured.

Tests are also run on blood samples taken prior to and after infusion with TPA to determine levels of white blood cells, platelets, and neutrophils. The samples are additionally analyzed for the presence of myeloblasts and Auer rods. These and continuing experiments will further elucidate the therapeutic cytotoxic and other effects that TPA elicits against neoplastic cells in AML and other neoplastic and malignant conditions.

Example VIII

Measurement of the Modulation of ERK Activation

Phospho-ERK levels are measured in circulating malignant cells in patients with leukemia and in peripheral blood mononuclear cells in lymphoma/solid tumor patients. A blood sample is taken from patients treated according to the protocol of Example VII both prior to and after administration of TPA.

In leukemia patients with a WBC>1000 per μL, flow cytometry is performed on a blood sample using cell surface antigen-specific and phospho-ERK specific antibodies directly conjugated to flurophores (BD Biosciences, San Jose, Calif.). Samples are taken pre-administration of TPA and one hour after infusion of TPA on days 1, 2, and 11 in the initial treatment according to the protocol of Example VII and days 1 and 11 in subsequent cycles. In leukemia patients with an absolute leukemic blast number >2500 per μL and other non-leukemic patients, peripheral blood samples are taken on days 1, 8 and 15 of the initial cycle according to the protocol of Example VII prior to and 1 and 4 hours post infusion. Samples are also analyzed using Western blot analysis for phosphor-ERK, and total ERK1/2 levels to confirm the results obtained from the flow cytometry and correlated to clinical responses.

The foregoing analyses will further elucidate TPA's role in treatment of neoplastic and malignant conditions, including TPA's cytotoxic effect on malignant cells, exemplified by primary AML cells, and the associated reduction by TPA of the phosphor-ERK pro-survival signal.

Example IX

Measurement of NF-κB Modulation

In prior studies we have shown that NF-κB activity can be modulated in patients following administration of TPA with dexamethasone. Additionally, dexamethasone has been shown to induce MKP-1 ERK phosphatase expression and enhance TPA cytotoxicity. The following studies are designed to further elucidate how NF-κB activity is therapeutically modulated in patients treated with TPA plus dexamethasone.

NF-κB binding is measured in patient peripheral blood samples at baseline and pre and post infusion from patients treated with TPA according to Example VII using ELISA-based assays (BD Bioscience, San Jose, USA). NF-κB levels are quantified using chemiluminescent intensity to detect binging in limiting amounts of cellular extract using a 96-well format. Additionally, electrophoretic mobility shift assays are performed to measure NF-κB binding in peripheral blood samples from leukemia patient with an absolute leukemic blast number ≥2500 per μL and other non-leukemic patients with normal white blood cell counts.

The foregoing studies will further PA is an inducer of NF-κB, however these experiments demonstrate that AML cell NF-κB can be inhibited with treatment with dexamethasone and choline magnesium trisalicylate.

Example X

Determination of Changes in Leukemic Gene Expression

TPA induces RNA levels of several dual specificity phosphatases capable of terminating pro-survival ERK pathway signaling. A blood sample taken pre and post infusion from patients with AML treated with TPA according to Example VII is used to study RNA expression of AML signaling components such as the MAPK-specific DUSPs using quantitative realtime RT-PCR and oligonucleotide microarray analysis.

Although the foregoing invention has been described in detail by way of example for purposes of clarity of understanding, it will be apparent to the artisan that certain changes and modifications may be practiced within the scope of the appended claims which are presented by way of illustration not limitation. In this context, various publications and other references have been cited with the foregoing disclosure for economy of description. Each of these references is incorporated herein by reference in its entirety for all purposes. It is noted, however, that the various publications discussed herein are incorporated solely for their disclosure prior to the filing date of the present application, and the inventors reserve the right to antedate such disclosure by virtue of prior invention.

Example XI

Treatment of Lymphoma

Patient M.J., age 60, male, was diagnosed with a re-occurrence of lymphoma and a mass of 3.5 cm in diameter. The patient was given 15 injections of 0.19 mg of TPA (0.125 mg/m$^2$) every other day for 30 days and the mass disappeared. As of 2011, he has been in remission for three years.

Example XII

Treatment of Breast Cancer

Patient M.L., female, age 50, was diagnosed with terminal breast cancer. She was unresponsive to either radiation or chemotherapy and the cancer had metastasized into the bone leaving her wheelchair bound. She received 35 injections of TPA with a progressing dose from 0.18 mg of TPA (1×0.125 mg/m$^2$) to 0.26 mg of TPA (1.5×0.125 mg/m$^2$), three to four times, a week and is now in remission and able to walk normally.

Example XIII

Treatment of Lung Cancer

Patient J.L., male, age 56, was diagnosed with terminal lung cancer which was refractory to chemotherapy. The cancer metastasized into his bones leaving him unable to walk. After 35 injections of TPA with a progressing dose from 0.19 mg of TPA (1×0.125 mg/m$^2$) to 0.26 mg of TPA (1.5×0.125 mg/m$^2$) three to four times a week, he is in remission and able to walk normally.

Example XIV

Treatment of Liver Cancer

Patient X, male, age ? was diagnosed with metastatic liver cancer. His initial alpha fetoprotein level was 48,813. He was given chemotherapy and radiation treatments but his alpha fetoprotein level remained elevated at 50,000+. He then received three injections of 0.19 mg of TPA (0.125 mg/m²) and his alpha fetoprotein levels began dropping and returned to normal levels within four months Example XV TPA as an Adjuvant to Traditional Neoplasm Treatments Patient N.K., female, 54, was diagnosed with terminal metastasized pancreatic cancer. She received five injections of 0.18 mg TPA (0.125 mg/m²) per week for 12 weeks in addition to chemotherapy. Her treatment reduced the tumor in the pancreas from 6.3 cm to 2.4 cm. The patient maintained her appetite, did not lose her hair and had significantly less vomiting and nausea than in prior chemotherapy treatments without TPA.

Patient P.T., male, 42, was diagnosed with non-small-cell lung cancer. The cancer had metastasized and was refractory to Tarceva® (erlotinib) and Iressa™ (gefitinib). The patient was treated with a combination of gemcitabine and cisplatin according to standard protocols accompanied by an injection of 0.19 mg of TPA (0.125 mg/m²) each weekday for eight weeks. During the combined chemotherapy and TPA treatment he did not lose any hair and had significantly less nausea than experienced during prior chemotherapy treatments. He has been in remission since Jun. 30, 2010.

Patient B.L., male, age 59, was diagnosed with terminal nasopharyngeal carcinoma and treated with both chemotherapy and radiotherapy. He received injections of 0.19 mg of TPA (0.125 mg/m²) of TPA a day for five days prior to beginning radiotherapy and then 0.19 mg of TPA (0.125 mg/m²) every other day for a total of 20 injections. He has been in remission for two and a half years and did not suffer any apparent skin damage from the radiation treatment.

Example XVI

Chemoprotective Effect of TPA

A colony formation assay including semi-solid medium formulated with DMEM and 0.5% agar is used. For these cultures, mononuclear cells are plated at a concentration of about $2.5 \times 10^5$ cells/mL and GM-CSF and G-CSF are added at a concentration of about 100 U/mL. Cells are cultured for 14 days in a 5% $CO_2$ incubator, with 100% humidity at 37° C. At the end of the culture period, colonies of 50 or more cells are counted using an inverted microscope by two independent viewers. (Hamburger, 1977)

Peripheral stem cells are randomized into 4 groups at a concentration of $5 \times 10^5$ cells/mL in DMEM supplemented with 10% fetal calf serum. Groups 1 and 4 are untreated control and groups 2 and 3 are incubated for 24 hours with 0.05 µg/mL of TPA. After 24 hours, cells are washed with DMEM 10% fetal calf serum. Groups 3 and 4 are then incubated with 25 µg/mL of 5-fluorodeoxyuridine monophosphate, the metabolite of fluorouracil, for 20 hours. Subsequently, all groups are washed twice and the cells are plated in semi-solid agar medium. The colonies are counted at 14 days.

Example XVII

Use of TPA to Protect Against Radiation Damage

Three cell lines are used to determine the effectiveness of TPA against radiation damage: interleukin-3 dependent murine hematopoietic progenitor cell line, human bone marrow stromal cell line KM101, and bronchial epithelial (IB3) cells. 32D cl 3 interleukin-3 (IL-3) dependent murine hematopoietic progenitor cell line is derived from a long-term bone marrow culture of a C3H/HeJ mouse as described in Epperly, 2008. Cells are passaged in 15% WEHI-3 cell conditioned medium (as a source of IL-3), 10% fetal bovine serum (FBS) (Hyclone Laboratories, Logan, Utah), and McCoy's supplemented medium. The human bone marrow stromal cell line KM101 cells are passaged weekly in 24 cm Falcon plastic flasks in McCoy's 5A modified medium (GIBCO BRL, Gaithersburg, Md.) supplemented with 10% FBS (Hyclone Laboratories, Logan. Utah). IB3 cells are passaged twice weekly in standard Dulbecco's modified Eagle's medium (DMEM) (Lonza, Allendale, N.J.), supplemented with 10% FBS (Hyclone laboratories. Logan, Utah), 1% L-glutamine (GIBCO BRL, Gaithersburg, Md.) and 1% penicillin-streptomycin (GIBCO BRL, Gaithersburg, Md.) on uncoated 75 cm³ tissue culture Falcon flasks in a 5% $CO_2$ incubator at 37° C. for 48-72 hours to reach 80% confluency as described in Rwigema, 2011.

Cells from each cell line are suspended at $1 \times 10^5$ cells/mL and irradiated with 0 to 8 Gy. TPA is added to the irradiated cells 10 minutes after irradiation. The cells are then plated in quadruplet and incubated in a high-humidity incubator at 37° C. with 95% air/5% CO2 for 7 days, at which time the cells are stained using crystal violet and colonies of greater than 50 cells are counted. Each experiment is carried out 3 separate times on three separate days. Data are analyzed using linear quadratic and single-hit, multi-target models (See Epperley, 2001). The dose reduction factor (DRF) for TPA is calculated as the ratio of the dose giving 50% cell survival in the treated group divided by the dose at 50% survival in the control cell group.

Example XVIII

Protective Effect of TPA Against Damage from Radiation in Mice

Adult female C57BL/6 NHsd mice (20 to 22 g, Harlan Sprague Dawley, Chicago, Ill.) (n=15 per group) are irradiated with 9.5 Gy TBI to achieve the (LD 50/30) dose using a Gamma beta irradiation dose rate (74 cGy/min) and receive an intraperitoneal injection 10 minutes later of 0.125 mg/m² of TPA. The mice are monitored for survival (Rigwema, 2011).

Example XIX

Treatment of Individuals Who have Suffered a Stroke

Patient N.C., male, 68, suffered a stroke eighteen months prior to treatment with TPA. At the time TPA treatment was initiated, he was unable to walk without a cane, had difficulty with both his left hand and left leg and was tired and weak. He received injections of 1 ampoule containing 0.19 mg of TPA (0.125 mg/m²) every other day for four weeks, then 0.24 mg of TPA (1.25×0.125 mg/m²) every other day for 2 weeks, and then 0.26 mg of TPA (1.5×0.125 mg/m²) every other day for an additional 3 weeks. The patient has recovered fully.

Patient M.C., male, age 65, suffered a stroke seven years prior to beginning treatment with TPA. He received 3-4 injections of 0.19 mg of TPA (0.125 mg/m²) per week for ten weeks for a total of 35 injections. He has regained mobility in his face and had an 80% improvement in the mobility of his right side.

Example XX

Treatment of Embolic Stroke Model with TPA

Male Sprague-Dawley rats (Charles River Japan) each having a body weight of 280-350 g are used. An embolic stroke is induced following a modification of the method of Kudo, et al. (1982) The rats used for the collection of blood are anesthetized with 1.0% halothane (Fluorothane™; Takeda, Osaka, Japan) under spontaneous respiration. A 24-gauge Surflo™ (Terumo Medical Products, Elkton, Md.) is secured in the femoral artery and 0.1 mL of arterial blood is taken with a 1-mL syringe for injection (Terumo Medical Products, Elkton, Md.). The artery blood in the syringe is incubated at 30° C. for 2 days to form a blood clot. After that, 0.1 mL of physiological saline is added to the syringe for injection and passed through a 26-gauge injection needle (Terumo Medical Products, Elkton, Md.) twice so that the blood clot is crushed.

Rats in which a cerebral embolic stroke is induced are anesthetized with 1.0% halothane under spontaneous respiration. The neck of the rats is subjected to a midline incision and external carotid artery, superior thyroid artery, occipital artery and pterygopalatine artery are cauterized with a bipolar coagulator (T-45; Keisei Medical Industrial Co. Ltd, Tokyo, Japan). Cerebral embolism is induced by injecting 0.1 mL of the crushed blood clot into the internal carotid.

Evaluation of the formation of a cerebral embolism is carried out using a laser Doppler flowmetry (FloC1; Omegawave, Tokyo, Japan). A decrease in cerebral blood flow to a level of 30% or less is taken as a positive evidence of embolism formation. The cerebral blood flow is monitored for 30 minutes after infusion of the blood clot and blood flow is monitored as remaining at 50% or less of the flow prior to the injection of the blood clot. After that, a cannula (PE50) for administration of the medicament is secured in the jugular vein and the animals are woken.

The rats that have successfully formed a cerebral embolism are divided into four groups. The first group of rats is given a saline injection every other day. Groups 2-4 are given 0.125 mg/m$^2$ injection every other day for four weeks. Group 2 is then sacrificed. Groups 3-4 are given a further 0.156 mg/m$^2$ every other day for two weeks and then Group 3 is sacrificed. Group 4 is given 0.18775 mg/m$^2$ every other day for three weeks and then sacrificed.

The brains are excised after the animals are sacrificed and sliced in ten sections at 1 mm intervals using a McIwain tissue chopper (Mickle Laboratory Engineering, U.K.) and are stained by dipping for 20 minutes in a 2% TTC (2,3,5-triphenyltetrazolium chloride; Tokyo Kasei) at 37° C. Images of the TTC-stained slices are uploaded into a computer using a digital camera (HC-2500; Fuji PhotoFilm) and Phatograb-2500 (Fuji Photo Film) and infarct volume is calculated using Mac Scope (Mitani, Japan). Infarct volume is given by a mean value±standard error. With regard to the statistical test of the result of the infarct volume, the evaluation is done by carrying out a Dunnett's test for control group and for each of the TPA-administered groups as compared with the control group and then by carrying out the t-test for the TPA-administered group.

Neurological symptoms are observed daily until sacrifice and the rats are evaluated according to three tests: (1) Rats are held gently by the tail, suspended one meter above the floor, and observed for forelimb flexion; (2) Rats are placed on a large sheet of soft, plastic coated paper that could be gripped firmly by their claws. With the tail held by hand, gentle lateral pressure is applied behind the rat's shoulder until the forelimbs slid several inches; (3) Rats are allowed to move about freely and are observed for circling behavior. Scoring of the neurological symptoms is carried out according to the scale developed by Bederson et al. (1986) as follows: 0: no observable deficit; 1: forelimb flexion; 2: decreased resistance to lateral push without circling; 3: same behavior as grade 2, with circling.

Neurological symptoms are evaluated using a Steel's test for the control group and for each of the TPA administered groups as compared with the control group and then by carrying out a Wilcoxon test for the TPA administered group. In any of the tests, the value where p<0.05 is defined to be statistically significant.

Example XXI

Effectiveness of TPA in the Treatment of Stroke Using a Permanent Middle Cerebral Artery Occlusion Model Male Wistar rats (250-320 g) are used for this study. Animals are anesthetized with Isoflurane (3% induction, 1-2% maintenance). Anesthesia is monitored by toe pinch. Aseptic technique is used for all procedures during this study. The surgical site is clipped and cleaned with alcohol and surgical scrub. The animal is placed on a warm water heating pad to maintain body temperature. A paramedian incision is made on the neck over the carotid artery. The tissue is bluntly dissected away to reveal the carotid artery and the bifurcation. Sutures are placed around the proximal portion or the common carotid and the external carotid arteries. These sutures are tied off. An incision is made in the common carotid, distal to the ligation. A pre-prepared filament (4-0 monofilament suture or like material) is placed in the carotid and advanced into the internal carotid artery. The filament is advanced about 20 mm past the carotid bifurcation until slight resistance is felt as it wedges in the middle cerebral artery. Care must be taken to not rupture the artery upon insertion of the filament. The filament is tied in place and the skin incision closed. The animal is evaluated when awake for successful occlusion using the Bederson scale as previously described. (See Bederson et al., (1986) Stroke, 17:1304-1308.) Body temperature is taken every 15 minutes to maintain normothermia. Animals that have undergone the middle cerebral artery occlusion procedure may have difficulty in thermoregulation for a few hours after surgery Animals are placed in a cooling or heating box as determined by their temperature. Body temperature is maintained at 37.5° C. Animals are monitored for 6 hours following middle cerebral artery and are then placed in cages overnight.

The rats are divided into four groups. The first group of rats is given saline injections every other day. Groups 2-4 are given 0.125 mg/m$^2$ injection every other day for four weeks. Group 2 is then sacrificed. Groups 3-4 are given a further 0.156 mg/m$^2$ every other day for two weeks and then Group 3 is sacrificed. Group 4 is given 0.18775 mg/m$^2$ every other day for three weeks and then sacrificed.

The brains are excised after the animals are sacrificed and sliced in ten sections at 1 mm intervals using a McIwain tissue chopper (Mickle Laboratory Engineering, U.K.) and are stained by dipping for 20 minutes in a 2% TTC (2,3,5-triphenyltetrazolium chloride; Tokyo Kasei) at 37° C.

Images of the TTC-stained slices are uploaded into a computer using a digital camera (HC-2500; Fuji PhotoFilm) and Phatograb-2500 (Fuji Photo Film). Brain slices are photographed and analyzed for infarct size, infarct volume, penumbra, and edema.

Neurological symptoms are observed daily until sacrifice. Neurological symptoms are observed daily until sacrifice and the rats are evaluated according to three tests. (1) Rats are held gently by the tail, suspended one meter above the floor, and observed for forelimb flexion. (2) Rats are placed on a large sheet of soft, plastic coated paper that could be gripped firmly by their claws. With the tail held by hand, gentle lateral pressure is applied behind the rat's shoulder until the forelimbs slid several inches. (3) Rats are allowed to move about freely and are observed for circling behavior. Scoring of the neurological symptoms is carried out according to the scale developed by Bederson et al. (1986) as follows: 0: no observable deficit; 1: forelimb flexion; 2: decreased resistance to lateral push without circling; 3: same behavior as grade 2, with circling.

Neurological symptoms are evaluated using a Steel's test for the control group and for each of the TPA administered groups as compared with the control group and then by carrying out a Wilcoxon test for the TPA administered group. In any of the tests, the value where $p<0.05$ is defined to be statistically significant.

Example XXII

Effectiveness of TPA in the Treatment of Stroke Using a Temporary Middle Cerebral Artery Occlusion Model Male C57B 16 mice (25-30 g) are used in this study. Mice are anesthetized with Isoflurane (3% induction, 1-2% maintenance). The surgical site is clipped and cleaned with alcohol and surgical scrub. A midline neck incision is made over the carotid artery and the artery is dissected to its bifurcation. A monofilament suture is introduced into the internal carotid artery and advanced until it lodges in the middle cerebral artery. The suture is tied in placed and the incision is closed. Two hours after occlusion the mice will be re-anesthetized and the suture will be removed from the MCA. Body temperature is maintained by use of a heating pad both during and after surgery. Animals are monitored for 4 hours following middle cerebral artery occlusion.

The rats are divided into four groups. The first group of rats is given saline injections every other day. Groups 2-4 are given 0.125 mg/m$^2$ injection every other day for four weeks. Group 2 is then sacrificed. Groups 3-4 are given a further 0.156 mg/m$^2$ every other day for two weeks and then Group 3 is sacrificed. Group 4 is given 0.18775 mg/m$^2$ every other day for three weeks and then sacrificed.

The brains are excised after the animals are sacrificed and sliced in ten sections at 1 mm intervals using a McIwain tissue chopper (Mickle Laboratory Engineering, U.K.) and are stained by dipping for 20 minutes in a 2% TTC (2,3,5-triphenyltetrazolium chloride; Tokyo Kasei) at 37° C. Images of the TTC-stained slices are uploaded into a computer using a digital camera (HC-2500; Fuji PhotoFilm) and Phatograb-2500 (Fuji Photo Film). Brain slices are photographed and analyzed for infarct size, infarct volume, penumbra, and edema.

Neurological symptoms are observed daily until sacrifice and the rats are evaluated according to three tests. (1) Rats are held gently by the tail, suspended one meter above the floor, and observed for forelimb flexion. (2) Rats are placed on a large sheet of soft, plastic coated paper that could be gripped firmly by their claws. With the tail held by hand, gentle lateral pressure is applied behind the rat's shoulder until the forelimbs slid several inches. (3) Rats are allowed to move about freely and are observed for circling behavior. Scoring of the neurological symptoms is carried out according to the scale developed by Bederson et al. (1986) as follows: 0: no observable deficit; 1: forelimb flexion; 2: decreased resistance to lateral push without circling; 3: same behavior as grade 2, with circling.

Neurological symptoms are evaluated using a Steel's test for the control group and for each of the TPA administered groups as compared with the control group and then by carrying out a Wilcoxon test for the TPA administered group. In any of the tests, the value where $p<0.05$ is defined to be statistically significant.

Example XXIII

Clinical Effectiveness of the Use of TPA to Treat Stroke

Males and Females between the ages of 30-72 years who suffered a stroke less than one month previously are recruited for participation in a ten week trial of TPA.

Recruited individuals sign an informed consent form and are evaluated using computed tomography (CT), physical and neurological tests, neurological check, sedation level, National Institute of Health Stroke Survey (NIHSS), 12-lead electrocardiogram, telemetry of electrocardiogram, pulse oxygen measurement, vital sign, body weight, background of the patient, test on pregnancy, measurement of medicament in urine, hematological test, coagulation panel, general clinical test, urine test. Clinical Laboratory Testing includes a Complete Metabolic Panel (Na, K, Cl, CO2, Glu, BUN, Cr, Ca, TP, Alb, TBili, AP, AST, ALT), Hematology CBC (Hgb, Hct, RBC, WBC, Plt, Diff), and Serum hCG for all females.

Individuals are administered 0.125 mg/m$^2$ of TPA or placebo every other day for four weeks, then 1.25×0.125 mg/m$^2$ or placebo every other day for weeks five and six and 1.5×0.125 mg/m$^2$ or placebo every other day for weeks seven to nine. Individuals are monitored during and for two hours after administration of TPA or placebo.

At weeks five and week ten, subjects are evaluated using the NIHSS (NIH Stroke Scale), the Barthel ADL index (Granger, 1979), and a modified Rankin scale (Farrell, 1991), Efficacy is determined by measuring the change from baseline in the NIHSS in individuals treated with TPA in comparison to placebo. Secondary efficacy variables are the Barthel ADL index and a modified Rankin scale. Safety measures are collected and evaluated through the trial, specifically measuring changes from baseline visit to week 5. These measures include adverse event reports, physical examinations, vital signs, weight measurements, ECGs, clinical laboratory test results, and vital signs as well as scores for suicidal behaviors and/or ideation. Adverse events are any untoward medical event occurring in a subject administered study drug, irrespective of whether it has a causal relationship to the study drug. An adverse event can therefore be any unfavorable or unintended sign (including abnormal laboratory findings, for example), symptom, or disorder temporarily associated with study drug, whether or not considered related to the study drug.

Subjects are considered to have completed the study if they complete all of the visits. They may be terminated from the study if they fail to meet inclusion/exclusion criteria;

suffer from an adverse event, have an insufficient therapeutic response, withdraw their consent, violate the protocol, stop coming, or die.

Example XXIV

Reduction of Periorbital Hyperpigmentation 6 women and 1 man with excessive periorbital hyperpigmentation were treated with TPA. The treatment reduced the inflammation and hyperpigmentation in the periorbital area.

Example XXV

Treatment of Carpal Tunnel Syndrome

Female patient, age 50, with burning, tingling, pain and numbness in her fingers. She was treated with TPA and has regained full use of her hands.

Example XXVI

Anti-Aging Properties of TPA

Patient W.L, male, age 82 was being treated for prostate hypertrophy with 1.25 ampoules of 0.125 mg/m$^2$ every other day for two months. After treatment with TPA, his skin became softer and had fewer wrinkles.

Example XXVII

Treatment of Parkinson's Disease

Patient S. K., age 55, was diagnosed with Parkinson's disease. He was injected with 1 ampoule containing 0.19 mg of TPA (0.125 mg/m$^2$) TPA every other day for four weeks, then 0.24 mg of TPA (1.25×0.125 mg/m$^2$) every other day for 2 weeks, and 0.26 mg of TPA (1.5×0.125 mg/m$^2$) every other day for an additional 3 weeks. The patient is no longer displaying tremors.

Example XXVIII

Treatment of Prostate Hypertrophy

Patient W. L, male, age 82, diagnosed with prostate hypertrophy. He was injected with 1 ampoule containing 0.19 mg of TPA (0.125 mg/m$^2$) every other day for four weeks, then 0.24 mg of TPA (1.25×0.125 mg/m$^2$) every other day for 2 weeks, and 0.26 mg of TPA (1.5×0.125 mg/m$^2$) every other day for an additional 3 weeks. His PSA index is now below 3.0. The patient also developed a more youthful appearance.

Example XXIX

Treatment of Rheumatoid Arthritis

Patient received multiple injections of TPA and saw a reduction in stiffness in the joints and an increase in functionality in their hands.

Example XXX

Treatment of Collagen Induced Arthritis with TPA

Collagen induced arthritis (CIA) is induced as described previously (Rosloniec 2001), with minor modifications. Briefly, male DBA/1J mice are injected intradermally at the base of the tail with 100 µg of chicken type II collagen (Chondrex, Redmond, Wash.) in 0.05M acetic acid emulsified in Freund's complete adjuvant (Difco, Detroit, Mich.). Twenty-one days after primary immunization, the mice are administered a booster injection of type II collagen at the same dose level.

Mice are carefully examined each day from day 18 after the first collagen injection for the visual appearance of arthritis in peripheral joints. The clinical severity of arthritis is scored as follows: 1 point for each swollen digit except the thumb (maximum, 4), 1 point for the tarsal or carpal joint, and 1 point for the metatarsal or metacarpal joint with a maximum score of 6 for a hindpaw and 5 for a forepaw. Each paw is graded individually, the cumulative clinical arthritic score per mouse reaching a maximum of 22 points.

After receiving the booster shot, the mice are divided into two groups and either received vehicle or 0.125 mg/m$^2$ of TPA intraperitoneally on days 0, 2, 4, 6, and 8. At day 30 after the initial injection, the mice are sacrificed and the knees were dissected and fixed in 10% buffered formalin for 7 days. Fixed tissues are decalcified for 3 weeks in 15% EDTA, dehydrated, and embedded in paraffin. Sagittal sections (8 µm) of the whole knee joint are stained with Safranin-O and counterstained with fast green/iron hematoxylin. Histological sections are graded independently by two observers unaware of animal treatment using an established scoring system for synovial hyperplasia (from 0, no hyperplasia, to 3, most severe hyperplasia) and inflammatory cells in synovium (0, no inflammation, to 3, severely inflamed joint). Cartilage damage is determined by Safranin-O staining (from 0, no change from normal nonarthritic knee joint, fully stained cartilage, to 3, total loss of Safranin-O staining) as described in Marty, 2001.

Example XXXI

Treatment of Myasthenia Gravis

Patient C.L., male, age 63, suffered from myasthenia gravis for more than 40 years. He was taking dexamethasone and concurrently and was injected with 1 ampoule containing 0.19 mg of TPA (0.125 mg/m$^2$) every other day for four weeks, then 0.24 mg of TPA (1.25×0.125 mg/m$^2$) every other day for 2 weeks, and 0.26 mg of TPA (1.5×0.125 mg/m$^2$) every other day for an additional 3 weeks for a total of 35 injections of TPA. He no longer needs the dexamethasone and is now asymptomatic.

Example XXXII

Treatment of Urinary Incontinence

Patient W. C., Female, age 61, has suffered from urinary incontinence for more than 30 years. She received six injections of 0.18 mg of TPA (0.125 mg/m$^2$) and has regained normal urinary frequency.

Patient L.J., female, age 48, has suffered from urinary incontinence for fifteen years. She received nine injections of 0.18 mg of TPA (0.125 mg/m$^2$) and has regained normal urinary frequency.

REFERENCES

Abrahm J. L., Gerson S. L., Hoxie J. A., Tannenbaum s. h., Cassileth p. A., Cooper R. A. Differential effects of phorbol esters on normal myeloid precursors and leukemic cells. Cancer Res. 46, 3711-3716 (1986).

Altuwaijri S, Lin H K, Chuang K H, Lin W J, Yeh S, Hanchett L A, Rahman M M, Kang H Y, Tsai M Y, Zhang Y, Yang L, and Chang C. Interruption of nuclear factor kappaB signaling by the androgen receptor facilitates 12-O-tetradecanoylphorbolacetate-induced apoptosis in androgen-sensitive prostate cancer LNCaP cells. Cancer Res 2003; 63: 7106-12.

Ando I., Crawfor D. H. et al. Phorbol ester-induced expression and function of the interleukin 2 receptor in human B lymphocytes. Eur J Immunol. 15(4), 341-4 (1985).

Aye M. T., Dunne J. V. Opposing effects of 12-O-tetradecanoylphorbol 13-acetate on human myeloid and lymphoid cell proliferation. J Cell Physiol. 114(2), 209-14 (1983).

Bauer I., Al Sarraj J. et al. Interleukin-I beta and tetradecanoylphorbol acetate-induced biosynthesis of tumor necrosis factor alpha in human hepatoma cells involved the transcription factors ATF2 and c-Jun and stress-activated protein kinases. J Cell Biochem. 100(1), 242-255 (Epub ahead of print), (2006).

Beaupre D M and Kurzrock R. RAS and leukemia: from basic mechanisms to gene-directed therapy. J Clin Oncol 1999; 17: 1071-9.

Becker Y. The changes in the T helper I (TH1) and T helper (TH2) cytokine balance during HIV infection are indicative of an allergic response to viral proteins that may be reversed by TH2 cytokine inhibitors and immune response modifiers—a review and hypothesis. Virus Genes 28(1). 5-18 (2004).

Bederson J B, Pitts L H, Tsuji M, Nishimura M C, Davis R L, Bartkowski H. Rat middle cerebral artery occlusion: evaluation of the model and development of a neurologic examination. Stroke. 1986; 17: 472-476.

Beetz A., Messer G. et al. Induction of interldukin 6 by ionizing radiation in a human epethelial cell line: controlk by corticosteroids. Int j Radiat Biol 72(1), 33-43 (1997).

Berenblum I. A re-evaluation of the concept of co-carcinogenesis. Prog. Exp. Tumor Res. 11, 21-30 (1969).

Blockland S. et al. Activation of latent HIV-1 expression by the potent anti-tumor promoter 12-dexyphorbol-13-phenylacetate. Antiviral Res. 59, 89-98 (2003).

Blumberg PM., Protein kinase C as the receptor for the phorbol ester tumor promoters: sixth Rhoads memorial award lecture. Cancer Res. 1988 Jan. 1; 48(1):1-8.

Boutwell R. K. Biochemical mechanism of tumor promotion, in mechanisms of tumor promotion and co-carcinogenesis. Eds. Slaga, T. J., Sivak, A. J. and Boutwell, R. K. Raven, New York, 49-58 (1978).

Boutwell R. K. The function and mechanism of promoters of carcinogenesis. CRC Crit. Rev. Toxicol 2, 419-443 (1974).

Brose N, Rosenmund C. Move over protein kinase C, you've got company: alternative effectors of diacylglycerol and phorbol esters. JCell Sci; 115:4399-411 (2002). Cancer Chemother Pharmacol. June; 57(6):789-95 (2006).

Cheson B D, Cassileth P A, Head D R, Schiffer C A, Bennett J M, Bloomfield C D, Brunning R, Gale R P, Grever M R, Keating M J, and et al. Report of the National Cancer Institute-sponsored workshop on definitions of diagnosis and response in acute myeloid leukemia. J Clin Oncol 1990; 8: 813-9.

Chun T. W., Siliciano R. F. et al. Quantification of latent tissue reservoirs and total body viral load in HIV-1 infection. Nature 387 (8), 183-188 (1997).

Clerici M., Sheare G. M. A TH1-TH2 switch is a critical step in the etiology of HIV infection. Immunol. Today 14(3), 107-110 (1993).

Cui X X, Chang R L, Zheng X, Woodward D, Strair R, and Conney A H. A sensitive bioassay for measuring blood levels of 12-O-tetradecanoylphorbol-13-acetate (TPA) in patients: preliminary pharmacokinetic studies. Oncol Res 2002; 13: 169-74.

Deegan M. J., Maeda k. Differentiation of chronic lymphocytic leukemia cells after in vitro treatment with Epstein-Barr virus or phorbol ester. Immunologic and morphologic studies. Am J Hermatol. 17(4), 335-47 (1984).

Epperly M W, Gretton J E, Sikora C A, et al. Mitochondrial localization of superoxide dismutase is required for decreasing radiation-induced cellular damage. Radiat Res. 2003; 160:568-578.

Epperly M W, Gretton J A, DeFilippi S J, et al. Modulation of radiation-induced cytokine elevation associated with esophagitis and esophageal stricture by manganese superoxide dismutase-plasmid/liposome (SOD2-PL) gene therapy. Radiat Res. 2001; 155:2-14.

Falcioni F., Rautmann A. et al. Influence of TPA (12-O-tetradodecanoyl-phorbol-13-acetate) on human B lymphocte function. Clin Exp Immunol. 62(3), 163-2 (1985).

Farrell B, Godwin J, Richards S, Warlow C, et al. (1991). "The United Kingdom transient ischaemic attack (UK-TIA) aspirin trial: final results." J Neurol Neurosurg Psychiatry 54 (12): 1044-1054.

Forbes I. J., Zalewski P. D., Letarte M. Human B-lymphocyte maturation sequence revealed by TPA-induced differentiation of leukaemi cells. Immunobiology 163(1), 1-6 (1982).

Fujisawa K., Nasu K. et al. Production of interleukin (IL)-6 and IL-8 by a chorio-carcinama cell line, BeWo. Placenta 21(4), 354-60 (2000).

Gunjan Goel, Harinder P. S. Makkar, George Francis, and Klaus Becker. Phorbol Esters: Structure, Biological Activity, and Toxicity in Animals. International Journal of Toxicology, 26:279-288, 2007. Gogusev J., Barbey S., Nezelof C. Regulation of TNF-alpha and IL-1 gene expression during TPA-induced differentiation of "Malignant histiocyosis" DEL cell line t(5:6) (q35:P21). Anti-cancer Res. 16(1), 455-60 (1996).

Granger C V, Devis L S, Peters M C, Sherwood C C, Barrett J E. Stroke rehabilitation: analysis of repeated Barthel Index measures. Arch Phys Med Rehabil. 1979; 60:14-17.

Gulakowski R. J., McMahon J. B., Bukheit Jr., et al. Antireplicative and anti-cytopathic activities of prostratin, a non-tumor-promoting phorbol ester against human immunodefeciency virus (HIV). Antiviral Research 33, 87-97 (1997).

Hamburger, A. W., and Salmon, S. E. Primary bioassay of human tumor stem cells. Science (Wash. DC), 797: 461-463,1977.

Han Z T, Zhu X X, Yang R Y, Sun J Z, Tian G F, Liu X J, Cao G S, Newmark H L, Conney A H, and Chang R L. Effect of intravenous infusions of 12-O-tetradecanoyl-phorbol-13-acetate (TPA) in patients with myelocytic leukemia: preliminary studies on therapeutic efficacy and toxicity. Proc Natl Acad Sci USA 1998; 95: 5357-61.

Han Z. T., Tong Y. K., He L. M., Zhang Y., Sun J. Z., Wang T. Y., Zhang H., Cui Y. L., Newmark H. L., Conney A. H., Chang R. L. 12-O-Tetradecanoyl-phorbol-13-acetate (TPA)-induced increase in depressed white blood cell counts in patients treated with cytotoxic cancer chemotherapeutic drugs. Proc. Natl. Acad. Sci. 95, 5363-5365 (1998).

Han Z. T., Zhu X. X., Yang R. Y., Sun J. Z., Tian G. F., Liu X. J., Cao G. S., NewMark H. L., Conney A. H., and Chang R. L. Effect of intravenous infusion of 12-O-tetradecanoyl-phorbol-13-acetate (TPA) in patients with myelocytic leukemia: preliminary studies on therapeutic efficacy and toxicity. Pro. Natl. Acad. Sci. 95, 5357-5361 (1998).

Harada S. et al.: Tumor Promoter, TPA, Enhances Replication of HTLV-III/LAV. Virology 154, 249-258 (1986).

Harrigan, P. R., Whaley, M., Montaner, J. S. G. Rate of HIV-1 RNA rebound upon stopping antiretroviral therapy. AIDS 13, F59-F62 (1999).

Hecker E. In handbuch der allgemeinen patholgie, ed. Grundmann, E. (Springer-Verlag, Berlin-Heideiberg, Vol. IV 16, 651-676 (1975).

Hecker E. Structure-activity relationships in deterpene esters irritant and co-carcinogenic to mouse skin, in mechanisms of tumor promotion and co-carcinogenesis. Eds. Slaga, T. J., Sevak, A. j. and Boutwell, R. K. Raven, New York, 11-49 (1978).

Hofmann J. The potential for isoenzyme-selective modulation of protein kinase C. FASEB J. 11, 649-669 (1997).

Huberman E., Callaham M. F. Induction of terminal differentiation in human promyelocytic leukemia cells by tumor-promoting agents. Proc. Natl. Acad. Sci. 76, 1293-1297 (1979).

Hunter T. Signaling 2000 and beyond. Cell 100, 113-117 (2000). Jordan C T. Unique molecular and cellular features of acute myelogenous leukemia stem cells. Leukemia 2002; 16: 559-62.

Kassel O, Sancono A, Kratzschmar J, Kreft B, Stassen M, and Cato A C. Glucocorticoids inhibit MAP kinase via increased expression and decreased degradation of MKP-1. Embo J 2001; 20: 7108-16.

Kawakami A., Eguchi K. et al. Inhibitory effects of interleukin-10 on synovial cells of rheumatoid arthritis. Immumonolgy 81(2), 252-9 (1997).

Kazanietz M. G. Eyes Wide Shut: protein kinase C isoenzymes are not the only receptors for the phorbol ester tumor promoters. Mol. Carcinog. 28, 5-12 (2000).

Keoffler H. P., Bar-Eli M., Territo M. C. Phorbol ester effect on differentiation of human myeloid leukemia cells lines blocked at different stages of maturation. Cancer Res. 41, 919-926 (1981).

Kim S C, Hahn J S, Min Y H, Yoo N C, Ko Y W, and Lee W J. Constitutive activation of extracellular signal-regulated kinase in human acute leukemias: combined role of activation of MEK, hyperexpression of extracellular signal-regulated kinase, and downregulation of a phosphatase, PAC1. Blood 1999; 93: 3893-9.

Kiyoi H, Naoe T, Nakano Y, Yokota S, Minami S, Miyawaki S, Asou N, Kuriyama K, Jinnai I, Shimazaki C, Akiyama H, Saito K, Oh H, Motoji T, Omoto E, Saito H, Ohno R, and Ueda R. Prognostic implication of FLT3 and N-RAS gene mutations in acute myeloid leukemia. Blood 1999; 93: 3074-80.

Kobayashi M., Okada N. et al. Intracellular interleukin-1 alpha production in human gingival fibroblasts is differentially regulated by various cytokines. J Dent Res. 78(4), 840-9 (1999).

Koeffler H. P. Phorbol diester-induced macrophge differentiation of leukemic blasts from patients with human myelogenous leukemia. J. Clin. Invest. 66, 1101-1108 (1980).

Kulkosky J., Merantz R. J. et al. Prostratin: activation of latent HIV-1 expression suggested a potential inductive adjuvant therapy for HAART. Blood 98 (10), 3006-3015 (2001).

Kudo M., Aoyama A., Ichimori S. and Fukunaga N. An animal model of cerebral infarction: homologous blood clot emboli in rats. Stroke 13: 505-508 (1982) Lebien T. W., Bollum F. J. et al. Phorbol ester-induced differentiation of a non-T, non-B leudemic cell line: model for human lymphoid progenitor cell development. J Immunol. 128(3), 1316-20 (1982).

Lehrman G., Hogue I. B., Palme S. et al. Depletion of Latent HIV-V infection in vivo: a proof-of-concept study. Lancet 366 (9485), 523-524 (2005).

Lotem J., Sachs L. Regulation of normal differentiation in mouse and human myeloid leukemia cells by phorbol esters and the mechanism of tumor promotion. Pro. Natl. Acad. Sci. 76 5158-5162 (1979).

MD Iqbal Hossain Chowdhury et al. The Phorbol Ester TPA Strongly Inhibits HIV-1 Induced Syncytia Formation but Enhances Virus Production: possible involvement of protein kinase C pathway. Virology 176, 126-132, (1990).

Marty, Ingrid et al., Amelioration of collagen-induced arthritis by thrombin inhibition. J Clin Invest. 2001 March 1; 107(5): 631-640. Meinhardt G, Roth J, and Totok G. Protein kinase C activation modulates pro- and anti-apoptotic signaling pathways. Eur J Cell Biol 2000; 79: 824-33.

Meinhardt G., Roth J., Hass R. Activation of protein kinase C relays distinct signaling pathways in the same cell type: differentiation and caspase-mediated apoptosis. Cell Death Differ. 7, 795-803 (2000).

Milella M, Kornblau S M, Estrov Z, Carter B Z, Lapillonne H, Harris D, Konopleva M, Zhao S, Estey E, and Andreeff M. Therapeutic targeting of the MEK/MAPK signal transduction module in acute myeloid leukemia. J Clin Invest 2001; 108: 851-9.

Mochty-Rosen D., Kauvar L. M. Modulating protein kinase C signal transduction. Adv. Pharmacol. 44, 91-145 (1998).

Morgan M A, Dolp O, and Reuter C W. Cell-cycle-dependent activation of mitogen-activated protein kinase kinase (MEK-1/2) in myeloid leukemia cell lines and induction of growth inhibition and apoptosis by inhibitors of RAS signaling. Blood 2001; 97: 1823-34.

Nagasawa K., Chechgik B. E. et al. Modulation of human T-cell differentiation markers by 12-O-tetradecanoylphorbal-13-acetate. Thymus. 3(4-5), 307-18, (1981).

Nakao Y., Matsuda S. et al. Paradoxical anti-leukemic effects of plant-derived tumor promoters on a human thymic lymphoblast cell line. Int J Cancer 30(6), 687-95 (1982).

Nakao Y., Matsuda S. et al. Phorbol ester-induced differentiation of human T-lymphoblastic cell line HPB-ALL. Cancer Res. 42(9), 33843-50 (1982).

Newton A. C. Protein kinase C: structure, function and regulation. J. Biol. Chem. 270, 28495-28499 (1995).

Niederman T. M. J., Ratner L. et al. Human Immunodeficiency Virus Type I Nef Protein Inhibits NF-κB Induction in Human T Cells. J. Virology 66 (10), 6313-6219 (1992).

Norwell P., Shankey T. V. et al. Proliferation, differentiation and cytogenetics of chronic leukemic B lymphocytes cultured with mitomycin-treated normal cells. Blood 57(3), 444-51(1981).

O'Banion M. K., Miller J. C. et al. Interleukin-1 beta induces prostaglandin G/H synthase-2 (cyclooxygenase-2) in primary murine astrocyte cultures. J Neurochem 66(6), 2532-40 (1996).

Okamura J., Geffand E. W., Letarte M. Heterogenneity of the response of chronic lymphocytic leukemia cells to phorbol ester. Blood 60(5), 1082-8 (1982).

Palella F J, Jr, Delaney K M, Moorman A C, et al. Declining morbidity and mortality among patients with advanced human immunodeficiency virus infection. HIV Outpatient Study Investigators. N Engl J Med. 338:853-860 (1998).

Palombella V J, Rando O J, Goldberg A L, and Maniatis T. The ubiquitin-proteasome pathway is required for processing the NF-kappa B 1 precursor protein and the activation of NF-kappa B. Cell 1994; 78: 773-85.

Persaud D., Theodore P., Siliciano R. F. et al. A stable latent reservoir for HIV-1 in resting $CD4^+T$ lymophocytes in infected children. J. Clini, Invest. 115 (7), 995-1003 (2000).

Platanias L C. Map kinase signaling pathways and hematologic malignancies. Blood 2003; 101: 4667-79.

Polliack A., Leizerowitz R., Korkesh A., Gurfel D., Gamliel H., Galili U. Exposure to TPA in vitro as an aid in the classification of blasts in human myelogenous and lymphoid leukemias. Am. J. Hematol. 13, 199-211 (1982).

Redondo P., Garci-Foncillas J. et al. Differential modulation of IL-8 and TNF-alpha expression in human keratinocytes by buffomedil chlorhydrate and pentoxifylline. Exp. Dermatol. 6(4), 186-94 (1997).

Rosloniec E F, Cremer M, Kang A, Myers L K. Collagen-induced arthritis. In: Coligan J E, Kruisbeek A M, Margulies D H, Shevach E M, Strober W, editors. Current protocols in immunology. New York: John Wiley & Sons; 2001. p. 15.5.1.

Rovera G., Santoli D., Damsky C. Human promyelocytic cells in culture differentiate into macrophage-like cells treated with a phorbol diester. Pro. Natl. Acad. Sci. 7, 2779-2783 (1979).

Rullas J., Alcami J. et. al. Receptors in peripheral blood lymphocytes. Antivir. Ther. 9 (4). 545-554 (2004).

Rwigema J C, Beck B, Wang W, Doemling A, Epperly M W, Shields D, Goff J P, Franicola D, Dixon T, Frantz M C, Wipf P, Tyurina Y, Kagan V E, Wang H, Greenberger J S. Two strategies for the development of mitochondrion-targeted small molecule radiation damage mitigators. Int J Radiat Oncol Biol Phys. 2011 Jul. 1; 80(3):860-8. Epub 2011 Apr. 13 Sahar El-Mekkawy et. al. Anti-HIV-1 phorbol esters from the seeds of Croton tiglium. Phytochemistry 53, 457-464 (2000).

Schaar D, Goodell L, Aisner J, Cui X X, Han Z T, Chang R, Martin J, Grospe S, Dudek L, Riley J, Manago J, Lin Y, Rubin E H, Conney A, Strair R K. A phase I clinical trial of 12-O-tetradecanoylphorbol-13-acetate for patients with relapsed/refractory malignancies.

Scheinman R I, Cogswell P C, Lofquist A K, and Baldwin A S, Jr. Role of Transcriptional Activation of IkappaBalpha in Mediation of Immunosuppression by Glucocorticoids. Science 1995; 270: 283-286.

Shkolnick T., Schlossman S. F., Griffin J. D. Acute undifferentiated leukemia: induction of partial differentiation by phorbol ester. Leuk. Res. 9, 11-17 (1985).

Shwarz M. et. al. High-level IL-10 production by monoclonal antibody-stimulated human T cells. Immunology 86, 364-371 (1995).

Siliciano J. D., Siliciano R. F. et al. Longterm follow-up studies confirm the stability of the latent reservoir for HIV-1 in resting $CD4^+$ T cells. Nature Med. 9(6) 727-728 (2003).

Staber P B, Linkesch W, Zauner D, Beham-Schmid C, Guelly C, Schauer S, Sill H, and Hoefler G. Common alterations in gene expression and increased proliferation in recurrent acute myeloid leukemia. Oncogene 2004; 23: 894-904.

Steube K. G., Meyer C., Drexler H. G. Constitutive excretion of hematopoietic cytokines by human carcinoma cell lines and its up-regulation by interleukin-1 and phorbol ester. Oncol. Rep. 6(20), 427-32 (1999).

Strair R K, Schaar D, Goodell L, Aisner J, Chin K V, Eid J, Senzon R, Cui X X, Han Z T, Knox B, Rabson A B, Chang R, and Conney A. Administration of a phorbol ester to patients with hematological malignancies: preliminary results from a phase I clinical trial of 12-O-tetradecanoyl-phorbol-13-acetate. Clin Cancer Res 2002; 8: 2512-8

Sumitomo M, Shen R, Goldberg J S, Dai J, Navarro D, and Nanus D M. Neutral endopeptidase promotes phorbol ester-induced apoptosis in prostate cancer cells by inhibiting neuropeptide-induced protein kinase C delta degradation. Cancer Res 2000; 60: 6590-6.

Totterman T. H., Nilsson K., Sundstrom C. Phorbol ester-induced differentiation of chronic lymphoctic leukaemia cells. Nature 288(5787), 176-8 (1980) Towatari M, Iida H, Tanimoto M, Iwata H, Hamaguchi M, and Saito H. Constitutive activation of mitogen-activated protein kinase pathway in acute leukemia cells. Leukemia 1997; 11: 479-84.

Van Duuren, B. L. Tumor-promoting agents in two-stage carcinogenesis. Prog. Exp. Tumor Res. 11, 31-68 (1969).

Williams S. W. et al. Prostratin Antagonize HIV Latency by Activating NF-KB. J. Biol. Chem. 279, 42008-42017 (2004).

Yamamoto Y, Kiyoi H, Nakano Y, Suzuki R, Kodera Y, Miyawaki S, Asou N, Kuriyama K, Yagasaki F, Shimazaki C, Akiyama H, Saito K, Nishimura M, Motoji T, Shinagawa K, Takeshita A, Saito H, Ueda R, Ohno R, and Naoe T. Activating mutation of D835 within the activation loop of FLT3 in human hematologic malignancies. Blood 2001; 97: 2434-9.

YIP, Y. K. et al. Stimulation of human gamma interferon production by diterpene esters. Infection and Immunity 34(1) 131-139 (1981).

Zhao J., Sharma Y., Agarwal R. Significant inhibition by the flavonoid antioxidant silymarin against 12-O-tetrade-canoylphorbol 13-acetate-caused modulation of antioxidant and inflammatory enzymes and cyclooxygenase2 and interlukin-I alpha expression in SENCAR mouse epidermis: implications in the prevention of stage 1 tumor promotion. Mol Carcinog. 26(4), 321-33 (1999).

We claim:

1. A method for alleviating or treating one or more side effects of radiation comprising administering to a mammalian subject in need thereof, an effective amount of phorbol ester of Formula I, or a pharmaceutically-acceptable salt, isomer, enantiomer, solvate, hydrate, or polymorph thereof to said mammalian subject to alleviate or treat one or more side effects due to radiation

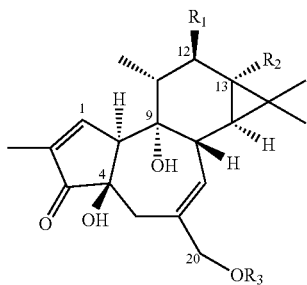

Formula I wherein $R_1$ and $R_2$ are selected from the group consisting of hydrogen, hydroxyl,

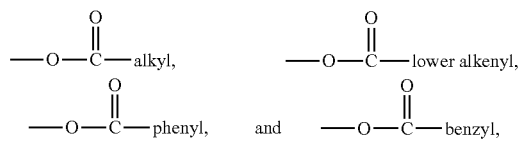

$R_3$ is hydrogen, and

2. The method of claim 1, wherein $R_1$ or $R_2$ is

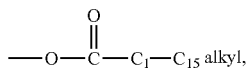

the remaining $R_1$ or $R_2$ is

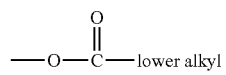

and $R_3$ is hydrogen.

3. The method of claim 1, wherein the phorbol ester is phorbol 13-butyrate, phorbol 12-decanoate, phorbol 13-decanoate, phorbol 12,13-diacetate, phorbol 13,20-diacetate, phorbol 12,13-dibenzoate, phorbol 12,13-dibutyrate, phorbol 12,13-didecanoate, phorbol 12,13-dihexanoate, phorbol 12,13-dipropionate, phorbol 12-myristate, phorbol 13-myristate, phorbol 12,13,20-triacetate, 12-deoxyphorbol 13-angelate, 12-deoxyphorbol 13-angelate 20-acetate, 12-deoxyphorbol 13-isobutyrate, 12-deoxyphorbol 13-isobutyrate-20-acetate, 12-deoxyphorbol 13-phenylacetate, 12-deoxyphorbol 13-phenylacetate 20-acetate, 12-deoxyphorbol 13-tetradecanoate, phorbol 12-tigliate 13-decanoate, 12-deoxyphorbol 13-acetate, phorbol 12-acetate, or phorbol 13-acetate.

4. The method of claim 1, further comprising administering at least one secondary or adjunctive therapeutic agent.

5. The method of claim 4, wherein the at least one secondary or adjunctive therapeutic agent is administered to said subject in a coordinate administration protocol, simultaneously with, prior to, or after, administration of said phorbol ester to said subject.

6. The method of claim 5, wherein the at least one secondary or adjunctive therapeutic agent is selected from the group consisting of steroids, amifostine, chlorhexidine, benzydamine, sucralfate, KGF, palifermin, Cu/Zn superoxide dismutase, Interleukin 11, or prostaglandins.

7. The method of claim 1, wherein the one or more side effects of radiation therapy are moist desquamation, soreness, diarrhea, nausea, vomiting, appetite loss, constipation, itchy skin, peeling, mouth and throat sores, edema, infertility, fibrosis, epilation, or mucosal dryness.

8. The method of claim 1, wherein said effective amount comprises between about 10 μg and about 1500 μg of said phorbol ester or derivative compound of Formula I every day.

9. The method of claim 1, wherein said effective amount comprises between about 125 μg to about 500 μg of said phorbol ester or derivative compound of Formula I every day.

* * * * *